US011160880B2

(12) United States Patent
Dorshow et al.

(10) Patent No.: US 11,160,880 B2
(45) Date of Patent: *Nov. 2, 2021

(54) COMPOSITIONS AND METHODS FOR ASSESSING EYE VASCULATURE

(71) Applicant: MediBeacon Inc., St. Louis, MO (US)

(72) Inventors: Richard B. Dorshow, St. Louis, MO (US); Thomas E. Rogers, Ballwin, MO (US)

(73) Assignee: MediBeacon Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/694,982

(22) Filed: Nov. 25, 2019

(65) Prior Publication Data

US 2020/0155708 A1    May 21, 2020

Related U.S. Application Data

(62) Division of application No. 15/572,706, filed as application No. PCT/US2016/032167 on May 12, 2016, now Pat. No. 10,525,149.

(60) Provisional application No. 62/160,338, filed on May 12, 2015.

(51) Int. Cl.
| | | |
|---|---|---|
| *A61K 49/00* | (2006.01) | |
| *A61B 5/00* | (2006.01) | |
| *C07K 5/06* | (2006.01) | |
| *C07D 241/20* | (2006.01) | |
| *C07K 5/078* | (2006.01) | |
| *A61B 1/04* | (2006.01) | |
| *A61B 5/026* | (2006.01) | |

(52) U.S. Cl.
CPC ........ *A61K 49/0021* (2013.01); *A61B 5/0071* (2013.01); *C07D 241/20* (2013.01); *C07K 5/06139* (2013.01); *A61B 1/042* (2013.01); *A61B 5/0082* (2013.01); *A61B 5/0261* (2013.01)

(58) Field of Classification Search
CPC ........... A61K 49/00; A61P 41/00; C07K 5/06; A61B 5/00
See application file for complete search history.

(56) References Cited

U.S. PATENT DOCUMENTS

| | | | |
|---|---|---|---|
| 3,814,747 A | 6/1974 | Donald | |
| 3,948,895 A | 4/1976 | Donald | |
| 6,440,950 B1 * | 8/2002 | Zeimer | A61P 41/00 514/63 |
| 8,115,000 B2 * | 2/2012 | Rajagopalan | A61K 49/0054 544/407 |
| 8,722,685 B2 | 5/2014 | Rajagopalan et al. | |
| 9,216,963 B2 | 12/2015 | Neumann et al. | |
| 9,283,288 B2 | 3/2016 | Dorshow et al. | |
| 9,480,687 B2 | 11/2016 | Rajagopalan et al. | |
| 2003/0236452 A1 | 12/2003 | Melker et al. | |
| 2006/0095102 A1 | 5/2006 | Perez | |
| 2008/0281173 A1 | 11/2008 | Esenaliev et al. | |
| 2010/0021382 A1 | 1/2010 | Dorshow et al. | |
| 2011/0250139 A1 | 10/2011 | Poreddy et al. | |
| 2011/0250140 A1 * | 10/2011 | Poreddy | A61K 49/00 424/9.1 |
| 2013/0116512 A1 | 5/2013 | Imran | |
| 2015/0112192 A1 | 4/2015 | Docherty et al. | |
| 2015/0306486 A1 | 10/2015 | Logan et al. | |

FOREIGN PATENT DOCUMENTS

| | | | |
|---|---|---|---|
| WO | 2007149479 A1 | 12/2007 | |
| WO | 2010078025 A1 | 7/2010 | |
| WO | 2010078028 A1 | 7/2010 | |
| WO | 2014149069 A1 | 9/2014 | |

OTHER PUBLICATIONS

Acheson et al., "Painful crises in sickle cell disease after fluorescein sodium angiography", Lancet, 1985, vol. 1, No. 8439, p. 1222.
Alario et al., Anterior segment fluorescein angiography of the normal canine eye using a DSLR camera adapter: Vet Ophthalmol, 2013; vol. 16, pp. 10-19.
Ascaso et al., "Fatal acute myocardial infarction after intravenous fluorescein angiography", Retina, 1993, vol. 13, pp. 238-239.
Balbino et al., "Anaphylaxis with convulsions following intravenous fluorescein sodium angiography at an outpatient clinic", Einstein (Sao Paulo), 2012, vol. 10, No. 3, pp. 374-376.
Bearelley et al., "Anaphylaxis following intravenous fluorescein sodium angiography in a vitreoretinal clinic: report of 4 cases", Can J Ophthalmol, 2009, vol. 44, pp. 444-445.
Brancato et al., "Iris fluorescein angiography in clinical practice", Surv Ophthalmol, 1997, vol. 42, pp. 41-70.
Bugaj et al., "Pre-clinical toxicity evaluation of MB-102, a novel fluorescent tracer agent for real-time measurement of glomerular filtration rate". Regul Toxicol Pharmacol, 2015, vol. 72, pp. 26-38.
Butner et al., "Adverse reactions in intravenous fluorescein sodium angiography", Ann Ophthalmol, 1983, vol. 15, pp. 1084-1086.
Chahal et al., "Metabolism of fluorescein after intravenous administration", Invest Ophthalmol Vis Sci, 1985, vol. 26, pp. 764-768.
Davidson et al., "Anaphylaxis Associated with Intravenous Sodium Fluorescein Administration in a Cat", Prog Vet & Comp Ophthal, 1991, vol. 1, No. 2, pp. 127-128.
Dorshow et al.. "Clinical study results of a real-time point-of-care glomerular filtration rate measurement", J Am Soc Nephrol, 2017, vol. 28, 12 pages.
Dorshow et al., "Initial clinical trial results of a real-time point-of-care glomerular filtration rate measurement utilizing a novel fluorescent tracer agent", J Am Soc Nephrol, 2015, vol. 26, pp. 259A.
Dorshow et al., "Next tier in vitro and in vivo nonclinical studies further elucidating the safety and toxicity profile of MB-102, a novel fluorescent tracer agent for measurement of glomerular filtration rate", Regul Toxicol Pharmacol, 2019, vol. 107, 104417, 11 pages.

(Continued)

*Primary Examiner* — Michael G. Hartley
*Assistant Examiner* — Jagadishwar R Samala
(74) *Attorney, Agent, or Firm* — Armstrong Teasdale LLP

(57) ABSTRACT

Compositions and methods for assessing blood vessels and organs of the body are disclosed herein, specifically methods for assessing the vasculature of the eye.

15 Claims, 1 Drawing Sheet

(56) References Cited

OTHER PUBLICATIONS

Elman et al., "Skin necrosis following fluorescein extravasation. A survey of the Macula Society", Retina, 1987, vol. 7, pp. 89-93.
Gelatt et al., "Fluorescein angiography of the normal and diseased ocular fundi of the laboratory dog", J Am Vet Med Assoc, 1976, vol. 169, pp. 980-984.
Gómez-Ulla et al., "Severe anaphylactic reaction to orally administered fluorescein", Am J Ophthalmol, 1991, vol. 112, No. 94, pp.
Grahn et al., "Retinopathy of coton detulear dogs: clinical manifestations, electroretinographic, ultrasonographic, fluorescein and indocyanine green angiographic, and optical coherence tomographic findings", Vet Ophthalmol, 2008, vol. 11, pp. 242-249.
Ha et al., "Anaphylaxis caused by intravenous fluorescein sodium: clinical characteristics and review of literature", Intern Emerg Med, 2014, vol. 9, No. 3, pp. 325-330.
Hochheimer et al., "Angiography With New Dyes", Experimental Eye Research, 1978, vol. 27, pp. 1-16.
Kinsella et al., "Anaphylaxis following oral fluorescein angiography", Am J. Ophthalmol, 1988, vol. 106, pp. 745-746.
Kobayashi et al., "Retinal vessel changes in galactose-fed dogs", Arch Ophthalmol, 1998, vol. 116, pp. 785-789.
Kottow, M., "Anterior segment fluorescein angiography", Baltimore: Williams and Wilkins, 1978, pp. 35-55.
Kwiterovich et al., "Frequency of adverse systemic reactions after fluorescein sodium angiography, Results of a prospective study", Ophthalmology, 1991, vol. 98, pp. 1139-1142.
Laatikainen, L., "Adverse effects of fluorescein angiography", Acta Ophthalmologica Scand, 2006, vol. 84, pp. 720-721.
Li et al., "Fluorescein binding to normal human serum proteins demonstrated by equilibrium dialysis", Arch Ophthalmol, 1982, vol. 100, pp. 484-487.
Lira et al., "Adverse reactions of fluorescein angiography: a prospective study", Arq Bras Ophthalmol, 2007, vol. 70, pp. 615-618.
Narfstrom et al., "Assessment of structure and function over a 3-year period after gene transfer in RPE65-/- dogs", Doc Ophthalmol, 2005, vol. 111, pp. 39-48.
Novotny et al., "A method of photographing fluorescence in circulating blood in the human retina", Circulation, 1961, vol. 24, pp. 82-86.
Pinhas et al., "In vivo imaging of human retinal microvasculature using adaptive optics scanning light ophthalmoscope fluorescein angiography", Biomed Optics Express, 2013, vol. 4, pp. 1305-1317.
Pirie et al., "Effectiveness of MB-102, a novel fluorescent tracer agent, for conducting ocular angiography in dogs", AJVR, May 2020, vol. 81, No. 5, pp. 428-436.
Pizzirani et al., "Transpupillary diode laser retinopexy in dogs: ophthalmoscopic, fluorescein angiographic and histopathologic study", Vet Ophthalmol, 2003, vol. 6, pp. 227-235.
Rajagopalan et al., "Hydrophilic Pyrazine Dyes as Exogenous Fluorescent Tracer Agents for Real-Time Point-of-Care Measurement of Glomerular Filtration Rate", Journal of Medicinal Chemistry, 2011, vol. 54, No. 14, pp. 5048-5058.
Rockey et al., "Eccleston JF. Binding of fluorescein and carboxyfluorescein by human serum proteins: significance of kinetic and equilibrium parameters of association in ocular fluorometric studies", Exp Eye Res, 1983, vol. 37, pp. 455-466.
Schaepdrijver et al., Fluorescein angiography of the canine retina:, Vet Comp Ophthalmol, 1996, vol. 6, pp. 111-119.
Stein et al., "Reactions following intravenous fluorescein sodium", Am J Ophthalmol, 1971, vol. 72, pp. 861-868.

Yannuzzi et al., "Effective differences in the formulation of intravenous fluorescein sodium and related side effects", Am J Ophthalmol, 1974, vol. 78, pp. 217-221.
Yannuzzi et al., "Fluorescein angiography complication survey", Ophthalmology, 1986, vol. 3, pp. 611-617.
International Report and Written Opinion for PCT/US2016/32167, dated Aug. 19, 2016, 9 pages.
Supplemental European Search Report for EP Application 16793545.1, dated Nov. 27, 2018, 8 pages.
Brenner et al., "Quantitative Importance of Changes in Postglomerular Colloid Osmotic Pressure in Mediating Glomerulotubular Balance in the Rat," The Journal of Clinical Investigation, vol. 52, (1973), pp. 190-197.
Chinen et al., "Fluorescence-Enhanced Europium-Diethylenetriaminepentaacetic (DTPA)-Monoamide Complexes for the Assessment of Renal Function," J. Med. Chem., vol. 51, (2008), pp. 957-962.
Dean et al., "Inulin, Diodone, Creatinine and Urea Clearances in Newborn Infants," J. Physiol., vol. 106, (1947), pp. 431-439.
Debreczeny et al., "Transdermal Optical Renal Function Monitoring in Humans: Development, Verification, and Validation of a Prototype Device," Journal of Biomedical Optics, vol. 23, No. 5, (May 2018), pp. 057003-1-057003-9.
Friedman et al., "A comparison of the renal clearances of allantoin and inulin in man," Fed. Proc., vol. 7, No. 1 Pt 1, (1948), 1 page.
Gregory et al., "Studies on Hypertension; Effect of Lowering the Blood Pressures of Hypertensive Patients by High Spinal Anesthesia on the Renal Function as Measured by Inulin and Diodrast Clearances," Arch. Intern. Med. (Chic), vol. 77, (1946), pp. 385-392.
Levin et al., "The Effect of Chronic Anemia on Renal Function as Measured by Inulin and Diodrast Clearances," Proc. Annu. Meet. Cent. Soc. Clin. Res. U. S., vol. 20, (1947), 3 pages.
Nagpal et al., "Combined Fluorescein, Indocyanine angiography and Optical Coherent Tomography Using Spectralis," Rajasthan Journal of Ophthalmology, (2011), 8 pages.
Navar et al., "Distal Tubular Feedback in the Autoregulation of Single Nephron Glomerular Filtration Rate," J. Clin. Invest., vol. 53, (1974), pp. 516-525.
Nicholson et al., "Renal Function as Affected by Experimental Unilateral Kidney Lesions: I. Nephrosis Due to odium Rartrate," J. Exp. Med., vol. 68, (1938), pp. 439-456.
Pill et al., "Fluorescein-labeled Sinistrin as Marker of Glomerular Filtration Rate," European Journal of Medicinal Chemistry, vol. 40, (2005), pp. 1056-1061.
Poujeol et al., "Glomerular Filtration Rate and Microsphere Distributions in Single Nephron of Rat Kidney," Pflugers Arch., vol. 357, (1975), pp. 291-301.
Robson et al., "The Determination of the Renal Clearance of Inulin in Man," Q. J. Exp. Physiol., vol. 35, (1949), pp. 111-134.
Schock-Kusch et al., "Transcutaneous measurement of glomerular filtration rate using FITC-sinistrin in rats," Nephrol Dial Transplant, vol. 24, (2009), pp. 2997-3001.
Shannon et al., "The Renal Excretion of Inulin and Creatinine by the Anaesthetized Dog and the Pump-Lung-Kidney Preparation", J. Physiol., vol. 98, (1940), pp. 97-108.
Yu et al., "Rapid determination of renal filtration function using an optical ratiometric imaging approach," Am. J. Physiol. Renal. Physiol., vol. 292, (2007), pp. F1873-F1880.
International Search Report received for PCT Patent Application No. PCT/US2019/013784, dated May 7, 2019, 6 pages.
International Preliminary Report on Patentability received for PCT Patent Application No. PCT/US2019/013784, dated Jul. 30, 2020, 8 pages.

* cited by examiner

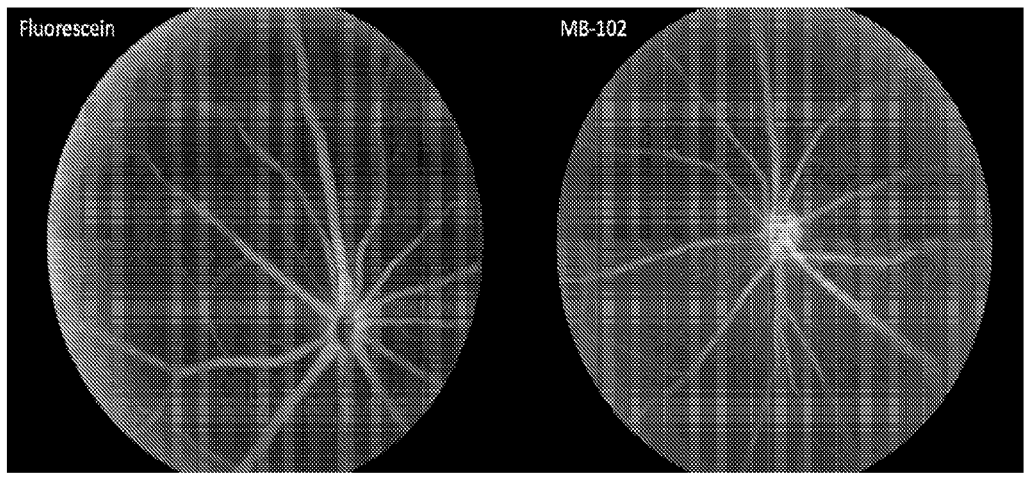

COMPOSITIONS AND METHODS FOR ASSESSING EYE VASCULATURE

CROSS-REFERENCE TO RELATED APPLICATIONS

This application is a divisional of U.S. application Ser. No. 15/572,706, filed Nov. 8, 2017, which is the U.S. National Phase Application of PCT/US2016/032167, filed May 12, 2016, which claims the benefit of priority of U.S. Provisional Application No. 62/160,338, filed May 12, 2015, the disclosures of which are hereby incorporated by reference as if written herein in their entirety.

The present disclosure relates to compositions and methods for assessing blood vessels and organs of the body, more specifically to methods for assessing the vasculature of the eye.

Angiography or arteriography is a medical imaging technique used to visualize the inside, or lumen, of blood vessels and organs of the body, with particular interest in the arteries, veins, and the heart chambers.

Ocular angiography is a technique for examining the vasculature of the retina and choroid using a fluorescent dye and a specialized camera. An eye angiogram helps eye doctors diagnose and manage the treatment of retinal diseases. For example, the test may locate the presence of abnormal blood vessels, blocked or leaking vessels, or identify inflammation and tumors in the eye.

Photography of the circulatory system of the eye and angiography of the ocular fundus requires introduction of a fluorescent dye into the blood as it flows through the vasculature of the eye. Sodium fluorescein (NaF), carboxyfluorescein (CF), indocyanine green (ICG), lissamine green, patent blue, Evans blue, and acridine orange have been used in the technique; however, sodium fluorescein is the only fluorescent dye currently in routine clinical use. Fluorescein and indocyanine green angiography have been used in the study of bleeding vessels, neovascularity, tumors and ischemic tissues in a variety of disorders.

Sodium fluorescein has its light absorption peak near 490 nm and it fluoresces maximally at 514 nm to 520 nm. The molecular weight of sodium fluorescein is 376 and it has a relatively high lipid solubility. Sodium fluorescein is readily metabolized to fluorescein glucuronide, a metabolite that is significantly less fluorescent than the parent having only 5% of the fluorescent yield as fluorescein. Further, immediately upon intra-venous injection, fluorescein is largely converted to a non-fluorescent serum protein bound molecule (93%). Given these factors, angiograms taken with sodium fluorescein have a relatively short working life-time in the retinal vasculature. Also, with sodium fluorescein, vitreous leakage may obscure retinal and choroidal structures which hinders photocoagulation therapy prior to or after angiography. Intravenous use of fluorescein may also cause adverse reactions such as nausea, vomiting, hives, acute hypotension, and anaphylaxis. One study reported on the nature and frequency of moderate and severe complications of intravenous fluorescein angiography. Adverse reactions were scored as mild, moderate or severe, depending on the duration of the effect, the necessity of medical intervention, the time required for its resolution, and the final outcome. The frequency rate for moderate reaction was one out of sixty three (1:63), for severe reaction, one out of nineteen hundred (1:1900) and for death 1:222,000. In several other studies, more cases of severe anaphylactic shock as well as death have been reported.

Thus, there remains a need for improved compositions and methods for assessing blood vessels and organs of the body, more specifically to methods for assessing the vasculature of the eye.

Accordingly, disclosed herein are improved compositions and methods for assessing blood vessels and organs of the body, more specifically to methods for assessing the vasculature of the eye.

Provided is a method for visualizing the vasculature of a subject in need thereof, comprising the steps of:

a. administering an effective amount of a compound of structural Formula I

or a salt thereof; wherein $X^1$ and $X^2$ are independently chosen from —CO (AA), —CN, —CO$_2$R$^1$, —CONR$^2$R$^3$, —COR$^4$, —NO$_2$, —SOR$^{35}$, —SO$_2$R$^6$, —SO$_2$OR$^7$ and —PO$_3$R$^8$R$^9$;

$Y^1$ and $Y^2$ are independently chosen from —OR$^{10}$, —SR$^{11}$, —NR$^{12}$R$^{13}$, —N(R$^{14}$)COR$^{15}$, —CONH (PS); —P(R$^{16}$)$_2$, —P(OR$^{17}$)$_2$ and

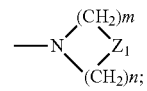

each $Z^1$ is independently chosen from a bond, —CR$^{18}$R$^{19}$—, —O—, NR$^{20}$—, —NCOR$^{21}$—, —S—, —SO—, and —SO$_2$—, each $R^1$ to $R^{21}$ are independently chosen from hydrogen, C$_1$-C$_{10}$ alkyl optionally substituted with hydroxyl and carboxylic acid, C$_3$-C$_6$ polyhydroxylated alkyl, C$_5$-C$_{10}$ aryl, C$_5$-C$_{10}$ heteroaryl, C$_3$-C$_5$ heterocycloalkyl optionally substituted with C(O), —(CH$_2$)$_a$CO$_2$H optionally substituted with C$_5$-C$_{10}$ heteroaryl, —(CH$_2$)$_a$CONR$^{30}$R$^{31}$, —(CH$_2$)$_a$NHSO$_3$, —(CH$_2$)$_a$NHSO$_3$H, —(CH$_2$)$_a$OH, —(CH$_2$)$_a$OPO$_3$, —(CH$_2$)$_a$OPO$_3$H$_2$, —(CH$_2$)$_a$OPO$_3$H$^-$, —(CH$_2$)$_a$OR$^{22}$, —(CH$_2$)$_a$OSO$_3$, —(CH$_2$)$_a$OSO$_3$H, —(CH$_2$)$_a$PO$_3^=$, —(CH$_2$)$_a$PO$_3$H$_2$, —(CH$_2$)$_a$PO$_3$H, —(CH$_2$)$_a$SO$_3$, —(CH$_2$)$_a$SO$_3$H, —(CH$_2$)$_a$CO(CH$_2$CH$_2$O)$_c$R$^{23}$, —(CH$_2$)$_d$(CH$_2$CH$_2$O)$_c$R$^{24}$, —(CHCO$_2$H)$_a$CO$_2$H, —CH$_2$(CHNH$_2$)$_a$CH$_2$NR$^{25}$R$^{26}$, —CH$_2$(CHOH)$_a$CO$_2$H, —CH$_2$(CHOH)$_a$R$^{27}$, —CH[(CH$_2$)$_b$NH$_2$]$_a$CH$_2$OH, —CH[(CH$_2$)$_b$NH$_2$]$_a$CO$_2$H, and —(CH$_2$)$_a$NR$^{28}$R$^{29}$;

each $R^{22}$ to $R^{31}$ are independently chosen from hydrogen, C$_1$-C$_{10}$ alkyl, and C$_1$-C$_5$-dicarboxylic acid;

$R^{35}$ is chosen from C$_1$-C$_{10}$ alkyl optionally substituted with hydroxyl and carboxylic acid, C$_3$-C$_6$ polyhydroxylated alkyl, C$_5$-C$_{10}$ aryl, C$_5$-C$_{10}$ heteroaryl, C$_3$-C$_5$ heterocycloalkyl optionally substituted with C(O), —(CH$_2$)$_a$CO$_2$H optionally substituted with C$_5$-C$_{10}$ heteroaryl, —(CH$_2$)$_a$CONR$^{30}$R$^{31}$, —(CH$_2$)$_a$NHSO$_3^-$, —(CH$_2$)$_a$NHSO$_3$H, —(CH$_2$)$_a$OH, —(CH$_2$)$_a$OPO$_3^-$, —(CH$_2$)$_a$OPO$_3$H$_2$, —(CH$_2$)$_a$OPO$_3$H$^-$, —(CH$_2$)$_a$OR$^{22}$, —(CH$_2$)$_a$OSO$_3^-$, —(CH$_2$)$_a$OSO$_3$H, —(CH$_2$)$_a$PO$_3^-$, —(CH$_2$)$_a$PO$_3$H$_2$, —(CH$_2$)$_a$PO$_3$H$^-$, —(CH$_2$)$_a$SO$_3^-$, —(CH$_2$)$_a$SO$_3$H, —(CH$_2$)$_d$CO(CH$_2$CH$_2$O)$_c$R$^{23}$, —(CH$_2$)$_d$(CH$_2$CH$_2$O)$_c$R$^{24}$, —(CHCO$_2$H)$_a$CO$_2$H, —CH$_2$(CHNH$_2$)$_a$CH$_2$NR$^{25}$R$^{26}$, —CH$_2$(CHOH)$_a$CO$_2$H, —CH$_2$(CHOH)$_a$R$^{27}$, —CH[(CH$_2$)$_b$NH$_2$]$_a$CH$_2$OH, —CH[(CH$_2$)$_b$NH$_2$]$_a$CO$_2$H, and —(CH$_2$)$_a$NR$^{28}$R$^{29}$;

(AA) is a polypeptide chain comprising one or more natural or unnatural amino acids linked together by peptide bonds;

(PS) is a sulfated or non-sulfated polysaccharide chain comprising one or more monosaccharide units connected by glycosidic linkages; and each 'a', 'b', and 'd' are independently chosen from 0 to 10, 'c' is chosen from 1 to 100 and each of 'm' and 'n' independently is an integer from 1 to 3;

b. irradiating the subject's vasculature with non-ionizing radiation, wherein the radiation causes the compound to fluoresce;

c. detecting the fluorescence of the compound in the subject's vasculature; and d. visualizing the vasculature within the subject based on the detected fluorescence.

Provided is a method of assessing the location of a disease or an injury in a subject's vasculature, comprising the steps of:

a. administering an effective amount of a compound of structural Formula I or a salt thereof; wherein

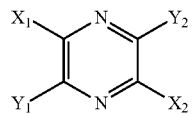

(I)

X$^1$ and X$^2$ are independently chosen from —CO(AA), —CN, —CO$_2$R$^1$, —CONR$^2$R$^3$, —COR$^4$, —NO$_2$, —SOR$^{35}$, —SO$_2$R$^6$, —SO$_2$OR$^7$ and —PO$_3$R$^8$R$^9$;

Y$^1$ and Y$^2$ are independently chosen from —OR$^{10}$, —SR$^{11}$, —NR$^{12}$R$^{13}$, —N(R$^{14}$)COR$^{15}$, —CONH(PS); —P(R$^{16}$)$_2$, —P(OR$^{17}$)$_2$ and

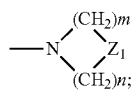

each Z$^1$ is independently chosen from a bond, —CR$^{18}$R$^{19}$—, —O—, —NR$^{20}$—, —NCOR$^{21}$—, —S—, —SO—, and —SO$_2$—;

each R$^1$ to R$^{21}$ are independently chosen from hydrogen, C$_1$-C$_{10}$ alkyl optionally substituted with hydroxyl and carboxylic acid, C$_3$-C$_6$ polyhydroxylated alkyl, C$_5$-C$_{10}$ aryl, C$_5$-C$_{10}$ heteroaryl, C$_3$-C$_5$ heterocycloalkyl optionally substituted with C(O), —(CH$_2$)$_a$CO$_2$H optionally substituted with C$_5$-C$_{10}$ heteroaryl, —(CH$_2$)$_a$CONR$^{30}$R$^{31}$, —(CH$_2$)$_a$NHSO$_3^-$, —(CH$_2$)$_a$NHSO$_3$H, —(CH$_2$)$_a$OH, —(CH$_2$)$_a$OPO$_3^=$, —(CH$_2$)$_a$OPO$_3$H$_2$, —(CH$_2$)$_a$OPO$_3$H$^-$, —(CH$_2$)$_a$OR$^{22}$, —(CH$_2$)$_a$OSO$_3^-$, —(CH$_2$)$_a$OSO$_3$H, —(CH$_2$)$_a$PO$_3^=$, —(CH$_2$)$_a$PO$_3$H$_2$, —(CH$_2$)$_a$PO$_3$H$^-$, —(CH$_2$)$_a$SO$_3^-$, —(CH$_2$)$_a$SO$_3$H, —(CH$_2$)$_d$CO(CH$_2$CH$_2$O)$_c$R$^{23}$, —(CH$_2$)$_d$(CH$_2$CH$_2$O)$_c$R$^{24}$, —(CHCO$_2$H)$_a$CO$_2$H, —CH$_2$(CHNH$_2$)$_a$CH$_2$NR$^{25}$R$^{26}$, —CH$_2$(CHOH)$_a$CO$_2$H, —CH$_2$(CHOH)$_a$R$^{27}$, —CH[(CH$_2$)$_b$NH$_2$]$_a$CH$_2$OH, —CH[(CH$_2$)$_b$NH$_2$]$_a$CO$_2$H, and —(CH$_2$)$_a$NR$^{28}$R$^{29}$;

each R$^{22}$ to R$^{31}$ are independently chosen from hydrogen, C$_1$-C$_{10}$ alkyl, and C$_1$-C$_5$-dicarboxylic acid;

R$^{35}$ is chosen from C$_1$-C$_{10}$ alkyl optionally substituted with hydroxyl and carboxylic acid, C$_3$-C$_6$ polyhydroxylated alkyl, C$_5$-C$_{10}$ aryl, C$_5$-C$_{10}$ heteroaryl, C$_3$-C$_5$ heterocycloalkyl optionally substituted with C(O), —(CH$_2$)$_a$CO$_2$H optionally substituted with C$_5$-C$_{10}$ heteroaryl, —(CH$_2$)$_a$CONR$^{30}$R$^{31}$, —(CH$_2$)$_a$NHSO$_3^-$, —(CH$_2$)$_a$NHSO$_3$H, —(CH$_2$)$_a$OH, —(CH$_2$)$_a$OPO$_3^=$, —(CH$_2$)$_a$OPO$_3$H$_2$, —(CH$_2$)$_a$OPO$_3$H$^-$, —(CH$_2$)$_a$OR$^{22}$, —(CH$_2$)$_a$OSO$_3^-$, —(CH$_2$)$_a$OSO$_3$H, —(CH$_2$)$_a$PO$_3^-$, —(CH$_2$)$_a$PO$_3$H$_2$, —(CH$_2$)$_a$PO$_3$H$^-$, —(CH$_2$)$_a$SO$_3^-$, —(CH$_2$)$_a$SO$_3$H, —(CH$_2$)$_d$CO(CH$_2$CH$_2$O)$_c$R$^{23}$, —(CH$_2$)$_d$(CH$_2$CH$_2$O)$_c$R$^{24}$, —(CHCO$_2$H)$_a$CO$_2$H, —CH$_2$(CHNH$_2$)$_a$CH$_2$NR$^{25}$R$^{26}$, —CH$_2$(CHOH)$_a$CO$_2$H, —CH$_2$(CHOH)$_a$R$^{27}$, —CH[(CH$_2$)$_b$NH$_2$]$_a$CH$_2$OH, —CH[(CH$_2$)$_b$NH$_2$]$_a$CO$_2$H, and —(CH$_2$)$_a$NR$^{28}$R$^{29}$;

(AA) is a polypeptide chain comprising one or more natural or unnatural amino acids linked together by peptide bonds;

(PS) is a sulfated or non-sulfated polysaccharide chain comprising one or more monosaccharide units connected by glycosidic linkages; and each 'a', 'b', and 'd' are independently chosen from 0 to 10, 'c' is chosen from 1 to 100 and each of 'm' and 'n' independently is an integer from 1 to 3;

b. irradiating the subject's vasculature with non-ionizing radiation, wherein the radiation causes the compound to fluoresce;

c. detecting the fluorescence of the compound in the subject's vasculature; and d. assessing the location of disease or injury in the subject's vasculature, based on the detected fluorescence.

Provided is kit for assessing the vasculature in a subject in need thereof, comprising:

a. a compound of structural Formula I or a salt thereof; wherein

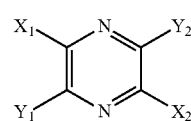

(I)

X$^1$ and X$^2$ are independently chosen from —CO(AA), —CN, —CO$_2$R$^1$, CONR$^2$R$^3$, —COR$^4$, —NO$_2$, —SOR$^{35}$, —SO$_2$R$^6$, —SO$_2$OR$^7$ and —PO$_3$R$^8$R$^9$;

Y$^1$ and Y$^2$ are independently chosen from —OR$^{10}$, —SR$^{11}$, —NR$^{12}$R$^{13}$, —N(R$^{14}$)COR$^{15}$, —CONH(PS); —P(R$^{16}$)$_2$, —P(OR$^{17}$)$_2$ and

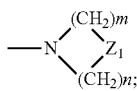

each $Z^1$ is independently chosen from a bond, —$CR^{18}R^{19}$—, —O—, —$NR^{20}$—, —$NCOR^{21}$—, —S—, —SO—, and —$SO_2$—, each $R^1$ to $R^{21}$ are independently chosen from hydrogen, $C_1$-$C_{10}$ alkyl optionally substituted with hydroxyl and carboxylic acid, $C_3$-$C_6$ polyhydroxylated alkyl, $C_5$-$C_{10}$ aryl, $C_5$-$C_{10}$ heteroaryl, $C_3$-$C_5$ heterocycloalkyl optionally substituted with C(O), —$(CH_2)_aCO_2H$ optionally substituted with $C_5$-$C_{10}$ heteroaryl, —$(CH_2)_aCONR^{30}R^{31}$, —$(CH_2)_aNHSO_3$, —$(CH_2)_aNHSO_3H$, —$(CH_2)_aOH$, —$(CH_2)_aOPO_3^=$, —$(CH_2)_aOPO_3H_2$, —$(CH_2)_aOPO_3H^-$, —$(CH_2)_aOR^{22}$, —$(CH_2)_aOSO_3^-$, —$(CH_2)_aOSO_3H$, —$(CH_2)_aPO_3^-$, —$(CH_2)_aPO_3H_2$, —$(CH_2)_aPO_3H^-$, —$(CH_2)_aSO_3^-$, —$(CH_2)_aSO_3H$, —$(CH_2)_dCO(CH_2CH_2O)_cR^{23}$, —$(CH_2)_d(CH_2CH_2O)_cR^{24}$, —$(CHCO_2H)_aCO_2H$, —$CH_2(CHNH_2)_a$ $CH_2NR^{25}R^{26}$, —$CH_2(CHOH)_aCO_2H$, —$CH_2(CHOH)_aR^{27}$, —$CH[(CH_2)_bNH_2]_aCH_2OH$, —$CH[(CH_2)_bNH_2]_aCO_2H$, and —$(CH_2)_aNR^{28}R^{29}$;

each $R^{22}$ to $R^{31}$ are independently chosen from hydrogen, $C_1$-$C_{10}$ alkyl, and $C_1$-$C_5$-dicarboxylic acid;

$R^{35}$ is chosen from $C_1$-$C_{10}$ alkyl optionally substituted with hydroxyl and carboxylic acid, $C_3$-$C_6$ polyhydroxylated alkyl, $C_5$-$C_{10}$ aryl, $C_5$-$C_{10}$ heteroaryl, $C_3$-$C_5$ heterocycloalkyl optionally substituted with C(O), —$(CH_2)_aCO_2H$ optionally substituted with $C_5$-$C_{10}$ heteroaryl, —$(CH_2)_aCONR^{30}R^{31}$, —$(CH_2)_aNHSO_3^-$, —$(CH_2)_aNHSO_3H$, —$(CH_2)_aOH$, —$(CH_2)_aOPO_3^=$, —$(CH_2)_aOPO_3H_2$, —$(CH_2)_aOPO_3H^-$, —$(CH_2)_aOR^{22}$, —$(CH_2)_aOSO_3^-$, —$(CH_2)_aOSO_3H$, —$(CH_2)_aPO_3^-$, —$(CH_2)_aPO_3H_2$, —$(CH_2)_aPO_3H^-$, —$(CH_2)_aSO_3^-$, —$(CH_2)_aSO_3H$, —$(CH_2)_dCO(CH_2CH_2O)_cR^{23}$, —$(CH_2)_d$ $(CH_2CH_2O)_cR^{24}$, —$(CHCO_2H)_aCO_2H$, —$CH_2$ $(CHNH_2)_aCH_2NR^{25}R^{26}$, —$CH_2(CHOH)_aCO_2H$, —$CH_2(CHOH)_aR^{27}$, —$CH[(CH_2)_bNH_2]_a$ $CH_2OH$, —$CH[(CH_2)_bNH_2]_aCO_2H$, and —$(CH_2)_aNR^{28}R^{29}$;

(AA) is a polypeptide chain comprising one or more natural or unnatural amino acids linked together by peptide bonds;

(PS) is a sulfated or non-sulfated polysaccharide chain comprising one or more monosaccharide units connected by glycosidic linkages; and each 'a', 'b', and 'd' are independently chosen from 0 to 10, 'c' is chosen from 1 to 100 and each of 'm' and 'n' independently is an integer from 1 to 3; and b. written instructions for assessing the vasculature in the subject, comprising the steps of:
i. administering an effective amount of the compound of structural Formula I;
ii. irradiating the subject's vasculature with non-ionizing radiation, wherein the radiation causes the compound to fluoresce;
iii. detecting the fluorescence of the compound in the subject's vasculature; and

BRIEF DESCRIPTION OF THE DRAWINGS

FIG. 1. shows retinal imaging at 2 minutes following IV administration of fluorescein (left) or Example 2 (right) in mice.

DETAILED DESCRIPTION

Abbreviations and Definitions

To facilitate understanding of the disclosure, a number of terms and abbreviations as used herein are defined below as follows:

When introducing elements of the present disclosure or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.).

The term "about," as used herein, is intended to qualify the numerical values that it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —$C(O)CH_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, the alkenyl will comprise from 2 to 6 carbon atoms. The term "alkenylene" refers to a carbon-carbon double bond system attached at two or more positions such as ethenylene [(—CH=CH—), (—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, the alkyl will comprise from 1 to 10 carbon atoms. In further embodiments, the alkyl will comprise from 1 to 6 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, nonyl and the like. The term "alkylene," as used herein, alone or in combination, refers to a saturated aliphatic group derived from a straight or branched chain saturated hydrocarbon attached at two or more positions, such as methylene (~CH2-). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, the alkynyl comprises from 2 to 6 carbon atoms. In further embodiments, the alkynyl comprises from 2 to 4 carbon atoms. The term "alkynylene" refers to a carbon-carbon triple bond attached at two positions such as ethynylene (—C:::C—, —C—C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl" as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')-group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical C6H$_4$=derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group-with R and R' as defined herein.

The term "N-carbamyl" as used herein, alone or in combination, refers to a ROC(O)NR'-group, with R and R' as defined herein.

The term "carbonyl," as used herein, when alone includes formyl [—C(O)H] and in combination is a —C(O)-group.

The term "carboxyl" or "carboxy," as used herein, refers to —C(O)OH or the corresponding "carboxylate" anion, such as is in a carboxylic acid salt. An "O-carboxy" group refers to a RC(O)O-group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, the cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom selected from the group consisting of O, S, and N. In certain embodiments, the heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each the heteroatom may be independently selected from the group consisting of nitrogen, oxygen, and sulfur In certain embodiments, the hetercycloalkyl will comprise from 1 to 4 heteroatoms as ring members. In further embodiments, the hetercycloalkyl will comprise from 1 to 2 heteroatoms as ring members. In certain embodiments, the heterocycloalkyl will comprise from 3 to 8 ring members in each ring. In further embodiments, the heterocycloalkyl will comprise from 3 to 7 ring members in each ring. In yet further embodiments, the hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms.

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four the members may be heteroatoms selected from the group consisting of O, S, and N, or 2) bicyclic heteroaryl, wherein each of the fused rings comprises five or six ring members, comprising between them one to four heteroatoms selected from the group consisting of O, S, and N.

The term "lower cycloalkyl," as used herein, alone or in combination, means a monocyclic cycloalkyl having between three and six ring members. Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms selected from the group consisting of O, S, and N. Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently selected from the group consisting of hydrogen, lower alkyl, and lower heteroalkyl, any of which may be optionally substituted. Additionally, the R and R' of a lower amino group may combine to form a five- or six-membered heterocycloalkyl, either of which may be optionally substituted.

The term "mercaptyl" as used herein, alone or in combination, refers to an RS-group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'-group with R and R' as defined herein.

The term "S-sulfonamido" refers to a —S(=O)$_2$NRR', group, with R and R' as defined herein.

The terms "thia" and "thio," as used herein, alone or in combination, refer to a —S-group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)-group.

The term "N-thiocarbamyl" refers to an ROC(S)NR'-group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a X$_3$CS(O)$_2$NR-group with X is a halogen and R as defined herein.

The term "trihalomethanesulfonyl" refers to a X$_3$CS(O)$_2$-group where X is a halogen.

The term "trihalomethoxy" refers to a X$_3$CO-group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that the group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N$_3$, SH, SCH$_3$, C(O)CH$_3$, CO$_2$CH$_3$, CO$_2$H, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N (R)— may be attached to the parent moiety at either the carbon or the nitrogen.

(AA) is polypeptide chain including one or more natural or unnatural α-amino acids linked together by peptide bonds or natural or unnatural β-amino acid(s), linked together by peptide bonds or combination of α- and β-amino acid(s), linked by peptide bonds. The polypeptide chain (AA) may be a homopolypeptide chain or a heteropolypeptide chain, and may be any appropriate length. For instance, in some embodiments, the polypeptide chain may include 1 to 100 α-amino acid(s), 1 to 90 α-amino acid(s), 1 to 80 α-amino acid(s), 1 to 70 α-amino acid(s), 1 to 60 α-amino acid(s), 1 to 50 α-amino acid(s), 1 to 40 α-amino acid(s), 1 to 30 α-amino acid(s), 1 to 20 α-amino acid(s), or even 1 to 10 α-amino acid(s), In some embodiments, the α-amino acids of the polypeptide chain (AA) are selected from the group consisting of aspartic acid, asparagine, arginine, histidine, lysine, glutamic acid, glutamine, serine, and homoserine. In some embodiments, the α-amino acids of the polypeptide chain (AA) are selected from the group consisting of aspartic acid, glutamic acid, serine, and homoserine. In some embodiments, the polypeptide chain (AA) refers to a single amino (e.g., either aspartic acid or serine). In some embodiments, the polypeptide chain may include 1 to 100 β-amino acid(s), 1 to 90 β-amino acid(s), 1 to 80 β-amino acid(s), 1 to 70 β-amino acid(s), 1 to 60 β-amino acid(s), 1 to 50 β-amino acid(s), 1 to 40 β-amino acid(s), 1 to 30 β-amino acid(s), 1 to 20 β-amino acid(s), or even 1 to 10 β-amino acid(s). In some embodiments, a combination of α-amino acids and β-amino acids of the polypeptide chain may be included.

Asymmetric centers exist in the compounds disclosed herein. These centers are designated by the symbols "R" or "S," depending on the configuration of substituents around the chiral carbon atom. It should be understood that the disclosure encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present disclosure includes all cis, trans, syn, anti, entgegen (E), and zusammen (Z) isomers as well as the appropriate mixtures thereof. Additionally, compounds may exist as tautomers; all tautomeric isomers are provided by this disclosure. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The phrase "therapeutically effective" is intended to qualify the amount of active ingredients used in the treatment of a disease or disorder or on the effecting of a clinical endpoint.

The term "angiography" refers to a medical imaging technique for visualizing the lumen of a blood vessel, for example, an artery.

The term "vasculature" refers to blood vessels, such as veins and arteries, in the body or in an organ or body part. Although portions of this disclosure may refer to veins and arteries, this disclosure shall be applicable to any type of blood vessel within the "vascular system."

The term "pulmonary and cardiac vasculature" as used herein includes all of the blood vessels within the lungs and/or heart, the chambers of the heart, the passages between the chambers of the heart, as well as the blood vessels between the lungs and heart, and blood vessels between the lungs or heart and other tissues and/or organs. The pulmonary and cardiac vasculature includes, but is not limited to, the pulmonary veins and arteries and associated capillaries, the left and right atria of the heart, the left and right ventricles of the heart, the myocardium, the aorta and aortic arch, the coronary artery, the coronary arteries, the subclavian arteries, and the carotid arteries.

The term "abnormality" refers to the presence of an activity or feature which differs from a normal activity or feature. An abnormality may refer to a disease or disorder in need of treatment.

The term "stenosis" is defined to be a narrowing in a blood vessel or other tubular organ or structure, i.e. a vasoconstricting condition. This term also encompasses terms such as "restenosis" and "in-stent restenosis". The term "restenosis" refers to the reoccurrence of stenosis.

The term "occlusion" as used herein refers to an obstruction or closure of a passageway or vessel.

The term "aneurysm" refers to a localized dilation of a blood vessel, particularly of the aorta or a peripheral artery. Aneurysms are related to arteriosclerosis, cystic medial necrosis, pathogen infection, aortitis, and trauma, each of which may contribute to weakening of the vessel wall. Common aneurysm sites include the abdominal aorta, the thoracic aorta, peripheral arteries such as the popliteal, iliac, and femoral arteries.

The phrase "short-wavelength dye" in the context of this invention is intended to mean a dye capable of absorbing and/or emitting light in the blue or green portion of the electromagnetic spectrum.

The phrase "long-wavelength dye" in the context of this invention is intended to mean a dye capable of absorbing and/or emitting light in the red or infrared portion of the electromagnetic spectrum.

The term "low molecular weight dye" refers to a dye having a molecular weight of less than about 1,000 grams per mole ("g/mol").

The term "high molecular weight dye" refers to a dye having a molecular weight of greater than about 1,000 grams per mole ("g/mol").

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses.

The term "prodrug" refers to a compound that is made more active in vivo. Certain compounds disclosed herein may also exist as prodrugs, as described in Hydrolysis in Drug and Prodrug Metabolism: Chemistry, Biochemistry, and Enzymology (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present disclosure includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Pharmaceutical Salts: Properties, Selection, and Use (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present disclosure contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

A salt of a compound can be made by reacting the appropriate compound in the form of the free base with the appropriate acid.

Compositions

The present disclosure provides a composition for assessing eye vasculature in a subject in need thereof, comprising a fluorescent dye. The fluorescent dyes of the present disclosure tend to have absorption, excitation, and emission wavelengths that are all within the near-infrared (NIR) or visible spectrum of about 350 nm or greater. This is beneficial for diagnostic procedures since visible and NIR light are not likely to damage tissue. In contrast, ultraviolet (UV) light that has a wavelength of less than about 350 nm can damage tissue. Light having a wavelength of about 350 nm or greater tends to penetrate into tissues thereby permitting diagnostic procedures to be conducted in tissues of interest that may not be reachable using UV wavelengths that are less than about 350 nm.

Synthesis of pyrazine derivatives, in general, have been previously studied and described. Preparation procedures for some of the pyrazine derivatives of the present invention, using procedures similar to the above references, are described later in Examples 2 and 4-18.

Pyrazine dyes of the invention may be characterized as demonstrating absorption in the visible region and emission/fluorescence in the visible or near-infrared region, tend to exhibit significant Stokes shifts, and tend to be cleared from the body via the kidneys. These properties allow flexibility in both tuning a molecule to a desired wavelength and introducing a variety of substituents to improve pharmacokinetic (PK) and pharmacodynamics (PD) properties. The pyrazine derivatives described herein may be designed to be hydrophilic and/or have rigid functionality, thus providing desired pharmacokinetic properties appropriate for angiography in general and ocular angiography in particular.

Provided are compositions comprising a compound of structural Formula I

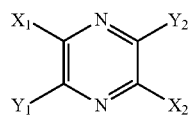

(I)

or a salt thereof; wherein $X^1$ and $X^2$ are independently chosen from —CO(AA), —CN, —CO$_2$R$^1$, —CONR$^2$R$^3$, —COR$^4$, —NO$_2$, —SOR$^{35}$, —SO$_2$R$^6$, —SO$_2$OR$^7$ and —PO$_3$R$^8$R$^9$;

$Y^1$ and $Y^2$ are independently chosen from —OR$^{10}$, —SR$^{11}$, —NR$^{12}$R$^{13}$, —N(R$^{14}$)COR$^{15}$, —CONH(PS); —P(R$^{16}$)$_2$, —P(OR$^{17}$)$_2$ and

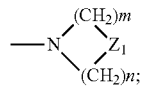

each $Z^1$ is independently chosen from a bond, —CR$^{18}$R$^{19}$—, —O—, —NR$^{20}$—, —NCOR$^{21}$—, —S—, —SO—, and —SO$_2$—;

each R$^1$ to R$^{21}$ are independently chosen from hydrogen, C$_1$-C$_{10}$ alkyl optionally substituted with hydroxyl and carboxylic acid, C$_3$-C$_6$ polyhydroxylated alkyl, C$_5$-C$_{10}$ aryl, C$_5$-C$_{10}$ heteroaryl, C$_3$-C$_5$ heterocycloalkyl optionally substituted with C(O), —(CH$_2$)$_a$CO$_2$H optionally substituted with C$_5$-C$_{10}$ heteroaryl, —(CH$_2$)$_a$CONR$^{30}$R$^{31}$, —(CH$_2$)$_a$NHSO$_3^-$, —(CH$_2$)$_a$NHSO$_3$H, —(CH$_2$)$_a$OH, —(CH$_2$)$_a$OPO$_3^=$, —(CH$_2$)$_a$OPO$_3$H$_2$, —(CH$_2$)$_a$OPO$_3$H, —(CH$_2$)$_a$OR$^{22}$, —(CH$_2$)$_a$OSO$_3$, —(CH$_2$)$_a$OSO$_3$H, —(CH$_2$)$_a$PO$_3^=$, —(CH$_2$)$_a$PO$_3$H$_2$, —(CH$_2$)$_a$PO$_3$H$^-$, —(CH$_2$)$_a$SO$_3^-$, —(CH$_2$)$_a$SO$_3$H, —(CH$_2$)$_d$CO(CH$_2$CH$_2$O)$_c$R$^{23}$, —(CH$_2$)$_d$(CH$_2$CH$_2$)$_c$R$^{24}$, —(CHCO$_2$H)$_a$CO$_2$H, —CH$_2$(CHNH$_2$)$_a$CH$_2$NR$^{25}$R$^{26}$, —CH$_2$(CHOH)$_a$CO$_2$H, —CH$_2$(CHOH)$_a$R$^{27}$, —CH[(CH$_2$)$_b$NH$_2$]$_a$CH$_2$OH, —CH[(CH$_2$)$_b$NH$_2$]$_a$CO$_2$H, and —(CH$_2$)$_a$NR$^{28}$R$^{29}$;

each R$^{22}$ to R$^{31}$ are independently chosen from hydrogen, C$_1$-C$_{10}$ alkyl, and C$_1$-C$_5$-dicarboxylic acid;

R$^{35}$ is chosen from C$_1$-C$_{10}$ alkyl optionally substituted with hydroxyl and carboxylic acid, C$_3$-C$_6$ polyhydroxylated alkyl, C$_5$-C$_{10}$ aryl, C$_5$-C$_{10}$ heteroaryl, C$_3$-C$_5$ heterocycloalkyl optionally substituted with C(O), —(CH$_2$)$_a$CO$_2$H optionally substituted with C$_5$-C$_{10}$ heteroaryl, (CH$_2$)$_a$CONR$^{30}$R$^{31}$, —(CH$_2$)$_a$NHSO$_3^-$, —(CH$_2$)$_a$NHSO$_3$H, —(CH$_2$)$_a$OH, —(CH$_2$)$_a$OPO$_3^=$, —(CH$_2$)$_a$OPO$_3$H$_2$, —(CH$_2$)$_a$OPO$_3$H$^-$, —(CH$_2$)$_a$OR$^{22}$, —(CH$_2$)$_a$OSO$_3^-$, —(CH$_2$)$_a$OSO$_3$H, —(CH$_2$)$_a$PO$_3^=$, —(CH$_2$)$_a$PO$_3$H$_2$, —(CH$_2$)$_a$PO$_3$H$^-$, —(CH$_2$)$_a$SO$_3^-$, —(CH$_2$)$_a$SO$_3$H, —(CH$_2$)$_d$CO(CH$_2$CH$_2$O)$_c$R$^{23}$, —(CH$_2$)$_d$(CH$_2$CH$_2$O)$_c$R$^{24}$, —(CHCO$_2$H)$_a$CO$_2$H, —CH$_2$(CHNH$_2$)$_a$CH$_2$NR$^{25}$R$^{26}$, —CH$_2$(CHOH)$_a$CO$_2$H, —CH$_2$(CHOH)$_a$R$^{27}$, —CH[(CH$_2$)$_b$NH$_2$]$_a$CH$_2$OH, —CH[(CH$_2$)$_b$NH$_2$]$_a$CO$_2$H, and —(CH$_2$)$_a$NR$^{28}$R$^{29}$;

(AA) is a polypeptide chain comprising one or more natural or unnatural β-amino acids or γ-amino acids linked together by peptide bonds;

(PS) is a sulfated or non-sulfated polysaccharide chain comprising one or more monosaccharide units connected by glycosidic linkages; and each 'a', 'b', and 'd' are independently chosen from 0 to 10, 'c' is chosen from 1 to 100 and each of 'm' and 'n' independently is an integer from 1 to 3.

In an embodiment, said compounds are at least partially renally excretable.

In an embodiment, said compounds are completely renally excretable.

Methods

In these methods, an effective amount of a pyrazine derivative is administered into the body of a patient (e.g., a mammal such as a human or animal subject). An "effective amount" herein generally refers to an amount of pyrazine derivative that is sufficient to enable angiographic function to be analyzed. The pyrazine derivative in the body of the patient is exposed to at least one of visible and near infrared light. Due to this exposure of the pyrazine derivative to the visible and/or infrared light, the pyrazine derivative emanates spectral energy that may be detected by appropriate detection equipment. This spectral energy emanating from the pyrazine derivative may be detected using an appropriate detection mechanism such as an invasive or non-invasive optical probe or photographic equipment such as a fundus camera. Herein, "emanating" or the like refers to spectral energy that is emitted and/or fluoresced from a pyrazine derivative. Angiographic function can be determined based the spectral energy that is detected. For example, an initial amount of the amount of pyrazine derivative present in the body of a patient may be determined by a magnitude/intensity of light emanated from the pyrazine derivative that is detected (e.g., in the retina). As the pyrazine derivative is cleared from the body, the magnitude/intensity of detected light generally diminishes. Accordingly, a rate at which this magnitude of detected light diminishes may be correlated with a subject's vasculature. This detection may be done periodically or in substantially real time.

The present disclosure provides new methods for visualizing the vasculature of a subject in need thereof, comprising the steps of: administering an effective amount of a compound of structural Formula I

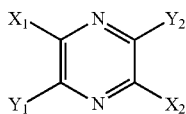

or a salt thereof; wherein
$X^1$ and $X^2$ are independently chosen from —CO(AA), —CN, —CO$_2$R$^1$, —CONR$^2$R$^3$, —COR$^4$, —NO$_2$, —SOR$^{35}$, —SO$_2$R$^6$, —SO$_2$R$^7$ and —PO$_3$R$^8$R$^9$;
$Y^1$ and $Y^2$ are independently chosen from —OR$^{10}$, —SR, —NR$^{12}$R$^{13}$, —N(R$^{14}$)COR$^{15}$, —CONH(PS); —P(R$^{16}$)$_2$, —P(OR$^{17}$)$_2$ and

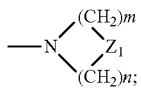

each $Z^1$ is independently chosen from a bond, —CR$^{18}$R$^{19}$—, —O—, —NR$^{20}$—, —NCOR$^{21}$—, —S—, —SO—, and —SO$_2$—;
each $R^1$ to $R^{21}$ are independently chosen from hydrogen, C$_1$-C$_{10}$ alkyl optionally substituted with hydroxyl and carboxylic acid, C$_3$-C$_6$ polyhydroxylated alkyl, C$_5$-C$_{10}$ aryl, C$_5$-C$_{10}$heteroaryl, C$_3$-C$_5$ heterocycloalkyl optionally substituted with C(O), —(CH$_2$)$_a$CO$_2$H optionally substituted with C$_5$-C$_{10}$ heteroaryl, —(CH$_2$)$_a$CONR$^{30}$R$^{31}$, —(CH$_2$)$_a$NHSO$_3^-$, —(CH$_2$)$_a$NHSO$_3$H, —(CH$_2$)$_a$OH, —(CH$_2$)$_a$OPO$_3^=$, —(CH$_2$)$_a$OPO$_3$H$_2$, —(CH$_2$)$_a$OPO$_3$H$^-$, —(CH$_2$)$_a$OR$^{22}$, —(CH$_2$)$_a$OSO$_3^-$, —(CH$_2$)$_a$OSO$_3$H, —(CH$_2$)$_a$PO$_3^-$, —(CH$_2$)$_a$PO$_3$H$_2$, —(CH$_2$)$_a$PO$_3$H$^-$, —(CH$_2$)$_a$SO$_3^-$, —(CH$_2$)$_a$SO$_3$H, —(CH$_2$)$_a$CO(CH$_2$CH$_2$O)$_c$R$^{23}$, (CH$_2$)$_d$(CH$_2$CH$_2$)$_c$R$^{24}$, —(CHCO$_2$H)$_a$CO$_2$H, —CH$_2$(CHNH$_2$)$_a$CH$_2$NR$^{25}$R$^{26}$, —CH$_2$(CHOH)$_a$CO$_2$H, —CH$_2$(CHOH)$_a$R$^{27}$, —CH[(CH$_2$)$_b$NH$_2$]$_a$CH$_2$OH, —CH[(CH$_2$)$_b$NH$_2$]$_a$CO$_2$H, and —(CH$_2$)$_a$NR$^{28}$R$^{29}$;
each $R^{22}$ to $R^{31}$ are independently chosen from hydrogen, C$_1$-C$_{10}$ alkyl, and C$_1$-C$_5$-dicarboxylic acid;
$R^{35}$ is chosen from C$_1$-C$_{10}$ alkyl optionally substituted with hydroxyl and carboxylic acid, C$_3$-C$_6$ polyhydroxylated alkyl, C$_5$-C$_{10}$ aryl, C$_5$-C$_{10}$ heteroaryl, C$_3$-C$_5$ heterocycloalkyl optionally substituted with C(O), —(CH$_2$)$_a$CO$_2$H optionally substituted with C$_5$-C$_{10}$ heteroaryl, —(CH$_2$)$_a$CONR$^{30}$R$^{31}$, —(CH$_2$)$_a$NHSO$_3^-$, —(CH$_2$)$_a$NHSO$_3$H, —(CH$_2$)$_a$OH, —(CH$_2$)$_a$OPO$_3^-$, —(CH$_2$)$_a$OPO$_3$H$_2$, —(CH$_2$)$_a$OPO$_3$H$^-$, —(CH$_2$)$_a$OR$^{22}$, —(CH$_2$)$_a$OSO$_3^-$, —(CH$_2$)$_a$OSO$_3$H, —(CH$_2$)$_a$PO$_3^=$, —(CH$_2$)$_a$PO$_3$H$_2$, —(CH$_2$)$_a$PO$_3$H$^-$, —(CH$_2$)$_a$SO$_3^-$, —(CH$_2$)$_a$SO$_3$H, —(CH$_2$)$_a$CO(CH$_2$CH$_2$O)$_c$R$^{23}$, —(CH$_2$)$_d$(CH$_2$CH$_2$O)$_c$R$^{24}$, —(CHCO$_2$H)$_a$CO$_2$H, —CH$_2$(CHNH$_2$)$_a$CH$_2$NR$^{25}$R$^{26}$, —CH$_2$(CHOH)$_a$CO$_2$H, —CH$_2$(CHOH)$_a$R$^{27}$, —CH[(CH$_2$)$_b$NH$_2$]$_a$CH$_2$OH, —CH[(CH$_2$)$_b$NH$_2$]$_a$CO$_2$H, and —(CH$_2$)$_a$NR$^{28}$R$^{29}$;
(AA) is a polypeptide chain comprising one or more natural or unnatural amino acids linked together by peptide bonds;
(PS) is a sulfated or non-sulfated polysaccharide chain comprising one or more monosaccharide units connected by glycosidic linkages; and
each 'a', 'b', and 'd' are independently chosen from 0 to 10, 'c' is chosen from 1 to 100 and each of 'm' and 'n' independently is an integer from 1 to 3;
irradiating the subject's vasculature with non-ionizing radiation, wherein the radiation causes the compound to fluoresce;
detecting the fluorescence of the compound in the subject's vasculature; and
visualizing the vasculature within the subject based on the detected fluorescence.

In an embodiment, said amino acids are chosen from α-amino acids, β-amino acids, and γ-amino acids.

In certain embodiments, the composition is administered intravenously.

In certain embodiments, the non-ionizing radiation has a wavelength of at least 350 nm.

In certain embodiments, the detected fluorescence of the compound in the subject's vasculature is measured over time.

In certain embodiments, the subject's pulmonary and cardiac vasculature is visualized. In some embodiments, visualizing the subject's pulmonary and cardiac vasculature comprises identifying abnormalities chosen from stenosis, occlusions, aneurysms, and combinations thereof. In some embodiments, visualizing the subject's pulmonary and cardiac vasculature comprises comparing the detected fluorescence in the subject's pulmonary and cardiac vasculature to that of normal pulmonary and cardiac vasculature under similar conditions.

In certain embodiments, the subject's eye vasculature is visualized. In some embodiments, visualizing the subject's eye vasculature comprises identifying ocular abnormalities. In some embodiments, the ocular abnormalities are chosen from blood vessel architecture, ischemic spots, choroidal infarcts, Elschnig's spots, exudates, hemorrhages, and combinations thereof. In some embodiments, the ocular abnormalities are chosen from vessel crossovers, vessel tortuosity, evidence of exudates, and combinations thereof. In some embodiments, visualizing the subject's eye vasculature comprises comparing the detected fluorescence in the subject's eye to that of a normal eye under similar conditions.

The present disclosure provides new methods for assessing the location of a disease or an injury in a subject's vasculature, comprising the steps of: administering an effective amount of a compound of structural Formula I

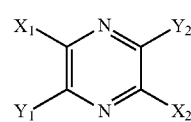

or a salt thereof; wherein
$X^1$ and $X^2$ are independently chosen from —CO(AA), —CN, —CO$_2$R$^1$, —CONR$^2$R$^3$, —COR$^4$, —NO$_2$, —SOR$^{35}$, —SO$_2$R$^6$, —SO$_2$OR$^7$ and —PO$_3$R$^8$R$^9$;
$Y^1$ and $Y^2$ are independently chosen from —OR$^{10}$, —SR$^{11}$, —NR$^{12}$R$^{13}$, —N(R$^{14}$)COR$^{15}$, —CONH(PS); —P(R$^{16}$)$_2$, —P(OR$^{17}$)$_2$ and

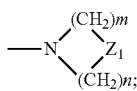

each $Z^1$ is independently chosen from a bond, $-CR^{18}R^{19}-$, $-O-$, $-NR^{20}-$, $-NCOR^{21}-$, $-S-$, $-SO-$, and $-SO_2-$, each $R^1$ to $R^{21}$ are independently chosen from hydrogen, $C_1$-$C_{10}$ alkyl optionally substituted with hydroxyl and carboxylic acid, $C_3$-$C_6$ polyhydroxylated alkyl, $C_5$-$C_{10}$ aryl, $C_5$-$C_{10}$ heteroaryl, $C_3$-$C_5$ heterocycloalkyl optionally substituted with C(O), $-(CH_2)_a CO_2 H$ optionally substituted with $C_5$-$C_{10}$ heteroaryl, $-(CH_2)_a CONR^{30}R^{31}$, $-(CH_2)_a NHSO_3^-$, $-(CH_2)_a NHSO_3 H$, $-(CH_2)_a OH$, $-(CH_2)_a OPO_3^-$, $-(CH_2)_a OPO_3 H_2$, $-(CH_2)_a OPO_3 H^-$, $-(CH_2)_a OR^{22}$, $-(CH_2)_a OSO_3^-$, $-(CH_2)_a OSO_3 H$, $-(CH_2)_a PO_3^=$, $-(CH_2)_a PO_3 H_2$, $-(CH_2)_a PO_3 H^-$, $-(CH_2)_a SO_3^-$, $-(CH_2)_a SO_3 H$, $-(CH_2)_d CO(CH_2 CH_2 O)_c R^{23}$, $-(CH_2)_d (CH_2 CH_2 O)_c R^{24}$, $-(CHCO_2 H)_a CO_2 H$, $-CH_2(CHNH_2)_a CH_2 NR^{25}R^{26}$, $-CH_2(CHOH)_a CO_2 H$, $-CH_2(CHOH)_a R^{27}$, $-CH[(CH_2)_b NH_2]_a CH_2 OH$, $-CH[(CH_2)_b NH_2]_a CO_2 H$, and $-(CH_2)_a NR^{28}R^{29}$;

each $R^{22}$ to $R^{31}$ are independently chosen from hydrogen, $C_1$-$C_{10}$ alkyl, and $C_1$-$C_5$-dicarboxylic acid;

$R^{35}$ is chosen from $C_1$-$C_{10}$ alkyl optionally substituted with hydroxyl and carboxylic acid, $C_3$-$C_6$ polyhydroxylated alkyl, $C_5$-$C_{10}$ aryl, $C_5$-$C_{10}$ heteroaryl, $C_3$-$C_5$ heterocycloalkyl optionally substituted with C(O), $-(CH_2)_a CO_2 H$ optionally substituted with $C_5$-$C_{10}$ heteroaryl, $(CH_2)_a CONR^{30}R^{31}$, $-(CH_2)_a NHSO_3^-$, $-(CH_2)_a NHSO_3 H$, $-(CH_2)_a OH$, $-(CH_2)_a OPO_3^=$, $-(CH_2)_a OPO_3 H_2$, $-(CH_2)_a OPO_3 H^-$, $(CH_2)_a OR^{22}$, $(CH_2)_a OSO_3^-$, $-(CH_2)_a OSO_3 H$, $-(CH_2)_a PO_3^=$, $-(CH_2)_a PO_3 H_2$, $-(CH_2)_a PO_3 H^-$, $-(CH_2)_a SO_3^-$, $-(CH_2)_a SO_3 H$, $-(CH_2)_d CO(CH_2 CH_2 O)_c R^{23}$, $-(CH_2)_d (CH_2 CH_2 O)_c R^{24}$, $-(CHCO_2 H)_a CO_2 H$, $-CH_2(CHNH_2)_a CH_2 NR^{25}R^{26}$, $-CH_2(CHOH)_a CO_2 H$, $-CH_2(CHOH)_a R^{27}$, $-CH[(CH_2)_b NH_2]_a CH_2 OH$, $-CH[(CH_2)_b NH_2]_a CO_2 H$, and $-(CH_2)_a NR^{28}R^{29}$;

(AA) is a polypeptide chain comprising one or more natural or unnatural amino acids linked together by peptide bonds;

(PS) is a sulfated or non-sulfated polysaccharide chain comprising one or more monosaccharide units connected by glycosidic linkages; and each 'a', 'b', and 'd' are independently chosen from 0 to 10, 'c' is chosen from 1 to 100 and each of 'm' and 'n' independently is an integer from 1 to 3;

irradiating the subject's vasculature with non-ionizing radiation, wherein the radiation causes the compound to fluoresce;

detecting the fluorescence of the compound in the subject's vasculature; and assessing the location of disease or injury in the subject's vasculature, based on the detected fluorescence.

In an embodiment, said amino acids are chosen from α-amino acids, β-amino acids, and γ-amino acids.

In certain embodiments, the composition is administered intravenously.

In certain embodiments, the non-ionizing radiation has a wavelength of at least 350 nm.

In certain embodiments, the detected fluorescence of the compound in the subject's vasculature is measured over time.

In certain embodiments, wherein the subject's pulmonary and cardiac vasculature is assessed. In some embodiments, assessing the subject's pulmonary and cardiac vasculature comprises identifying abnormalities chosen from stenosis, occlusions, aneurysms, and combinations thereof. In some embodiments, assessing the subject's pulmonary and cardiac vasculature comprises comparing the detected fluorescence in the subject's pulmonary and cardiac vasculature to that of normal pulmonary and cardiac vasculature under similar conditions. In some embodiments, wherein the subject's eye vasculature is assessed. In particular embodiments, assessing the subject's eye vasculature comprises identifying ocular abnormalities. In particular embodiments, the ocular abnormalities are chosen from blood vessel architecture, ischemic spots, choroidal infarcts, Elschnig's spots, exudates, hemorrhages, and combinations thereof. In particular embodiments, the ocular abnormalities are chosen from vessel crossovers, vessel tortuosity, evidence of exudates, and combinations thereof. In particular embodiments, assessing the subject's eye vasculature comprises comparing the detected fluorescence in the subject's eye to that of a normal eye under similar conditions.

In accordance with the present invention, one protocol for assessing physiological function of body cells includes administering an effective amount of a pyrazine derivative represented by Formula 1 into a body of a patient. An appropriate dosage of the pyrazine derivate that is administered to the patient is readily determinable by one of ordinary skill in the art and may vary according to the clinical procedure contemplated, generally ranging from about 1 nanomolar to about 100 micromolar. The administration of the pyrazine derivative to the patient may occur in any of a number of appropriate fashions including, but not limited to: (1) intravenous, intraperitoneal, or subcutaneous injection or infusion; (2) oral administration; (3) transdermal absorption through the skin; and (4) inhalation.

Still referring to the above-mentioned protocol, the pyrazine derivative is exposed to visible and/or near infrared light. This exposure of the pyrazine derivate to light may occur at any appropriate time but preferably occurs while the pyrazine derivative is in the body (e.g., in the bloodstream) of a patient. Due to this exposure of the pyrazine derivate to the visible and/or infrared light, the pyrazine derivate emanates spectral energy (e.g., visible and/or near infrared light) that may be detected by appropriate detection equipment. The spectral energy emanated from the pyrazine derivative tends to exhibit a wavelength range greater than a wavelength range absorbed by the pyrazine derivative. For example, if an embodiment of the composition absorbs light of about 700 nm, the composition may emit light of about 745 nm.

Detection of the pyrazine derivate (or more particularly, the light emanating therefrom) may be achieved through optical fluorescence, absorbance or light scattering procedures known in the art. In one embodiment, this detection of the emanated spectral energy may be characterized as a collection of the emanated spectral energy and a generation of electrical signal indicative of the collected spectral energy. The mechanism(s) utilized to detect the spectral energy from the composition that is present in the body may be designed to detect only selected wavelengths (or wavelength ranges) and/or may include one or more appropriate spectral filters. Various catheters, endoscopes, ear clips, hand bands, head bands, surface coils, finger probes and the like may be utilized to expose the pyrazine derivatives to light and/or to detect the light emanating therefrom. This detection of spectral energy may be accomplished at one or more times intermittently or may be substantially continuous.

Renal function of the patient can be determined based on the detected spectral energy using methods described in U.S. Pat. No. 9,216,963, which is hereby incorporated by reference. This can be achieved by using data indicative of the detected spectral energy and generating an intensity/time profile indicative of a clearance of the pyrazine derivative from the body. This profile may be correlated to a physiological or pathological condition. For example, the patient's clearance profiles and/or clearance rates may be compared to known clearance profiles and/or rates to assess the patient's renal function and to diagnose the patient's physiological condition. In the case of analyzing the presence of the pyrazine derivative in bodily fluids, concentration/time curves may be generated and analyzed (preferably in real time) using an appropriate microprocessor to diagnose renal function.

Physiological function can be assessed by: (1) comparing differences in manners in which normal and impaired cells remove a composition of the invention from the bloodstream; (2) measuring a rate or an accumulation of a composition of the invention in the organs or tissues; and/or (3) obtaining tomographic images of organs or tissues having a composition of the invention associated therewith. For example, blood pool clearance may be measured non-invasively from convenient surface capillaries such as those found in an ear lobe or a finger or can be measured invasively using an appropriate instrument such as an endovascular catheter. Accumulation of a composition of the invention within cells of interest can be assessed in a similar fashion.

A modified pulmonary artery catheter may also be utilized to, inter alia, make the desired measurements of spectral energy emanating from a composition of the invention. The ability for a pulmonary catheter to detect spectral energy emanating from a composition of the invention is a distinct improvement over current pulmonary artery catheters that measure only intravascular pressures, cardiac output and other derived measures of blood flow. Traditionally, critically ill patients have been managed using only the above-listed parameters, and their treatment has tended to be dependent upon intermittent blood sampling and testing for assessment of renal function. These traditional parameters provide for discontinuous data and are frequently misleading in many patient populations.

Modification of a standard pulmonary artery catheter only requires making a fiber optic sensor thereof wavelength-specific. Catheters that incorporate fiber optic technology for measuring mixed venous oxygen saturation exist currently. In one characterization, it may be said that the modified pulmonary artery catheter incorporates a wavelength-specific optical sensor into a tip of a standard pulmonary artery catheter. This wavelength-specific optical sensor can be utilized to monitor renal function-specific elimination of a designed optically detectable chemical entity such as the compositions of the present invention. Thus, by a method analogous to a dye dilution curve, real-time renal function can be monitored by the disappearance/clearance of an optically detected compound.

Disclosed herein is a method of optically diagnosing renal function in a patient, comprising the steps of:
　　administering a pyrazine derivative or a pharmaceutically-acceptable salt thereof to a patient;
　　exposing the administered pyrazine derivative to visible and/or near infrared light;
　　detecting spectral energy emanating from the administered pyrazine derivative; and
　　determining clearance of the pyrazine derivative from the body of the patient;
　　wherein the administered pyrazine derivative absorbs and emanates spectral energy in the visible and/or near infrared spectrum.

Among some of the various aspects of the present invention is the use of one or more optical dyes in a surgical procedure to enable a surgeon or other health care professional to demarcate a tissue of the renal system using methods described in U.S. Pat. No. 9,283,288, which is hereby incorporated by reference. Advantageously, the surgeon or other health care professional can thereby avoid, target and/or assess the integrity of the tissue before, during and/or after the surgical procedure.

One aspect of the present invention is directed to a process for using an optical agent in a surgical procedure. In this process, a renally excretable optical agent is administered to a patient to cause the optical agent to appear in the patient's urine. Further, a first tissue of the patient's renal system is irradiated with non-ionizing radiation, and the agent is optically detected in the irradiated first tissue to demarcate the position of the first tissue (e.g., relative to surrounding and/or adjacent tissue).

Another aspect of the invention is directed a process for using an optical agent in a surgical procedure. In this process, a surgical field of a patient is irradiated with non-ionizing radiation while a renally excretable optical agent is located in a first tissue of the patient's renal system in the surgical field. The first tissue is irradiated to detect the optical agent in the first tissue. A second tissue of the patient is then surgically manipulated based, at least in part, on the optical detection of the agent in the first tissue.

Yet another aspect of the invention is directed to a process for using an optical agent in a surgical procedure. In this process, a renally excretable optical agent is delivered to at least one tissue of a renal system of a patient, and the tissue(s) is(are) irradiated with non-ionizing radiation. The optical agent is detected (based, at least in part, on irradiation of the tissue) to determine if the agent is retained within the tissue(s) of the renal system of the patient.

Disclosed herein is a process for using a fluorescent agent in an abdominal or pelvic surgical procedure to reduce the risk of accidental injury to a ureter of a patient undergoing an abdominal or pelvic surgical procedure, the process comprising:
　　delivering a fluorescent agent to the ureter of a patient undergoing an abdominal or pelvic surgical procedure,
　　wherein the fluorescent agent is delivered intravenously, enterally, intraperitoneally, transdermally, or via inhalation to the patient,
　　wherein at least a fraction of the fluorescent agent is excreted through the renal system such that at least a fraction of the fluorescent agent is present in the patient's urine,
　　wherein the fluorescent agent is chosen from phenylxanthenes, phenothiazines, phenoselenazines, cyanines, indocyanines, squaraines, dipyrrolo pyrimidones, anthraquinones, tetracenes, quinolines, pyrazines, acridines, acridones, phenanthridines, azo dyes, rhodamines, phenoxazines, azulenes, azaazulenes, triphenyl methane dyes, indoles, benzoindoles, indocarbocyanines, benzoindocarbocyanines, derivatives having the general structure of 4,4-difluoro-4-bora-3a,4a-diaza-s-indacene, and conjugates thereof and derivatives thereof, irradiating a ureter of the patient's renal system with non-ionizing radiation to cause the fluorescent agent to fluoresce within the ureter; and optically detecting the fluorescent agent in the irradiated ureter to distinguish the ureter from surrounding tissues and reduce the risk of accidental injury to the ureter.

Kits

The present disclosure provides a kit for assessing vasculature, diagnosing renal function, or using a fluorescent agent in an abdominal or pelvic surgical procedure to reduce the risk of accidental injury to a ureter of a patient in a subject in need thereof, comprising: a compound of structural Formula I

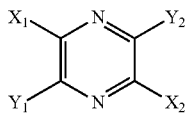

or a salt thereof; wherein or a salt thereof;

$X^1$ and $X^2$ are independently chosen from —CO(AA), —CN, —CO$_2$R$^1$, —CONR$^2$R$^3$, —COR$^4$, —NO$_2$, —SOR$^{35}$, —SO$_2$R$^6$, —SO$_2$OR$^7$ and —PO$_3$R$^8$R$^9$;

$Y^1$ and $Y^2$ are independently chosen from —OR$^{10}$, —SR$^{11}$, —NR$^{12}$R$^{13}$, —N(R$^{14}$)COR$^{15}$, —CONH(PS); —P(R$^{16}$)$_2$, —P(OR$^7$)$_2$ and

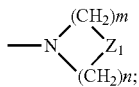

each $Z^1$ is independently chosen from a bond, —CR$^{18}$R$^{19}$—, —O—, —NR$^{20}$—, —NCOR$^{21}$—, —S—, —SO—, and —SO$_2$—;

each R$^1$ to R$^{21}$ are independently chosen from hydrogen, C$_1$-C$_{10}$ alkyl optionally substituted with hydroxyl and carboxylic acid, C$_3$-C$_6$ polyhydroxylated alkyl, C$_5$-C$_{10}$ aryl, C$_5$-C$_{10}$ heteroaryl, C$_3$-C$_5$ heterocycloalkyl optionally substituted with C(O), —(CH$_2$)$_a$CO$_2$H optionally substituted with C$_5$-C$_{10}$ heteroaryl, —(CH$_2$)$_a$CONR$^{30}$R$^{31}$, —(CH$_2$)$_a$NHSO$_3^-$, —(CH$_2$)$_a$NHSO$_3$H, —(CH$_2$)$_a$OH, —(CH$_2$)$_a$OPO$_3^=$, —(CH$_2$)$_a$OPO$_3$H$_2$, —(CH$_2$)$_a$OPO$_3$H$^-$, —(CH$_2$)$_a$OR$^{22}$, —(CH$_2$)$_a$OSO$_3^-$, —(CH$_2$)$_a$OSO$_3$H, —(CH$_2$)$_a$PO$_3^=$, —(CH$_2$)$_a$PO$_3$H$_2$, —(CH$_2$)$_a$PO$_3$H$^-$, —(CH$_2$)$_a$SO$_3^-$, —(CH$_2$)$_a$SO$_3$H, —(CH$_2$)$_d$CO(CH$_2$CH$_2$O)$_c$R$_{23}$, —(CH$_2$)$_d$(CH$_2$CH$_2$O)$_c$R$^{24}$, (CHCO$_2$H)$_a$CO$_2$H, —CH$_2$(CHNH$_2$)$_a$CH$_2$NR$^{25}$R$^{26}$, —CH$_2$(CHOH)$_a$CO$_2$H, —CH$_2$(CHOH)$_a$R$^{27}$, —CH[(CH$_2$)$_b$NH$_2$]$_a$CH$_2$OH, —CH[(CH$_2$)$_b$NH$_2$]$_a$CO$_2$H, and —(CH$_2$)$_a$NR$^{28}$R$^{29}$;

each R$^{22}$ to R$^{31}$ are independently chosen from hydrogen, C$_1$-C$_{10}$ alkyl, and C$_1$-C$_5$-dicarboxylic acid;

R$^{35}$ is chosen from C$_1$-C$_{10}$ alkyl optionally substituted with hydroxyl and carboxylic acid, C$_3$-C$_6$ polyhydroxylated alkyl, C$_5$-C$_{10}$ aryl, C$_5$-C$_{10}$ heteroaryl, C$_3$-C$_5$ heterocycloalkyl optionally substituted with C(O), —(CH$_2$)$_a$CO$_2$H optionally substituted with C$_5$-C$_{10}$ heteroaryl, —(CH$_2$)$_a$CONR$^3$R$^{31}$, —(CH$_2$)$_a$NHSO$_3^-$, —(CH$_2$)$_a$NHSO$_3$H, —(CH$_2$)$_a$OH, —(CH$_2$)$_a$OPO$_3^=$, —(CH$_2$)$_a$OPO$_3$H$_2$, —(CH$_2$)$_a$OPO$_3$H$^-$, —(CH$_2$)$_a$OR$^{22}$, —(CH$_2$)$_a$OSO$_3$, —(CH$_2$)$_a$OSO$_3$H, —(CH$_2$)$_a$PO$_3^=$, —(CH$_2$)$_a$PO$_3$H$_2$, —(CH$_2$)$_a$PO$_3$H$^-$, —(CH$_2$)$_a$SO$_3^-$, —(CH$_2$)$_a$SO$_3$H, —(CH$_2$)$_d$CO(CH$_2$CH$_2$O)$_c$R$^{23}$, —(CH$_2$)$_d$(CH$_2$CH$_2$O)$_c$R$^{24}$, —(CHCO$_2$H)$_a$CO$_2$H, —CH$_2$(CHNH$_2$)$_a$CH$_2$NR$^{25}$R$^{26}$, —CH$_2$(CHOH)$_a$ CO$_2$H, —CH$_2$(CHOH)$_a$R$^{27}$, —CH[(CH$_2$)$_b$NH$_2$]$_a$CH$_2$OH, —CH[(CH$_2$)$_b$NH$_2$]$_a$CO$_2$H, and —(CH$_2$)$_a$NR$^{28}$R$^{29}$;

(AA) is a polypeptide chain comprising one or more natural or unnatural amino acids linked together by peptide bonds;

(PS) is a sulfated or non-sulfated polysaccharide chain comprising one or more monosaccharide units connected by glycosidic linkages; and each 'a', 'b', and 'd' are independently chosen from 0 to 10, 'c' is chosen from 1 to 100 and each of 'm' and 'n' independently is an integer from 1 to 3; and written instructions for assessing the vasculature in the subject, comprising the steps of:

administering an effective amount of the compound of structural Formula I;

irradiating the subject's vasculature with non-ionizing radiation, wherein the radiation causes the compound to fluoresce;

detecting the fluorescence of the compound in the subject's vasculature; and visualizing the vasculature within the subject based on the detected fluorescence.

In an embodiment, said amino acids are chosen from α-amino acids, β-amino acids, and γ-amino acids.

In certain embodiments, the instructions include a step for administering the compound intravenously.

In certain embodiments, the instructions include a step for irradiating the composition with the non-ionizing radiation having a wavelength of at least 350 nm.

In certain embodiments, the instructions include a step for measuring the detected fluorescence of the compound in the subject's vasculature over time.

In certain embodiments, the subject's pulmonary and cardiac vasculature is assessed.

In certain embodiments, the instructions include a step for assessing the subject's pulmonary and cardiac vasculature comprising identifying abnormalities chosen from stenosis, occlusions, aneurysms, and combinations thereof In certain embodiments, the instructions include a step for assessing the subject's pulmonary and cardiac vasculature comprising comparing the detected fluorescence in the subject's pulmonary and cardiac vasculature to that of normal pulmonary and cardiac vasculature under similar conditions.

In certain embodiments, the instructions include a step for the subject's eye vasculature to be assessed.

In certain embodiments, the instructions include a step for assessing the subject's eye vasculature comprises identifying ocular characteristics. In particular embodiments, the ocular characteristics are chosen from blood vessel architecture, ischemic spots, choroidal infarcts, Elschnig's spots, exudates, hemorrhages, and combinations thereof. In particular embodiments, the ocular characteristics are chosen from vessel crossovers, vessel tortuosity, evidence of exudates, and combinations thereof.

In certain embodiments, the instructions include a step for assessing the subject's eye vasculature comprises comparing the detected fluorescence in the subject's eye to that of a normal eye under similar conditions.

Formulation

The compositions of the present disclosure may be administered intravenously, intraperitoneally, or via subcutaneous injection or infusion; so that the compound enters the bloodstream.

Pyrazine derivatives of this invention can be administered as solutions in most pharmaceutically acceptable intravenous vehicles known in the art. Pharmaceutically acceptable vehicles that are well known to those skilled in the art include, but are not limited to, 0.01-0.1 M phosphate buffer or 0.8% saline. Additionally, pharmaceutically acceptable carriers may be aqueous or non-aqueous solutions, suspensions, emulsions, or appropriate combinations thereof. Examples of non-aqueous solvents are propylene glycol, polyethylene glycol, vegetable oils such as olive oil, and injectable organic esters such as ethyl oleate. Examples of aqueous carriers are water, alcoholic/aqueous solutions, emulsions or suspensions, including saline and buffered media. Exemplary parenteral vehicles include sodium chloride solution, Ringer's dextrose, dextrose and sodium chloride, lactated Ringer's or fixed oils. Exemplary intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Dosage

Compositions of the present disclosure may be administered in a single dose or in multiple doses to achieve an effective diagnostic objective. After administration, the composition is allowed time to move into the eye, and the selected target site is exposed to light with a sufficient power and intensity to detect light emanating from the compound within the patient's body to provide information that may be utilized by a healthcare provider (e.g., in making a diagnosis). Doses may vary widely depending upon, for example, the particular integrated photoactive agent employed, the areas (e.g., organs or tissues) to be examined, the equipment employed in the clinical procedure, the efficacy of the treatment achieved, and/or the like. For example, the dosage of the compound may vary from about 0.1 mg/kg body weight to about 500 mg/kg body weight in some embodiments. In other embodiments, the dosage of the compound may vary from about 0.5 to about 2 mg/kg body weight.

Detection and Measurement

For detection of vasculature, after administration, the composition is allowed time to move into the eye, and the selected target site is exposed to light with a sufficient power and intensity to detect light emanating from the compound within the patient's body to provide information that may be utilized by a healthcare provider (e.g., in making a diagnosis). Detection of the composition may be achieved by optical fluorescence, absorbance, and/or light scattering methods. This detection of spectral energy may be accomplished at one or more times intermittently or may be substantially continuous.

In an embodiment, the process of the present invention can be used to enable the surgeon or other healthcare individual to avoid the ureter(s), the bladder, and/or the urethra. In a healthy individual, urine flows from the kidneys through the ureter and collects in the bladder, where it is stored until it is eliminated from the body through the urethra. Thus, in the process of the present invention, detection of the optical agent(s) in the ureter and bladder is possible due to the accumulation of the agent(s) in urine present in those structures. Detection of the optical agent(s) in the urethra is possible, for example, where residue of urine containing the optical agents is present on the walls of the urethra, or where a urinary catheter facilitates continuous flow of urine through the urethra.

Alternatively, another aspect of the present invention is the use of one or more optical agents to demarcate the target of a surgical procedure. Such surgical procedures include, but are not limited to, for example, nephrectomy, renal transplantation surgery, resection of a ureteral segment during removal of a tumor, bladder neck suspension surgery, and surgical removal of kidney stones.

A further aspect of the present invention is the use of the optical agent(s) to assess the integrity of the renal system. Such an assessment can be made before, during, and/or after a surgical procedure performed on the renal system and/or other organ and/or tissue in the abdominal and/or pelvic region. Confinement of the optical agent to the tissues of the renal system indicates that no damage to the renal system (e.g., nicking of the ureter) has occurred. If damage or injury to a tissue of the renal system has occurred, the process of the present invention allows a surgeon to rapidly identify the location of such damage or injury (e.g., by observing the egress of dye from the site of damage).

A further aspect of the present invention is the use of the optical agent(s) to detect one or more tissues of the renal system during a diagnostic laparoscopic procedure.

Depending upon the surgical technique employed, the presence of the optical agent in a first tissue may be detected by irradiating the entire surgical field. This approach could be used, for example, in open surgical procedures. Alternatively, only a portion of the surgical field or the specific site(s) to be monitored may be illuminated, for example, using a laparoscope or other endoscopic tool.

In general, any source of irradiation capable of providing non-ionizing radiation of a desired wavelength may be used. For example, in one embodiment, the operating room lighting (e.g., fluorescent or incandescent lighting) emits light of the desired wavelength. In another embodiment, the source of irradiation is a laser. In yet another embodiment, the source of irradiation is a hand-held light. Other sources of irradiation that can be used include, but are not limited to, lighted catheters, endoscopes, fiber optic probes, light emitting diodes (LEDs), lighted headbands (also called headlights), and the like. A surgical instrument that contains or is configured with an illumination system may also be employed. Examples of such instruments include the fiber optic instruments available from BioSpec (Moscow, Russia) and the TC-I fiber optic tool for photodynamic therapy with fine needle tip for irradiating interstitial tumors (http://www.biospec.ru/_Fiber_Optics_e.html).

Any of the optical detection methods available in the art can be used in the present invention. Spectroscopic measurements can be separated into three broad categories: absorbance, scattering/reflectance, and emission. Absorbance assays involve relating the amount of incident light that is absorbed by a sample to the type and number of molecules in the sample. For example, in case of absorbance measurement, it is desirable that the wavelength of the non-ionizing radiation that is used is one which is absorbed by the optical agent. Most commonly, absorbance is measured indirectly by studying the portion of incident light that emerges from the sample. Scattering assays are similar to absorbance in that the measurement is based on the amount of incident light that emerges or is transmitted from the sample or tissue. However, in the case of scattering, the signal increases with the number of interactions, whereas, in the case of absorbance, the signal is inversely proportional to the interactions. Emission assays look at electromagnetic emissions from a sample other than the incident light. In each case, the measurements may be broad spectrum or frequency-specific depending on the particular assay. Most commonly, emission assays involve the measurement of luminescence.

Luminescence is the emission of light from excited electronic states of atoms or molecules. Luminescence generally refers to all kinds of light emission, except incandescence, and may include photoluminescence, chemiluminescence, and electrochemiluminescence, among others. In photoluminescence, including fluorescence and phosphorescence, the excited electronic state is created by the absorption of electromagnetic radiation. Luminescence assays involve detection and interpretation of one or more properties of the luminescence or associated luminescence process. These properties include intensity, excitation and/or emission spectrum, polarization, lifetime, and energy transfer, among others. These properties also include time-independent (steady-state) and/or time-dependent (time-resolved) properties of the luminescence. Representative luminescence assays include fluorescence intensity (FLINT), fluorescence polarization (FP), fluorescence resonance energy transfer (FRET), fluorescence lifetime (FLT), total internal reflection fluorescence (TIRF), fluorescence correlation spectroscopy (FCS), fluorescence recovery after photobleaching (FRAP), and bioluminescence resonance energy transfer (BRET), among others. By way of example, when a fluorescent optical agent is used in the present invention, it is desirable that the wavelength of non-ionizing radiation be such that it excites the optical agent. This excitation causes the molecule to emit part of the absorbed energy at a different wavelength, and the emission can be detected using fluorometric techniques as described above. One skilled in the art can readily determine the most appropriate detection technique based on, in part, the specific optical agent(s) administered, the tissue to be detected, and the type of surgical procedure involved. For example, in some embodiments, the surgeon will be able to see the optical agent in the surgical field. Other embodiments employ an optical agent that can be detected using a laparoscopic instrument.

Upon irradiation with electromagnetic radiation of the proper wavelength, an optical agent may be detected by visual or other optical means. For example, optical detection may be achieved using the unaided eye or by one or more imaging or detecting devices (e.g., a camera, charged coupled device (CCD), photomultiplier tube (PMT), avalanche diode, photodiodes), or detection involving an electronic processing step (e.g., detecting, enhancing, processing, analyzing, quantitating, or otherwise manipulating a signal using software or other means).

In order that the disclosure described herein may be more fully understood, the following examples are set forth. It should be understood that these examples are for illustrative purposes only and are not to be construed as limiting this disclosure in any manner.

EXAMPLES

Non-limiting examples of methods utilizing pyrazine dyes include the following compounds and pharmaceutically acceptable salts thereof:

Example 1: Assessing Eye Vasculature

An exemplary procedure for assessing eye vasculature is as follows: a composition containing a fluorescent pyrazine molecule is administered into a subject's bloodstream. While in the blood stream, the fluorescent dye molecule may be irradiated with non-ionizing radiation, wherein the radiation causes the composition to fluoresce. The fluorescence of any absorbed challenge molecule may be detected in the bloodstream; and the eye vasculature may be assessed based on the detected fluorescence.

Yet another exemplary procedure may be performed as described above, but in addition, the fluorescence of the fluorescent pyrazine molecule may be detected in the eye over time; and the location of disease or injury in the subject's eye may be determined based on the time between the detected fluorescence of each fluorescent challenge molecule and administration.

Example 2: 3,6-diamino-$N^2$,$N^5$-bis(D-serine)-pyrazine-2,5-dicarboxamide

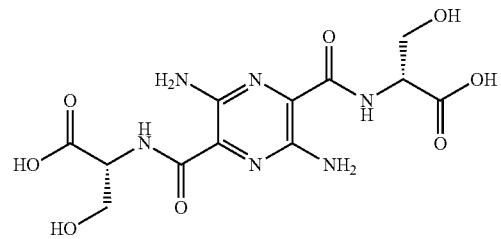 [SMILES: Nc1nc(C(=O)N[C@H](CO)C(=O)O)c(N)nc1C(=O)N[C@H](CO)C(=O)O]

This fluorescent molecule exhibits light absorption and emission maxima at 445 nm and 560 nm, respectively; and is an example of a fluorescent pyrazine molecule that may used to assess and/or visualize the vasculature of a subject.

Step 1. Synthesis of 3,6-diamino-$N^2$,$N^5$-bis(O-benzyl-(D)-serine methyl ester)-pyrazine-2,5-dicarboxamide

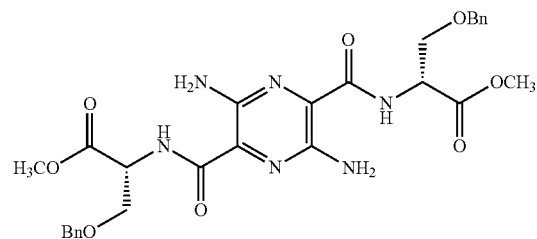 [SMILES: COC(=O)[C@@H](COCc1ccccc1)NC(=O)c1nc(N)c(C(=O)N[C@H](COCc2ccccc2)C(=O)OC)nc1N]

A mixture of sodium 3,6-diaminopyrazine-2,5-dicarboxylate (300 mg, 1.24 mmol), (D)-Ser(OBn)-OMe-HCl salt (647 mg, 2.64 mmol), HOBt-$H_2O$ (570 mg, 3.72 mmol) and EDC-HCl (690 mg, 3.60 mmol) in DMF (25 mL) was treated with TEA (2 mL). The resulting mixture was stirred for 16 h and concentrated. The mixture was concentrated to dryness and the residue was partitioned with EtOAc and water. The layers were separated and the EtOAc solution was washed with saturated $NaHCO_3$ and brine. The solution was dried over anhydrous $Na_2SO_4$, filtered and concentrated, which afforded 370 mg (51% yield) of the bisamide as a bright yellow powder: $^1$NMR (300 MHz, $CDCl_3$) δ 8.47 (d, J=8.74 Hz, 2H), 7.25-7.37 (complex m, 10H), 5.98 (bs, 4H), 4.85 (dt, J=8.7, 3.3 Hz, 2H), 4.56 (ABq, J=12.6, Hz, Av=11.9 Hz, 4H), 3.99 (one half of an ABq of d, J=8.7, 3.3, Av obscured, 2H), 3.76-3.80 (one half of an ABq-obscured, 2H), 3.78 (s, 6H). $^{13}$C NMR (75 MHz, $CDCl_3$) δ 170.5 (s), 165.1 (s), 146.8 (s), 138.7 (s) 128.6 (d), 128.1 (d), 127.8 (d), 126.9 (s), 73.5 (t), 69.8 (t), 53.0 (q), 52.9 (q). LCMS (5-95% gradient acetonitrile with 0.1% TFA over 10 min), single peak retention time=4.93 min on 30 mm column, (M+H)⁺=581.

Step 2. Synthesis of 3,6-diamino-N²,N⁵-bis(O-benzyl-(D)-serine)-pyrazine-2,5-dicarboxamide

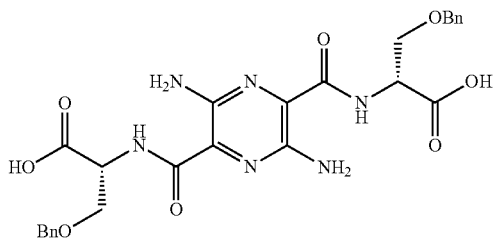 [SMILES: Nc1nc(C(=O)N[C@H](COCc2ccccc2)C(=O)O)c(N)nc1C(=O)N[C@H](COCc1ccccc1)C(=O)O]

The product from Step 1 (370 mg, 0.64 mmol) in THF (10 mL) was treated with 1.0 N sodium hydroxide (2.5 mL). After stirring at room temperature for 30 min, the reaction was judged complete by TLC. The pH was adjusted to approximately 2 by the addition of 1.0 N HCl and the resulting solution was extracted (3×) with EtOAc. The layers were combined, dried over sodium sulfate, filtered and concentrated to afford 353 mg (100% yield) of the di-acid as an orange foam: LCMS (5-95% gradient acetonitrile in 0.1% TFA over 10 min), retention time=4.41 min on 30 mm column, (M+H)⁺=553.

Step 3. Synthesis of 3,6-diamino-N²,N⁵-bis(D-serine)-pyrazine-2,5-dicarboxamide

To the product from Step 2 (353 mg, 0.64 mmol) in methanol (20 mL) was added 5% Pd/C (300 mg) and ammonium formate (600 mg). The resulting reaction was heated at reflux for 2 h. The reaction was cooled to room temperature, filtered through a plug of celite and concentrated. The residue was recrystallized from methanol-ether to provide 191 mg (80% yield) of title compound Example 2 as a yellow foam: ¹NMR (300 MHz, DMSO-d₆) δ 8.48 (d, J=6.9 Hz, 2H), 6.72 (bs, 4H), 3.95 (apparent quartet, J=5.1 Hz, 2H), 3.60 (apparent ABq of doublets; down-field group centered at 3.71, J=9.9, 5.1 Hz, 2H; up-field group centered at 3.48, J=20 9.9, 6.3 Hz, 2H). ¹³C NMR (75 MHz, CDCl₃) δ 172.9 (s), 164.9 (s), 147.0 (s), 127.0 (s), 62.9 (d), 55.7 (t). LCMS (5-95% gradient acetonitrile in 0.1% TFA over 10 min), single peak retention time=1.45 min on 30 mm column, (M+H)⁺=373. UV/vis (100 μM in PBS) λ$_{abs}$=434 nm. Fluorescence λ$_{ex}$⁻449 nm, λ$_{em}$=559 nm.

Example 3: 3,6-diamino-N²,N⁵-bis(L-serine)-pyrazine-2,5-dicarboxamide

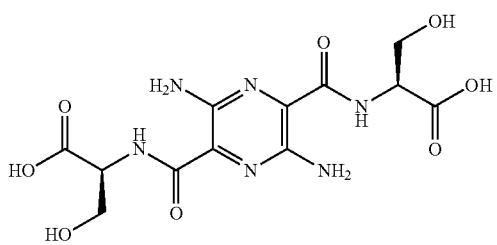 [SMILES: Nc1nc(C(=O)N[C@@H](CO)C(=O)O)c(N)nc1C(=O)N[C@@H](CO)C(=O)O]

The title compound is prepared using the procedures of Example 2 and substituting (L)-Ser(OBn)-OMe-HCl salt for (D)-Ser(OBn)-OMe-HCl salt in Step 1. RP-LC/MS (ESI) m/z 373.2 (M+H)⁺. Anal. Calcd for C₁₂H₁₆N₆O₈: C, 38.71; H, 4.33; N, 22.57. Found: C, 38.44; H, 4.51; N, 22.33.

This fluorescent molecule exhibits light absorption and emission maxima at 445 nm and 560 nm, respectively.

Example 4: 3,6-diamino-N²,N²,N⁵,N⁵-tetrakis(2-methoxyethyl) pyrazine-2,5-dicarboxamide

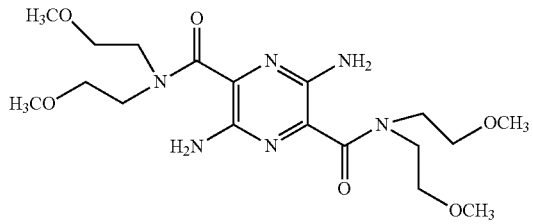 [SMILES: COCCN(CCOC)C(=O)c1nc(N)c(C(=O)N(CCOC)CCOC)nc1N]

A mixture of 3,6-diaminopyrazine-2,5-dicarboxylic acid (200 mg, 1.01 mmol), bis-2-(methoxyethyl) amine (372 mL, 335.5 mg, 2.52 mmol), HOBt-H₂O (459 mg, 3.00 mmol), and EDC-HCl (575 mg, 3.00 mmol) were stirred together in DMF (20 mL) for 1 h at room temperature. The mixture was concentrated to dryness and the residue was partitioned with EtOAc and water. The layers were separated and the EtOAc solution was washed with saturated NaHCO₃ and brine. The solution was dried over anhydrous Na₂SO₄, filtered and concentrated. Purification by radial flash chromatography (SiO₂, 10/1 CHCl₃-MeOH) afforded 228.7 mg (53% yield) of Example 4 as an orange foam: ¹H NMR (300 MHz, CDCl₃), δ 4.92 (s, 4H), 3.76 (apparent t, J=5.4 Hz, 4H), 3.70 (apparent t, J=5.6 Hz, 4H), 3.64 (apparent t, J=5.4 Hz, 4H), 3.565 (apparent t, J=5.4 Hz), 3.67 (s, 6H), 3.28 (s, 6H). ¹³C NMR (75 MHz, CDCL3) ☐ 167.6 (s), 145.6 (s), 131.0 (s), 72.0 (t), 70.8 (t), 59.2 (q), 49.7 (t), 47.1 (t). LCMS (5-95% gradient acetonitrile in 0.1% TFA over 10 min), single peak retention time=3.14 min on 30 mm column, (M+H)⁺=429. UV/vis (100 μM in PBS) λ$_{abs}$=394 nm. Fluorescence (100 μm) λ$_{ex}$=394 nm λ$_{em}$=550 nm.

Example 5: 3,6-diamino-N²,N⁵-bis (2,3-dihydroxypropyl) pyrazine-2,5-dicarboxamide

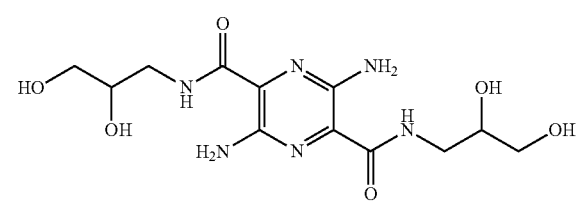 [SMILES: Nc1nc(C(=O)NCC(O)CO)c(N)nc1C(=O)NCC(O)CO]

Step 1. Synthesis of 3,6-diamino-$N^2,N^5$-bis((2,2-dimethyl-1,3-dioxolan-4-yl)methyl) pyrazine-2,5-dicarboxamide

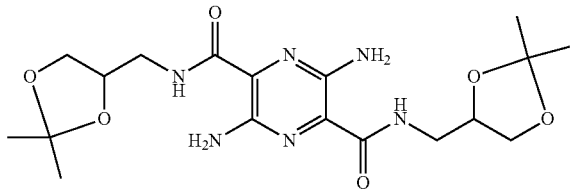

A mixture of 3,6-diaminopyrazine-2,5-dicarboxylic acid (350 mg, 1.77 mmol), racemic (2,2-dimethyl-1,3-dioxolan-4-yl)methanamine (933 µL, 944 mg, 7.20 mmol), HOBt-$H_2O$ (812 mg, 5.3 mmol), and EDC-HCl (1.02 g, 5.32 mmol) were stirred together in DMF (20 mL) for 16 h at room temperature. The mixture was concentrated to dryness and the residue was partitioned with EtOAc and water. The layers were separated and the EtOAc solution was washed with saturated $NaHCO_3$ and brine. The solution was dried over anhydrous $Na_2SO_4$, filtered and concentrated to afford 665 mg (88% yield) of the bis-amide diastereomeric pair as a yellow solid: $^1$NMR (300 MHz, $CDCl_3$) δ 8.38 (t, J=5.8 Hz, 2H), 6.55 (s, 4H), 4.21 (quintet, J=5.8 Hz, 2H), 3.98 (dd, J=8.4 Hz, 6.3 Hz, 2H), 3.65 (dd, J=8.4 Hz, J=5.8 Hz, 2H), 3.39 (apparent quartet-diastereotopic mixture, J=5.9 Hz, 4H), 1.35 (s, 6H), 1.26 (s, 6H). $^{13}$C NMR (75 MHz, $CDCl_3$) δ 165.7 (s), 146.8 (s), 126.8 (s), 109.2 (s), 74.8 (d), 67.2 (t), 42.2, 41.1 (t-diastereotopic pair), 27.6 (q), 26.1 (q).

Step 2. Synthesis of 3,6-diamino-$N^2,N^5$-bis(2,3-dihydroxypropyl) pyrazine-2,5-dicarboxamide The product from Step 1 was dissolved in THF (100 mL) and treated with 1.0 N HCl (2 mL). After hydrolysis was complete, the mixture was treated with $K_2CO_3$ (1 g) and stirred for 1 h and filtered through a plug of $C_{18}$ silica using methanol. The filtrate was concentrated to dryness and the residue was triturated with MeOH (50 mL). The solids were filtered and discarded and the residue was treated with ether (50 mL). The precipitate was collected by filtration and dried at high vacuum. This material was purified by radial flash chromatography to afford 221 mg (36% yield) of Example 5 as an orange solid: $^1$NMR (300 MHz, DMSO-$d_6$) δ 8.00 (bm, 6H), 5.39 (bs, 2H), 4.88 (bs, 2H), 3.63-3.71 (complex m, 2H), 3.40 (dd, J=11.1, 5.10 Hz, 2H), 3.28 (dd, J=11.1, 6.60 Hz, 2H), 2.92 (dd, J=12.6, 3.3 Hz, 2H), 2.65 (dd, J=12.6, 8.4 Hz, 2H). LCMS (5-95% gradient acetonitrile in 0.1% TFA over 10 min), single peak retention time=4.13 min on 30 mm column, (M+H)$^+$=345. UV/vis (100 µM in $H_2O$) $\lambda_{abs}$=432 nm. Fluorescence $\lambda_{ex}$=432 nm, $\lambda_{em}$=558 nm.

Example 6: 3,6-bis(bis(2-methoxyethyl)amino-$N^2,N^2,N^5,N^5$-tetrakis(2-methoxyethyl) pyrazine-2,5-dicarboxamide bis TFA Salt

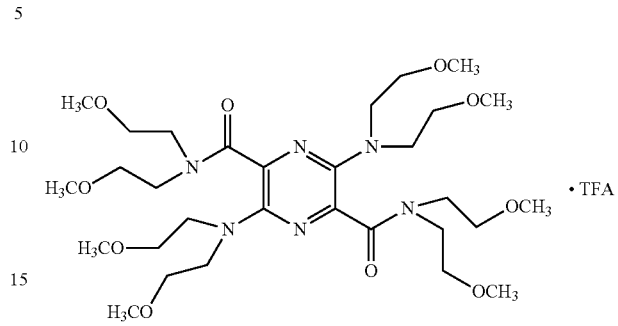

Step 1. Synthesis of 3,6-dibromopyrazine-2,5-dicarboxylic Acid

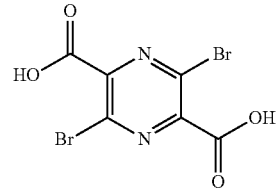 [SMILES: O=C(O)c1nc(Br)c(C(=O)O)nc1Br]

3,6-Diaminopyrazine-2,5-dicarboxylic acid (499 mg, 2.52 mmol) was dissolved in 48% hydrobromic acid (10 mL) and cooled to 0° C. in an ice-salt bath. To this stirred mixture was added a solution of sodium nitrite (695 mg, 10.1 mmol) in water (10 mL) dropwise so that the temperature remains below 5° C. The resulting mixture was stirred for 3 h at 5-15° C., during which time the red mixture became a yellow solution. The yellow solution was poured into a solution of cupric bromide (2.23 g, 10.1 mmol) in water (100 mL) and the resulting mixture was stirred at room temperature. After an additional 3 h, the aqueous mixture was extracted with EtOAc (3×). The combined extracts were dried ($Na_2SO_4$), filtered and concentrated to afford 440 mg (54% yield) 3,6-dibromopyrazine-2,5-dicarboxylic acid as a pale yellow solid: $^{13}$C NMR (75 MHz, $CDCl_3$) δ 164.3 (s), 148.8 (s), 134.9 (s). HPLC (5-95% gradient acetonitrile in 0.1% TFA over 10 min), single peak retention time=2.95 min on 250 mm column.

Step 2. Synthesis of 3-(Bis(2-methoxyethyl)amino)-6-bromo-$N^2,N^2,N^5,N^5$-tetrakis(2-methoxyethyl) pyrazine-2,5-dicarboxamide

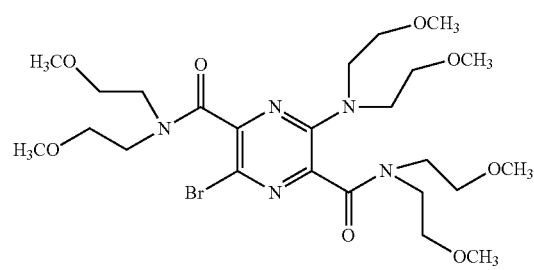 [SMILES: COCCN(CCOC)C(=O)c1nc(N(CCOC)CCOC)c(C(=O)N(CCOC)CCOC)nc1Br]

The product from step 1 (440 mg, 1.36 mmol) was dissolved in DMF (25 mL), treated with HOBt-$H_2O$ (624 mg, 4.08 mmol), and EDC-HCl (786 mg, 4.10 mmol) and stirred for 30 min at 5 room temperature. Bis(2-methoxyethyl) amine (620 mL, 559 mg, 4.20 mmol) was added and the resulting mixture was stirred at room temperature for 16 h and concentrated. The residue was partitioned with water and EtOAc. The EtOAc layer was separated and the aqueous was extracted again with EtOAc. The combined organic layers were washed with 0.5 N HCl, saturated sodium bicarbonate, and brine. The organic layer was dried (Na$_2$SO$_4$), filtered and concentrated to afford 214 mg of 3-(bis(2-methoxyethyl)amino)-6-bromo-N$_2$,N$_2$,N$_5$,N$_5$-tetrakis(2-methoxyethyl) pyrazine-2,5-dicarboxamide (26% yield) as a brown oil: LCMS (5-95% gradient acetonitrile in 0.1% TFA over 10 min), single peak retention time=3.85 min on 30 mm column, (M+H)+=608.

Step 3. Synthesis of 3,6-bis(bis(2-methoxyethyl)amino-N$^2$,N$^2$,N$^5$,N$^5$-tetrakis(2-methoxyethyl)pyrazine-2,5-dicarboxamide bis TFA Salt

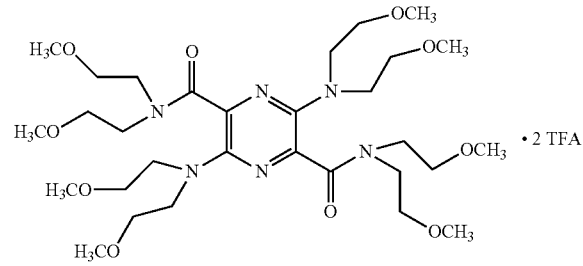 [SMILES: COCCN(CCOC)C(=O)c1nc(N(CCOC)CCOC)c(C(=O)N(CCOC)CCOC)nc1N(CCOC)CCOC]

To the product from step 2 (116 mg, 0.19 mmol) was added bis(2-methoxylethyl)amine (3.0 mL, 2.71 g, 20.3 mmol) and a "spatula tip" of Pd(PPh$_3$)$_4$. The resulting mixture was heated to 140° C. for 2 h. The reaction was cooled and concentrated. The residue was purified by flash chromatography (SiO$_2$, 10/1 CHCl$_3$-MeOH). The resulting material was purified again by reverse phase medium pressure reverse phase chromatography (C18, 10-50% manual gradient acetonitrile in 0.1% TFA) to afford 12 mg (10% yield) of Example 6 as an orange-brown film: LCMS (15-95% gradient acetonitrile in 0.1% TFA over 10 min), single peak retention time=3.85 min on 250 mm column, (M+H)+=661. UV/vis (100 μM in PBS) λ$_{abs}$=434 nm. Fluorescence λ$_{ex}$=449 nm, λ$_{em}$=559 nm.

Example 7: 3,6-diamino-N$^2$,N$^5$-bis(2-aminoethyl) pyrazine-2,5-dicarboxamide Bis TFA Salt

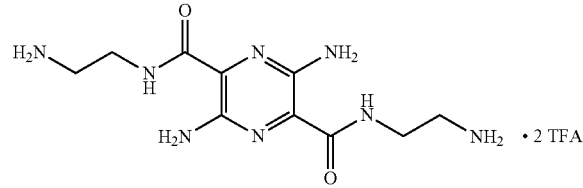 [SMILES: NCCNC(=O)c1nc(N)c(C(=O)NCCN)nc1N]

Step 1. Synthesis of 3,6-diamino-N$^2$,N$^5$-bis[2-(tert-butoxycarbonyl)aminoethyl]pyrazine-2,5-dicarboxamide

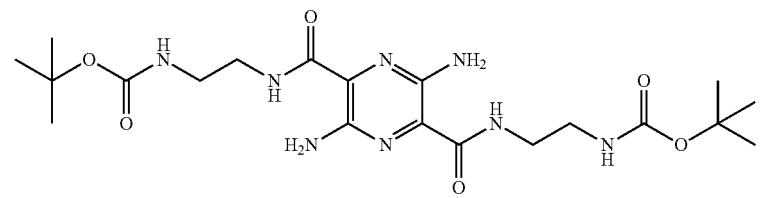 [SMILES: CC(C)(C)OC(=O)NCCNC(=O)c1nc(N)c(C(=O)NCCNC(=O)OC(C)(C)C)nc1N]

A mixture of sodium 3,6-diaminopyrazine-2,5-dicarboxylate (500 mg, 2.07 mmol), tert-butyl 2-aminomethylcarbamate (673 mg, 4.20 mmol), HOBt-H$_2$O (836 mg, 5.46 mmol) and EDC-HCl (1.05 g, 5.48 mmol) in DMF (25 mL) was stirred for 16 h and concentrated. Work up as in Example 2 afforded 770 mg (76% yield) of the bisamide as an orange foam: $^1$NMR (300 MHz, DMSO-d$^6$) major comformer, δ 8.44 (t, J=5.7 Hz, 2H), 6.90 (t, J=5.7 Hz, 2H), 6.48 (bs, 4H), 2.93-3.16 (complex m, 8H), 1.37 (s, 9H), 1.36 (s, 9H). $^{13}$C NMR (75 MHz, DMSO-d6), conformational isomers δ 165.1 (s), 155.5 (bs), 155.4 (bs), 146.0 (s), 126.2 (s), 77.7 (bs), 77.5 (bs), 45.2 (bt), 44.5 (bt). 28.2 (q).

Step 2. Synthesis of 3,6-diamino-N$^2$,N$^5$-bis(2-aminoethyl)pyrazine-2,5-dicarboxamide bis TFA Salt To the product from step 1 (770 mg, 1.60 mmol) in methylene chloride (100 mL) was added TFA (25 mL) and the reaction was stirred at room temperature for 2 h. The mixture was concentrated and the residue taken up into methanol (15 mL). ether (200 mL) was added and the orange solid precipitate was isolated by filtration and dried at high vacuum to afford 627 mg (77% yield) of Example 7 as an orange powder: $^1$NMR (300 MHz, DMSO-d$_6$) δ 8.70 (t, J=6 Hz, 2H), 7.86 (bs, 6H), 6.50 (bs, 4H), 3.46-3.58 (m, 4H), 3.26-3.40 (m, 4H). $^{13}$C NMR (75 MHz, DMSO-d6) δ 166.4 (s), 146.8 (s), 127.0 (s), 39.4 (t), 37.4 (t). LCMS (5-95% gradient acetonitrile in 0.1% TFA over 10 min), single peak retention time=3.62 min on 30 mm column, (M+H)+=283. UV/vis (100 μM in PBS) λ$_{abs}$=435 nm. Fluorescence (100 nM) λex=449 nm, λ$_{em}$=562.

Example 8: 3,6-diamino-N$^2$,N$^5$-bis(D-aspartate)-pyrazine-2,5-dicarboxamide

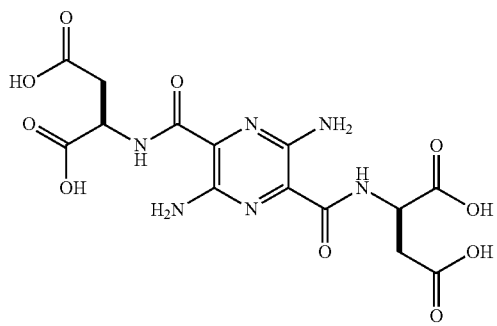

Step 1. Synthesis of 3,6-diamino-N²,N⁵-bis(benzyl D-O-benzyl-Aspartate)-pyrazine-2,5-dicarboxamide

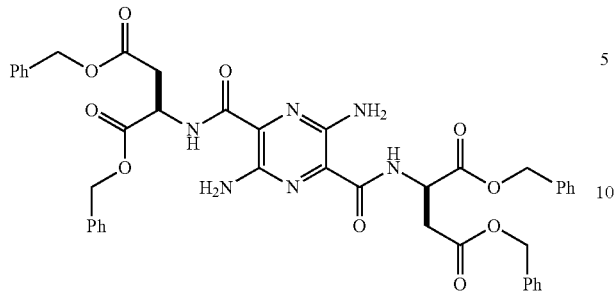

A mixture of sodium 3,6-diaminopyrazine-2,5-dicarboxylate (600 mg, 2.48 mmol), Asp(OBn)-OMe-p-TosH salt (2.43 g, 5.00 mmol), HOBt-H₂O (919 mg, 6.00 mmol) and EDC-HCl (1.14 g, 5.95 mmol) in DMF (50 mL) was treated with TEA (4 mL). The resulting mixture was stirred over night at room temperature. The reaction mixture was concentrated and the residue was partitioned with water and EtOAc. The EtOAc layer was separated and washed successively with saturated sodium bicarbonate, water and brine. The EtOAc solution was dried (Na₂SO₄), filtered and concentrated. The residue was purified by flash chromatography (SiO₂, 50/1 CHCl₃-MeOH to 10/1) to afford 1.15 g of the bis-amide (58% yield) as a yellow foam: ¹NMR (500 MHz, CDCl₃) δ 8.61 (d, J=8.4 Hz, 2H), 7.29-7.39 (m, 20H), 5.85 (bs, 4H), 5.22 (ABq, J=10.0 Hz, Av=17.3 Hz, 4H), 5.10 (ABq, J=12.2 Hz, Av=34.3 Hz, 4H), 5.06-5.09 (obs m, 2H), 3.11 (ABq of d, J=17.0, 5 5.14 Hz, Av=77.9 Hz, 4H). ¹³C NMR (75 MHz, CDCl₃) δ 170.7 (s), 170.7 (s), 165.4 (s), 147.0 (s), 135.7 (s), 135.6 (s), 129.0 (d), 128.9 (d), 128.8 (d), 128.75 (d), 128.7 (d), 126.9 (s), 68.0 (t), 67.3 (t), 49.1 (d), 37.0 (t). LCMS (50-95% 10 gradient acetonitrile in 0.1% TFA over 10 min), single peak retention time=5.97 min on 250 mm column, (M+H)+=789.

Step 2. Synthesis of 3,6-diamino-N²,N⁵-bis(D-aspartate)-pyrazine-2,5-dicarboxamide To the product from Step 1 (510 mg, 0.65 mmol) was added THF (20 mL) and water (10 mL). To this stirred mixture was added 10% Pd(C) (500 mg) and ammonium formate (1 g). The resulting mixture was heated to 60° C. for 2 h and allowed to cool to room temperature. The mixture was filtered through celite and concentrated. The resulting material was purified again by reverse phase medium pressure chromatography (C18, 10-70% manual gradient acetonitrile in 0.1% TFA) to afford 137.8 mg (54% yield) of Example 8 as an orange solid: ¹NMR (300 MHz, DMSO-d6) δ 8.62 (d, J=8.4 Hz, 2H), 6.67 (bs, 4H), 4.725 (dt, J=8.4, 5.4 Hz, 2H), 25 2.74-2.88 (complex m, 4H). ¹³C NMR (75 MHz, DMSO-d6) δ 172.6 (s), 165.2 (s), 147.0 (s), 126.6 (s), 60.8 (t), 49.1 (d). LCMS (5-95% gradient acetonitrile in 0.1% TFA over 10 min), single peak retention time=4.01 min on 250 mm column, (M+H)+=429. UV/vis (100 μM in PBS) λab=433 nm. Fluorescence (100 nM) λ$_{ex}$=449 nm, λ$_{em}$=558 nm.

Example 9: 3,6-diamino-N²,N⁵-bis(14-oxo-2,5,8,11-tetraoxa-15-azaheptadecan-17-yl) pyrazine-2,5-dicarboxamide

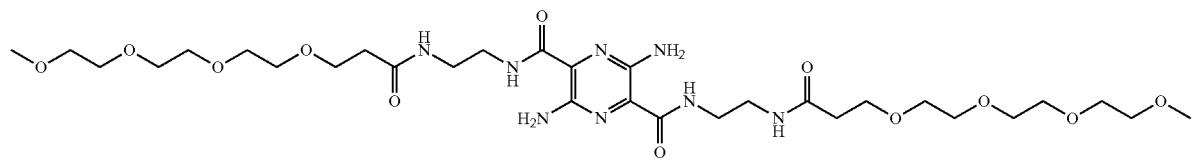

To a solution of Example 7 (77.4 mg, 0.15 mmol) in DMF 50 (5 mL) was added TEA (151 mg, 1.49 mmol) and 2,5-dioxopyrrolidin-1-yl 2,5,8,11-tetraoxatetradecan-14-oate (113 mg, 0.34 mmol) and the reaction was stirred for 16 h at room temperature. The reaction was concentrated and the residue was purified by medium pressure reversed phase chromatography (LiChiroprep RP-18 Lobar (B) 25×310 mm-EMD chemicals 40-63 μm, ~70 g, 90/10 to 80/20 0.1% TFA-ACN) to afford 37.4 mg (35% yield) of Example 9 as an orange film: ¹NMR (300 MHz, DMSO-d₆) δ 8.47 (t, J=5.7 Hz, 2H), 7.96 (t, J=5.4 Hz, 2H), 3.20-3.60 (complex m, 36H), 3.47 (s, 3H), 60 3.46 (s, 3H), 2.30 (t, J=6.3 Hz, 4H). ¹³C NMR (75 MHz, DMSO-d6) δ 170.2 (s), 165.1 (s), 146.0 (s), 126.2 (s), 71.2 (t), 69.7 (t), 69.6 (t), 69.5 (t), 69.4 (t), 66.7 (t), 58.0 (q), 38.2 (t), 36.2 (t). LCMS (5-95% gradient acetonitrile in 0.1% TFA over 10 min), single peak retention time=4.01 min on 250 mm column, (M+H)+=719, (M+Na)+=741. UV/vis (100 μM in PBS) λ$_{abs}$=437 nm. Fluorescence (100 nM) λex=437 nm, λ$_{em}$=559 nm.

Example 10: 3,6-diamino-N²,N⁵-bis(26-oxo-2,5,8,11,14,17,20,23-octaoxa-27-azanonacosan-29-yl) pyrazine-2,5-dicarboxamide

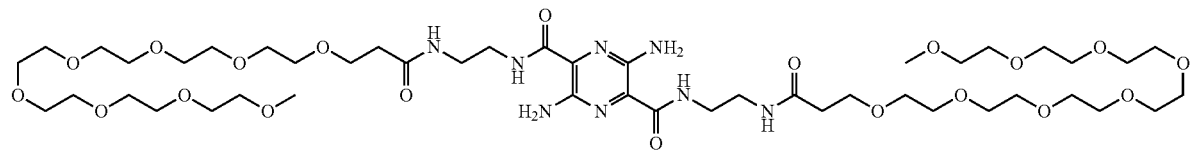 [SMILES: COCCOCCOCCOCCOCCOCCOCCOCCC(=O)NCCNC(=O)c1nc(N)c(C(=O)NCCNC(=O)CCOCCOCCOCCOCCOCCOCCOCCOC)nc1N]

To a solution of Example 7 (50.3 mg, 0.10 mmol) in DMF (5 mL) was added TEA (109 mg, 1.08 mmol) and 2,5-dioxopyrrolidin-1-yl 2,5,8,11,14,17,20,23-octaoxahexacosan-26-oate (128 mg, 0.25 mmol) and the reaction was stirred for 16 h at room temperature. The reaction was concentrated and the residue was purified by medium pressure reversed phase chromatography (LiChroprep RP-18 Lobar (B) 25×310 mm-EMD chemicals 40-63 m, ~70 g, 90/10 to 80/20 0.1% TFA-ACN) to afford 87.9 mg (82% yield) of Example 10 as an orange film: $^1$NMR (300 MHz, DMSO-d6) δ 8.46 (t, J=5.7 Hz, 2H), 7.96 (t, J=5.4 Hz, 2H), 3.16-3.73 (complex m, 74H), 2.28-2.32 (m, 2H). $^{13}$C NMR (75 MHz, DMSO-$d_6$) multiple conformations, δ 170.1 (s), 169.9 (s) 169.8 (s), 165.1 (s), 146.0 (s), 126.2 (s). 71.2 (t), 69.7 (t), 69.6 (t), 69.5 (t), 66.7 (t), 58.0 (q), 38.2 (t), 36.2 (t). LCMS (15-95% gradient acetonitrile in 0.1% TFA over 10 min), single peak retention time=5.90 min on 250 mm column, (M+H)+=1 071, (M+2H)2+=536. UV/vis (100 μM in PBS) $λ_{abs}$=438 nm. Fluorescence (100 nM) λex=438 nm, $λ_{em}$=560 nm.

Example 11: 3,6-diamino-$N^2$,$N^5$-bis(38-oxo-2,5,8,11,14,17,20,23,26,29,32,35-dodecaoxa-39-azahentetracontan-41-y) pyrazine-2,5-dicarboxamide

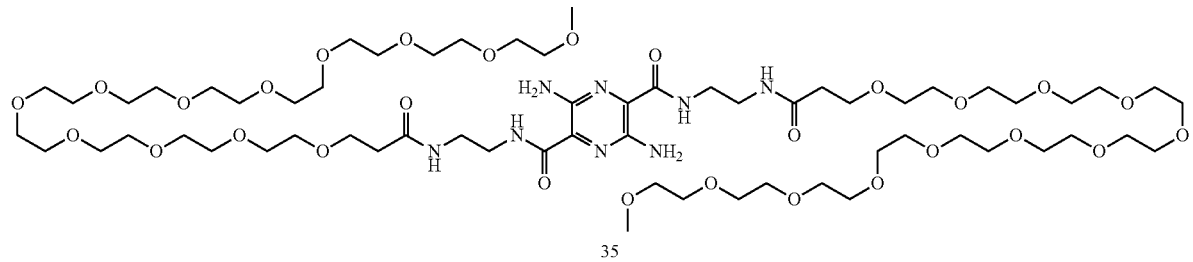

To a solution of Example 7 (53.1 mg, 0.10 mmol) in DMF (5 mL) was added TEA (114 mg, 1.13 mmol) and 2,5-dioxopyrrolidin-1-yl 2,5,8,11,14,17,20,23,26,29,32,35-dodeca-oxaoctatriacontan-38-oate (144 mg, 0.21 mmol) in DMF (2.0 mL) and the resulting mixture was stirred for 16 h thereafter. The reaction was concentrated and the residue was purified by medium pressure reversed phase chromatography (LiChroprep RP-18 Lobar (B) 25×310 mm-EMD chemicals 40-63 (mm, ~70 g, 90110 to 80/20 0.1% TFA-ACN) to afford 87.5 mg (61% yield) of Example 11 as an orange film: $^1$NMR (300 MHz, DMSO-$d_6$) δ 8.48 (t, J=5.7 Hz, 2H), 7.96 (t, J=5.4 Hz, g0 2H), 7.80-7.86 (m, 2H), 5.94 (bm, 2H), 3.30-3.60 (complex m, 106H), 2.26-2.33 (m, 4H). $^{13}$C NMR (75 MHz, DMSO-$d_6$) δ 170.2 (s), 165.1 (s), 146.0 (s), 126.2 (s), 71.2 (t), 69.7 (t), 69.6 (t), 69.5 (t), 66.7 (t), 58.0 (q), 38.2 (t), 36.2 (t). LCMS (15-95% gradient acetonitrile in 0.1% TFA over 10 min), single peak retention time=5.90 min on 250 mm column, (M+2H)2+=712. UV/vis (100 μM in PBS) λab=449 nm. Fluorescence (100 nM) λex=449 nm, $λ_{em}$=559 nm.

Example 12: 3,6-diamino-$N^2$,$N^5$-bis(2-(PEG-5000) aminoethyl) pyrazine-2,5-dicarboxamide

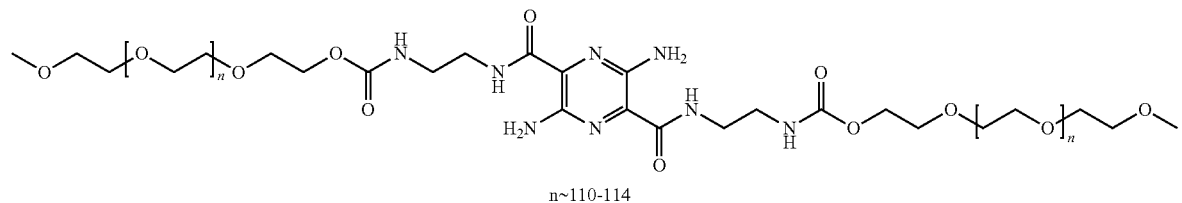

n~110-114

A solution of Example 7 (25 mg, 0.049 mmol) in DMF (30 mL) was treated with TEA (1 mL) and m-PEG5000-NHS (1 g, 0.2 mmol) and the resulting mixture was stirred for 48 h at room temperature. The mixture was concentrated and the residue was partially purified by gel filtration chromatography (G-25 resin, water). The product was concentrated and further purified by reverse phase medium pressure chromatography (C18, 10-70% manual gradient acetonitrile in 0.1% TFA) to afford 137.8 mg (54% yield) of Example 12 as a tan waxy solid: Maldi MS m/z=11393.

Example 13: (R)-2-(6-(bis(2-methoxyethyl)amino)-5-cyano-3-morpholinopyrazine-2-carboxamido)succinic acid

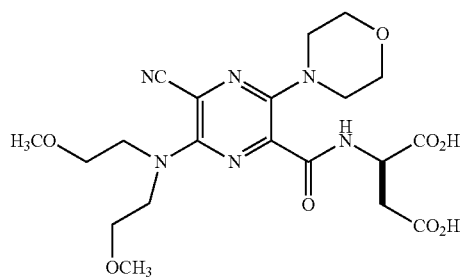 [SMILES: COCCN(CCOC)c1nc(C(=O)N[C@H](CC(=O)O)C(=O)O)c(N2CCOCC2)nc1C#N]

Step 1. Synthesis of 2-amino-5-bromo-3,6-dichloropyrazine

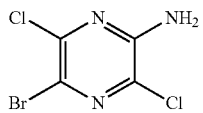

A solution of 2-amino-6-chloropyrazine (25 g, 193.1 mmol) in MeOH (500 mL) was treated with NBS (34.3 g, 193.1 mmol), portion-wise, over 1 hour. The resulting mixture was stirred for 16 hours thereafter. TLC analysis at this time shows a small amount of starting material remaining. Another 1.4 g NBS added and reaction heated to 50° C. for 2 hours. The mixture was then cooled to 38° C. and treated with NCS (25.8 g, 193.1 mmol). The reaction mixture was heated to 50° C. for 16 hours thereafter. The mixture was then cooled to room temperature and treated with water (500 mL). The precipitate was collected by filtration and dried in a vacuum dessicator to afford 45.4 g (97% yield) of 2-amino-5-bromo-3,6-dichloropyrazine as a white solid: $^{13}$C NMR (75 MHz, CDCl$_3$) δ 149.9 (s), 145.6 (s), 129.6 (s), 121.5 (s). LCMS (15-95% gradient acetonitrile in 0.1% TFA over 10 min), single peak retention time=4.51 min on 30 mm column, (M+H)+=244, (M+H+ACN)+=285.

Step 2. Synthesis of 5-amino-3,6-dichloropyrazine-2-carbonitrile

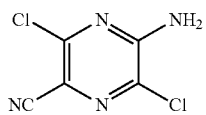

A mixture of CuCN (8.62 g, 96.3 mmol) and NaCN (4.72 g, 96.3 mmol) was heated under high vacuum to 90° C. The resulting mixture was subjected to three Argon/vacuum cycles and placed under a final positive pressure of Argon. The mixture was allowed to cool to room temperature and DMF (150 mL) was added. The heterogeneous mixture was heated to 130° C. for 2.5 hours. To the resulting homogeneous mixture of sodium dicyanocuprate was added a solution of the product from Step 1 (15.6 g, 64.2 mmol) dissolved in DMF (150 mL), dropwise, over 1 hour. The temperature was gradually raised to 150° C. and the resulting mixture was stirred at this temperature for 10 hours thereafter. The reaction was then allowed to cool to room temperature and poured into water (1 L). The resulting mixture was extracted with EtOAc (3×) and the combined extracts were filtered to remove a flocculent dark solid, washed with brine, dried (Na$_2$SO$_4$), filtered again and concentrated. Purification by flash column chromatography (SiO$_2$, 10/1 hexanes-EtOAc to 3/1) to afford 6.70 g (55% yield) of the nitrile product as a tan solid: $^{13}$C NMR (75 MHz, CDCl$_3$) δ 153.9 (s), 149.1 (s), 131.7 (s), 115.4 (s), 111.0 (s). GCMS (Inj. temperature=280° C., 1.0 mL/min helium flow rate, temperature program: 100° C. (2 min hold), ramp to 300° C. @ 10° C./min (2 min hold), major peak retention time=6.56 min, m/z (EI)=188, 190.

Step 3. Synthesis of 5-amino-3-(bis(2-methoxyethyl) amino)-6-chloropyrazine-2-carbonitrile

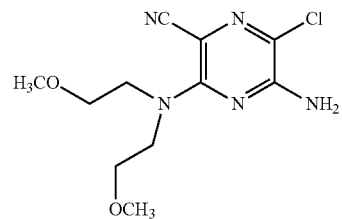 [SMILES: COCCN(CCOC)c1nc(N)c(Cl)nc1C#N]

To the product from Step 2 (1.00 g, 5.29 mmol) in ACN (20 mL) was added bis(2-methoxyethyl)amine (3.0 mL, 2.71 g, 20.3 mmol) and the reaction mixture was heated to 70° C. for 16 hours thereafter. The reaction was cooled and concentrated. The residue was partitioned with EtOAc and water. The organic layer was separated and the aqueous was extracted again with EtOAc. The combined organic extracts were washed with brine, dried (Na$_2$SO$_4$), filtered and concentrated. Purification by flash column chromatography (SiO$_2$, 10/1 hexanes-EtOAc to 1/1) afforded 950 mg (63% yield) of the desired adduct as a yellow solid: $^1$NMR (300 MHz, CDCl$_3$) δ 7.47 (bs, 2H), 3.77 (t, J=5.7 Hz, 4H), 3.52 (t, J=5.4 Hz, 4H), 3.25 (s, 6H). $^{13}$C NMR (75 MHz, CDCl$_3$) δ 154.7 (s), 152.0 (s), 120.9 (s), 119.5 (s), 95.8 (s), 71.0 (t), 59.1 (q), 50.0 (t). LCMS (50-95% gradient acetonitrile in 0.1% TFA over 10 min), single peak retention time=4.91 min on 250 mm column, (M+H)+=286, (M+Na)+=308, (M+Na+ACN)+=349.

Step 4. Synthesis of 3-(bis(2-methoxyethyl)amino)-5-bromo-6-chloropyrazine-2-carbonitrile

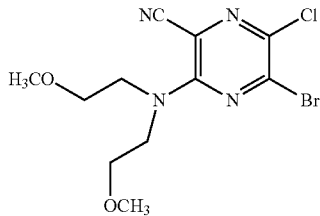 [SMILES: COCCN(CCOC)c1nc(Br)c(Cl)nc1C#N]

To the product from Step 3 (1.39 g, 4.88 mmol) in 48% hydrobromic acid (20 mL) at 0° C. (ice-salt bath), was added a solution of sodium nitrite (673 mg, 9.75 mmol) in water (10 mL) dropwise over 30 min. The resulting mixture concentrated. Purification by flash column chromatography ($SiO_2$, 50/1 $CHCl_3$-MeOH) afforded 1.00 g (58% yield) of the bromide as an orange-brown solid: $^1$NMR (300 MHz, $CDCl_3$) δ 3.99 (t, J=5.4 Hz, 4H), 3.64 (t, J=5.4 Hz, 4H), 3.35 (s, 6H). $^{13}$CNMR (75 MHz, $CDCl_3$) δ 152.8 (s), 140.8 (s), 133.4 (s), 117.2 (s), 108.3 (s), 70.4 (t), 59.1 (t), 50.5 (q). LCMS (50-95% gradient acetonitrile in 0.1% TFA over 10 min), single peak retention time=4.55 min on 250 mm column, (M+H)+=349, 351.xture was stirred at 0-5° C. for 1 h and poured into a stirred solution of $CuBr_2$ (1.64 g, 7.34 mmol) in water (100 mL). The resulting mixture 45 was stirred for 16 h at room temperature thereafter. The mixture was extracted with EtOAc (3×). The combined organic layers were dried ($Na_2SO_4$), filtered and concentrated. Purification by flash column chromatography ($SiO_2$, 50/1 $CHCl_3$-MeOH) afforded 1.00 g (58% yield) of the bromide as an orange-brown solid: $^1$NMR (300 MHz, $CDCl_3$) δ 3.99 (t, J=5.4 Hz, 4H), 3.64 (t, J=5.4 Hz, 4H), 3.35 (s, 6H). $^{13}$CNMR (75 MHz, $CDCl_3$) δ 152.8 (s), 140.8 (s), 133.4 (s), 117.2 (s), 108.3 (s), 70.4 (t), 59.1 (t), 50.5 (q). LCMS (50-95% gradient acetonitrile in 0.1% TFA over 10 min), single peak retention time=4.55 min on 250 mm column, (M+H)+=349, 351

Step 5. Synthesis of 3-(bis(2-methoxyethyl amino)-6-chloro-5-(furan-2-yl)pyrazine-2-carbonitrile

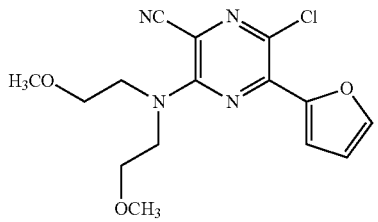 [SMILES: COCCN(CCOC)c1nc(-c2ccco2)c(Cl)nc1C#N]

A mixture of the product from Step 4 (1.0 g, 2.87 mmol), 2-furanboronic acid (643 mg, 5.75 mmol), $Cs_2CO_3$ (3.31 g, 10.2 mmol), TFP (35 mol %, 236 mg, 1.02 mmol), and $Pd_2dba_3$-$CHCl_3$ (5 mol %, 10 mol % Pd, 150 mg) was subjected to 3 vacuum/Argon cycles and placed under a positive pressure of Argon. Anhydrous dioxane (50 mL) was added and the reaction mixture was heated to 75° C. for 16 h thereafter. The reaction mixture was cooled to room temperature, diluted with EtOAc (100 mL) and filtered through a medium frit. Concentration and purification of the residue by flash chromatography ($SiO_2$, 50/1 $CHCl_3$-MeOH) afforded the 757 mg of the furan adduct (78% yield) as a tan powder: LCMS (5-95% gradient acetonitrile in 0.1% TFA over 10 min), single peak retention time=6.41 min on 250 mm column, (M+H)+=337.

Step 6. Synthesis of 6-(bis(2-methoxyethyl)amino)-3-chloro-5-cyanopyrazine-2-carboxylic acid

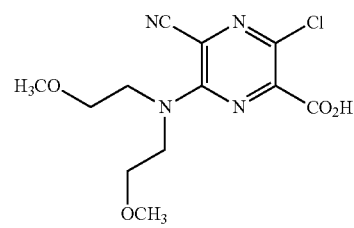 [SMILES: COCCN(CCOC)c1nc(C(=O)O)c(Cl)nc1C#N]

To a well stirred mixture of ACN (11 mL), $CCl_4$ (7 mL), and water (11 mL) were added sodium periodate (1.07 g, 5.00 mmol) and $RuO_2$.H20 (13.3 mg, 0.10 mmol), sequentially. The resulting mixture was stirred vigorously at room temperature for 30 min and treated with sodium bicarbonate (2.10 g, 25.0 mmol) followed by water (5 mL). Vigorous stirring for another 15 minutes was followed by the addition of a solution of the product from Step 5 (276 mg, 0.82 mmol) dissolved in ACN (1 mL). The green mixture was stirred at room temperature for 5.5 h. The mixture was transferred to a separatory funnel and extracted with EtOAc. The aqueous layer was adjusted to pH about 3.5 and extracted again with EtOAc (2×). The combined extracts were washed with 20% sodium bisulfite and brine and dried ($Na_2SO_4$). Filtration and concentration afforded 140 mg (54% yield) of carboxylic acid as a pale yellow solid: LCMS (5-95% gradient acetonitrile in 0.1% TFA over 10 min), single peak retention time=5.05 min on 250 mm column, (M+H)+=315.

Step 7. Synthesis of (R)-dibenzyl 2-(6-(bis(2-methoxy-ethyl)amino)-3-chloro-5-cyanopyrazine-2-carboxamido) succinate

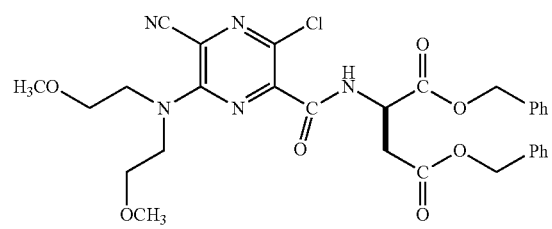 [SMILES: COCCN(CCOC)c1nc(C(=O)N[C@H](CC(=O)OCc2ccccc2)C(=O)OCc2ccccc2)c(Cl)nc1C#N]

A mixture of the product from step 6 (140 mg, 0.45 mmol), EDC-HCl (128 mg, 0.67 mmol), HOBt $H_2O$ (102 mg, 0.67 mmol) in anhydrous DMF (25 mL) was stirred together at room temperature for 30 min. To this stirred mixture was added (R)-dibenzyl 2-aminosuccinate TsOH salt (213 mg, 0.44 mmol) followed by TEA (1 mL). The resulting mixture was stirred for 16 h thereafter. The reaction mixture was concentrated and partitioned with EtOAc and saturated sodium bicarbonate solution. The EtOAc layer was separated and washed with saturated sodium bicarbonate and brine, dried ($Na_2SO_4$), filtered and concentrated to afford 5 240 mg (88% yield) of the pyrazine amide as an orange foam: LCMS (15-95% gradient acetonitrile in 0.1% TFA over 10 min), single peak retention time=8.76 min on 250 mm column, (M+H)+=610, (M+Na)+=632.

Step 8. Synthesis of (R)-dibenzyl 2-(6-(bis(2-methoxyethyl)amino)-5-cyano-3-morpholinopyrazine-2-carboxamido)succinate

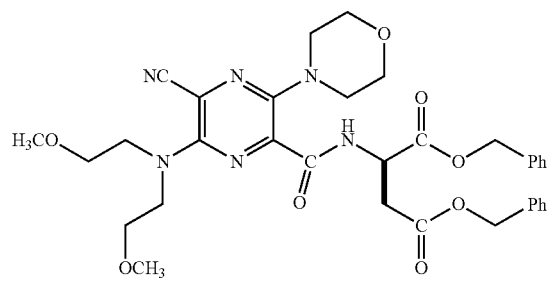 [SMILES: COCCN(CCOC)c1nc(C(=O)N[C@H](CC(=O)OCc2ccccc2)C(=O)OCc2ccccc2)c(N2CCOCC2)nc1C#N]

To the product from Step 7 (240 mg, 0.39 mmol) was added morpholine (5 mL). The reaction mixture was heated to 70° C. for 2 h. The mixture was cooled and concentrated. The residue was partitioned with EtOAc and water. The EtOAc layer was separated and washed with saturated sodium bicarbonate and brine. The EtOAc layer was dried (Na₂SO₄), filtered and concentrated. Purification by flash column chromatography (SiO₂, 3:1 to 1:1 hexanes-EtOAc) afforded 199 mg (75% yield) of the morpholine adduct as an orange foam: LCMS (15-95% gradient acetonitrile in 0.1% TFA over 10 min), single peak retention time=8.76 min on 250 μm column, (M+H)+=661, (M+Na)+=683.

Step 9. Synthesis of (R)-2-(6-(bis(2-methoxyethyl)amino)-5-cyano-3-morpholinopyrazine-2-carboxamido)succinic acid The dibenzyl ester (115 mg, 0.17 mmol) in THF (10 mL) was added 1.0 N sodium hydroxide (4 mL). The mixture was stirred for 1 h at room temperature. The pH was adjusted to about 2 with 1.0 N HCl and the solution was concentrated. Purification of the residue by medium pressure reversed phase chromatography (LiChroprep RP-18 Lobar (B) 25×310 mm-EMD chemicals 40-63 (μm, –70 g, 90/10 to 50/500.1% TFA-ACN) afforded 32 mg (27% yield) of Example 13 as an orange solid: LCMS (15-95% gradient acetonitrile in 0.1% TFA over 10 min), single peak retention time=4.47 min on 250 mm column, (M+H)=481. UV/vis (100 μM in PBS) λ$_{abs}$=438 nm. Fluorescence (100 μM) λex=449 nm, λ$_{em}$=570.

Example 14: 3,6-diamino-N², N⁵-bis (2-hydroxy-3-serine)-pyrazine-2,5-dicarboxamide

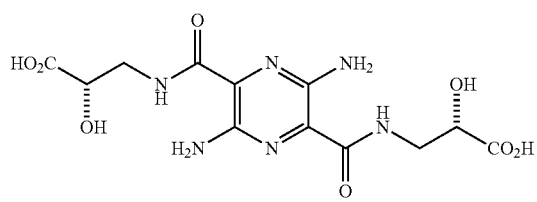 [SMILES: Nc1nc(C(=O)NC[C@H](O)C(=O)O)c(N)nc1C(=O)NC[C@H](O)C(=O)O]

The title compound may be prepared by using substantially the procedure of Example 2 but substituting 2-OBn-3-serine-OMe-HCl salt for (D)-Ser(OBn)-OMe-HCl salt in an equivalent amount in Step 1.

Example 15: 3,6-diaminopyrazine-2,5-dicarboxylic acid

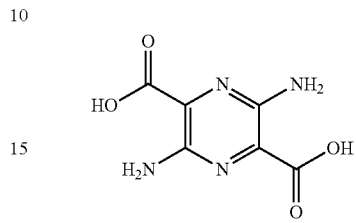

Dipotassium 2,4,6,8-tetrahydroxypyrimido(4,5-g)pteridine was prepared by treating 5-aminouracil with potassium ferricyanide in the presence of potassium hydroxide as described in Taylor et al., JACS, 77: 2243-2248 (1955).

In each of two Teflon reaction vessels was placed 0.5 g dipotassium 2,4,6,8-tetrahydroxypyrimido[4,5g]pteridine and a solution consisting of 0.3-0.4 g sodium hydroxide in about 10 mL deionized water. The vessels were secured in the microwave reactor and allowed to react for one hour at 170° C., generating ca. 100 psig pressure, for one hour. The vessels were allowed to cool in the microwave to ca. 50° C. and the contents filtered to remove a small amount of solid residue. The bright yellow filtrate was transferred to a 250 mL round-bottom flask equipped with a large magnetic stir bar. With stirring, the pH was adjusted to ca. 3 with concentrated HCl. A large amount of red precipitate formed. A few more drops of acid was added and the solid collected by filtration on a glass frit, washed with cold IN HCl (1×10 mL), acetonitrile (2×30 mL) and diethyl ether (1×30 mL), suctioned dry and transferred to a vacuum oven, vacuum drying overnight at 45-50° C. Yield 0.48 g (79%). C¹³ NMR (D₂O/NaOD, external TMS reference) δ 132.35, 147.32, 171.68.

Example 16: 3,6-diamino-N²,N⁵-di(2,5,8,11,14,17,20,23,26,29,32,35,38,41,44,47,50,53,56,62,65,68,71-tetracosaoxatriheptacosan-73-yl)pyrazine-2,5-dicarboxamide

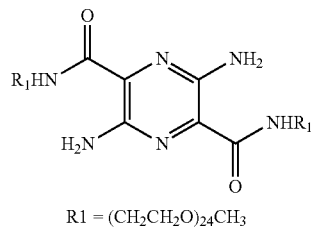

R1 = (CH₂CH₂O)₂₄CH₃

A round-bottom flask (2 L) equipped with a magnetic stir bar was charged with 3,6-diaminopyrazine-2,5-dicarboxylic acid (3.50 g, 17.7 mmol), m-dPEG24-amine (45 g, 40.2 mmol), and PyBOP (21.4 g, 41.1 mmol) in anhydrous DMF (1 L) and the reaction mixture was purged with argon. Triethylamine (50 mL) was slowly added to the suspension and within an hour the reactants had dissolved leading to a dark red solution. The reaction mixture was stirred overnight at rt, concentrated under high vacuum to give the crude product as a dark red oil that was purified by reverse phase preparative HPLC (column: Waters XBridge Prep C18 5 mm OBD 30×150 mm; $\lambda_{max}$; PDA (200-800 nm), flow rate: 50 mL/min; gradient: A:B 95:5/1 min, 50:50/8 min, 5:95/8.1 min, 5:95/10 min (A: H$_2$O/0.1% TFA, B: CH$_3$CN/0.1% TFA). Product containing fractions were combined, concentrated in vacuo and the residue dissolved in CHCl$_3$ (150 mL), washed with saturated NaHCO$_3$ (2×75 mL) and brine (75 mL), dried over Na$_2$SO$_4$ and evaporated to dryness. The gummy residue was co-evaporated with EtOH (absolute) and dried overnight under high vacuum at 40° C. to give the title product as a red solid (20.0 g, 61%). $^1$H NMR (CDCl$_3$) δ 8.13 (t, J=5.8 Hz, 2H), 6.06 (s, 4H), 3.68-3.54 (m, 192H), 3.38 (s, 6H); $^{13}$C NMR (CDCl$_3$) δ 165.3, 146.6, 126.9 71.9, 70.63, 70.6, 70.56, 70.5, 70.4, 69.8, 59.0, 39.0; RP-LC/MS (ESI) m/z 1179.1 (M+H+NH$_4$)$^{2+}$ (t$_r$=3.88 min). Anal. Calcd for C$_{104}$H$_{204}$N$_6$O$_{50}$: C, 53.41; H, 8.79: N, 3.61. Found: C, 53.15: H, 8.81; N, 3.61.

Example 17: 3,6-bis(2,5,8,11,14,17,20,23,26,29,32,35-dodecaoxaoctatriacontan-38-ylamino)-N$^2$,N$^5$-di(2,5,8,11,14,17,20,23,26,29,32,35-dodecaoxaheptatriacontan-37-yl)pyrazine-2,5-dicarboxamide layer extracted further with CHCl$_3$ (50 mL). The combined organic extracts were washed with brine (100 mL) and then dried over Na$_2$SO$_4$. Removal of volatiles in vacuo gave 12.8 g of crude product as a red solid that was purified by reverse phase preparative HPLC (column: Waters XBridge Prep C18 5 mm OBD 30×250 mm; $\lambda_m$ax; 280 nm, flow rate: 50 mL/min; gradient: A:B 75:25/0 min, 75:25/5 min, 45:55/40 min, 5:95/8.1 min, 5:95/40 min (A: H$_2$O/0.1% TFA, B: CH$_3$CN/0.1% TFA). Product containing fractions were combined, concentrated in vacuo and the residue dissolved in CHCl$_3$ (200 mL), washed with saturated NaHCO$_3$ (2×100 mL) and brine (100 mL), dried over Na$_2$SO$_4$ and evaporated to dryness. The red viscous residue was co-evaporated with EtOH (absolute) and dried overnight under high vacuum at 40° C. to give the title product as a red brick solid (7.40 g, 63%). $^1$H NMR (DMSO-d$_6$) δ 8.42 (t, J=5.8 Hz, 2H), 7.88 (t, j=5.5 Hz, 2H), 3.64-3.34 (m, 192H), 3.23 (s, 12H), 1.79-1.75 (quintet, J=6.4 Hz, 4H); $^{13}$C NMR (DMSO-d$_6$) δ 165.9, 145.9, 126.3 71.7, 70.28, 70.25, 70.2, 70.12, 70.09, 70.05, 69.3, 68.8, 58.5, 39.0, 38.1, 29.8; RP-LC/MS (ESI) m/z 2394.5 (M+H)$^+$, 1197.7 (M+2H)$^{2+}$ (t$_r$=4.09 min). Anal.

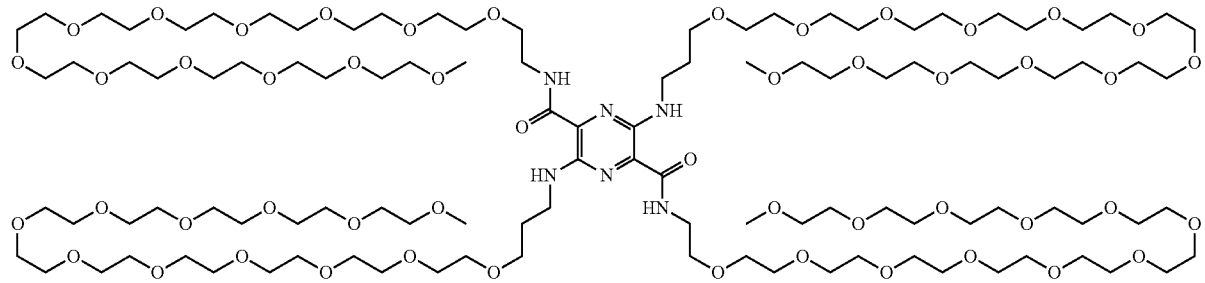 [SMILES: COCCOCCOCCOCCOCCOCCOCCOCCOCCOCCOCCOCCCNc1nc(C(=O)NCCOCCOCCOCCOCCOCCOCCOCCOCCOCCOCCOCCOC)c(NCCCOCCOCCOCCOCCOCCOCCOCCOCCOCCOCCOCCOC)nc1C(=O)NCCOCCOCCOCCOCCOCCOCCOCCOCCOCCOCCOCCOC]

A round-bottom flask (500 mL) equipped with a magnetic stir bar was charged with the product of Example 11, 3,6-diamino-N$^2$,N$^5$-bis(38-oxo-2,5,8,11,14,17,20,23,26,29,32,35-dodecaoxa-39-azahentetracontan-41-y) pyrazine-2,5-dicarboxamide (6.24 g, 4.87 mmol) and dissolved in anhydrous 1,2-dichloroethane (DCE, 100 mL) under argon. To the resulting orange solution, a solution of m-dPEG12-propionaldehyde (7.34 g, 12.8 mmol) in DCE (25 mL) and glacial HOAc (0.73 mL, 12.7 mmol) were added in succession. To this was added sodium triacetoxyborohydride (2.71 g, 12.8 mmol) in portions (0.50 g) over a 1.5 hr period each time rinsing the transfer vial with DCE (75 mL total). The resulting reddish suspension was stirred overnight at rt under argon and the reaction was quenched by slow addition of saturated sodium bicarbonate (100 mL). The biphasic mixture was stirred for 30 min, layers separated, and the aqueous Calcd for C$_{108}$H$_{212}$N$_6$O$_{50}$: C, 54.16; H, 8.92: N, 3.51. Found: C, 54.31: H, 8.91; N, 3.52.

Example 18: 3,3'-((3,6-diaminopyrazine-2,5 dicarbonyl)bis(azanediyl)) dipropionic acid

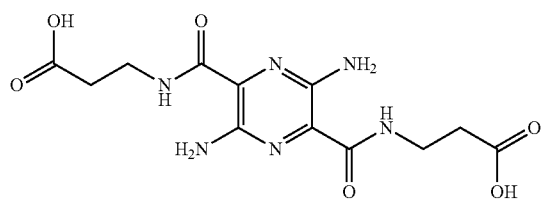 [SMILES: Nc1nc(C(=O)NCCC(=O)O)c(N)nc1C(=O)NCCC(=O)O]

Step 1. Synthesis of dibenzyl 3,3'-((3,6-diaminopyrazine-2,5-dicarbonyl) bis(azanediyl))dipropionate

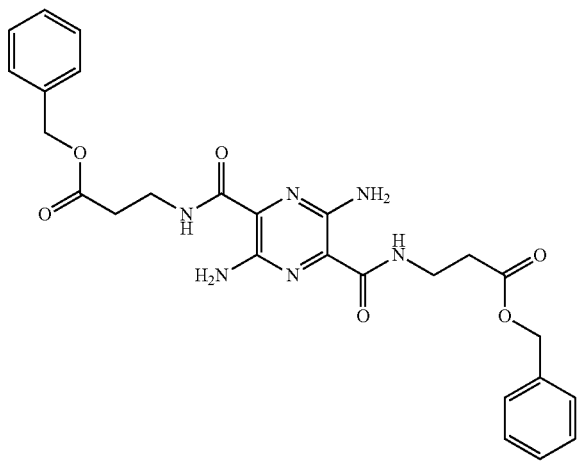 [SMILES: Nc1nc(C(=O)NCCC(=O)OCc2ccccc2)c(N)nc1C(=O)NCCC(=O)OCc1ccccc1]

A flame dried round-bottom flask (100 mL) equipped with a magnetic stir bar was charged with 3,6-diaminopyrazine-2,5-dicarboxylic acid (0.30 g, 1.54 mmol), benzyl 3-aminopropanoate p-toluene sulfonate (1.08 g, 3.08 mmol, MW 351.42), EDC HCl (0.590 g, 3.08 mmol, 191.7 g/mol), HOBt 3H$_2$O (0.582 g, 3.08 mmol, 189.13 g/mol), and Et$_3$N (1.50 g, 15 mmol, 101.2 g/mol, 2.0 mL d 0.73 g/mL) in DMF (anhydrous, 40 mL cannula transferred to the reaction vessel using Ar). An argon atmosphere was maintained throughout the course of the experiment. The reaction mixture becomes brown over time was stirred overnight at rt and concentrated in vacuo to about 10 mL (8 mbar at 60° C. water bath). Remaining DMF was removed by toluene azeotrope (2×10 mL toluene). The dark reaction mixture was partitioned between EtOAc (3×125 mL) and sat'd NaHCO$_3$ (3×100 mL). Combined the organic layers and partitioned against citric acid (10% aqueous, 100 mL) followed by brine. The organic layer was removed, dried (Na$_2$SO$_4$ anhydrous) and concentrated in vacuo to give a reddish crystalline solid, 0.58 g. TLC (EMD Silica gel 60 on glass support, EtOAc) shows one major spot (characteristically highly fluorescent using blue LED light) running close to the solvent front and very little remaining at the origin). TLC (1:1 EtOAc:hexanes) Rf 0.22. The product was purified via flash chromatography over silica gel (Teledyne ISCO GOLD column, 24 g, gradient: 100% hexanes to 100% EtOAc over 12 min at 35 mL/min with detection at both 254 nm and 450 nm) to give (0.49 g, 62% isolated yield). Mass spectrum (ES+) 521.36 (100%), 522.42 (30%), 523.34 (approx. 6%). NMR, $^1$H (DMSO-d$_6$), 400 MHz: 2.55 (4H, m), 3.41 (4H, m) 5.01 (4H, s), 6.44 (4H, s), 7.21 (10H, m), 8.41 (2H, m); $^{13}$C (DMSO-d6): 34.18, 35.33, 66.19, 126.74, 128.52, 128.92, 136.56, 146.75, 165.63, 171.90.

Step 2. Synthesis of dibenzyl 3,3'-((3,6-diaminopyrazine-2,5-dicarbonyl) bis(azanediyl))dipropionate
To 3,3'-((3,6-diaminopyrazine-2,5-dicarbonyl)bis(azanediyl))dipropionic acid

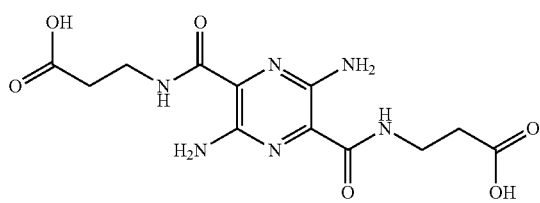

The di-benzyl ester of pyrazine-di-beta-alanine (dibenzyl 3,3'-((3,6-diaminopyrazine-2,5-dicarbonyl)bis(azanediyl)) dipropionate) prepared in Step 1 (0.92 g) was combined with EtOH (abs., 75 mL) and transferred to a Fischer-Porter pressure bottle (6 oz) equipped with inlet and outlet valves, a pressure gauge (0-100 psig) and a teflon coated magnetic stir bar. To this was added water (25 mL) and 10% Pd on carbon (0.2 g, Degussa/Aldrich wet) and the reaction vessel sealed. Following three vacuum/Ar cycles, hydrogen was introduced from a lecture bottle at 10 psig to a vigorously stirred solution. After 3.5 hrs a sample was withdrawn and TLC analysis (EMD Silica gel 60 on glass support, EtOAc) showed no starting material present only a highly yellow fluorescence spot (excitation by blue LED) at the origin. The crude reaction was filtered through a pad of celite and the resulting celite/catalyst bed rinsed with about 500 mL 1:1 EtOH:H$_2$O to obtain a yellow solution that was concentrated to a solid by rotovap (50° C.). A total of 0.424 g red solid was isolated (70.5% isolated yield). A small sample (about 1 mg) was dissolved in acetonitrile:water (4:1) and examined using a Waters Acquity UPLC using both UV and fluorescence detectors (FLD) (elution program: 0 to 3 min; 90% A: 10% B: 3 to 20 min; 10% A: 90% B: 20.1 to 30 min: 90% A to 10% B. A=water plus 0.01% TFA. B=ACN plus 0.01% TFA. UV at 264 nm. Column: Phenomenex Luna C18, 250 mm×4.5 mm). Only one peak was observed at 9.3 minutes. Mass spectrum (ES+) 341.32 (100%), 342.37 (30%), 344.29 (18%), 270.30 (62%). NMR, $^1$H (DMSO-d$_6$), 400 MHz: 2.54 (2H, m), 3.42 (2H, m), 6.52 (2H, s), 7.21 (4H, m), 8.38 (2H, m), 11.9 (2H, bs); $^{13}$C (DMSO-d6): 34.20, 35.33, 126.77, 146.75, 165.55, 173.57.

Example 19: 3,6-Diamino-N$^2$,N$^5$-bis(4-amino-butyric acid)-pyrazine-2,5-dicarboxamide

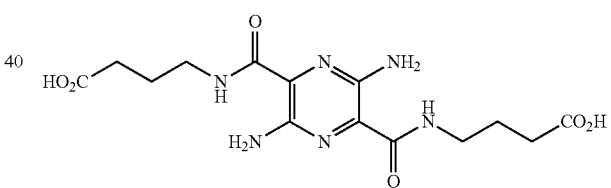

Step 1. Synthesis of 3,6-Diamino-N$^2$,N$^5$-bis(ethyl 4-amino-butyrate)-pyrazine-2,5-dicarboxamide diethyl ester

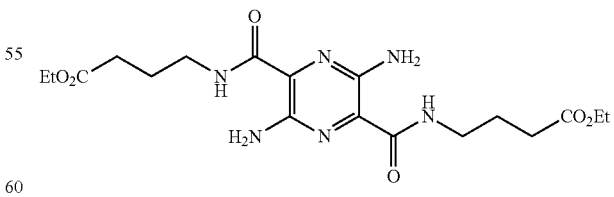

A mixture of sodium 3,6-diaminopyrazine-2,5-dicarboxylate (300 mg, 1.24 mmol), (ethyl 4-amino-butyrate HCl salt (2.64 mmol), HOBt-H$_2$O (570 mg, 3.72 mmol) and EDC-HCl (690 mg, 3.60 mmol) in DMF (25 mL) is treated with TEA (2 mL). The resulting mixture is stirred for 16 h and concentrated. The resulting mixture is concentrated to dryness and the residue partitioned between EtOAc and water. The layers are separated and the EtOAc solution washed with NaHCO$_3$ (saturated) and brine. The solution is dried over Na$_2$SO$_4$ (anhydrous), filtered and concentrated. Purification by radial flash chromatography or by reverse phase hplc using a C18 column affords the desired pyrazine intermediate that is carried forward in the next step.

Step 2. Synthesis of 3,6-Diamino-N$^2$,N$^5$-bis(4-amino-butyric acid)-pyrazine-2,5-dicarboxamide

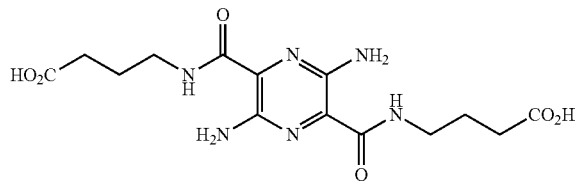 [SMILES: Nc1nc(C(=O)NCCCC(=O)O)c(N)nc1C(=O)NCCCC(=O)O]

The product from Step 1 in THF (about 400 mg in about 10 mLs THF should suffice) is treated with sodium hydroxide in water (1.0 N). After stirring at room temperature for about 30 min (or until the reaction is deemed complete by TLC) the pH is adjusted to approximately 2 by the addition of HCl in water (1.0 M) and the resulting solution extracted with EtOAc (3×). The organic layers are combined, dried (Na$_2$SO$_4$, anhydrous), filtered, concentrated and purified by rphplc to afford the title compound, 3,6-Diamino-N$^2$,N$^5$-bis (4-amino-butyric acid)-pyrazine-2,5-dicarboxamide.

Example 20: 3,6-Diamino-N$^2$,N$^5$-bis (3-amino-5-oxo-furane)-pyrazine-2,5-dicarboxamide

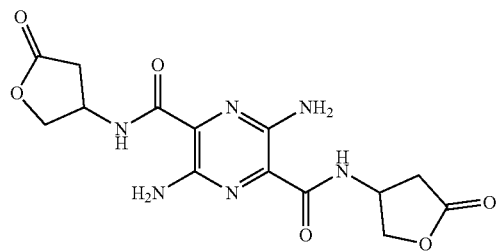 [SMILES: Nc1nc(C(=O)NC2COC(=O)C2)c(N)nc1C(=O)NC1COC(=O)C1]

A mixture of sodium 3,6-diaminopyrazine-2,5-dicarboxylate (300 mg, 1.24 mmol), 3-amino-5-oxo-furane HCl salt (synthesized as described in U.S. Pat. No. 6,037,365) (2.64 mmol), HOBt-H$_2$O (570 mg, 3.72 mmol) and EDC-HCl (690 mg, 3.60 mmol) in DMF (25 mL) is treated with triethylamine (2 mL). The resulting mixture is stirred for 16 h and concentrated to dryness and the residue taken up in the minimum amount of water. The aqueous mixture is acidified with TFA to pH about 2. Purification is achieved by reverse phase HPLC using a C18 column and a water:acetonitrile gradient to afford the desired pyrazine bis-lactone.

Example 21: 3,6-Diamino-N$^2$,N$^5$-bis (2,3-dimethyl-beta-alanine)-pyrazine-2,5-dicarboxamide

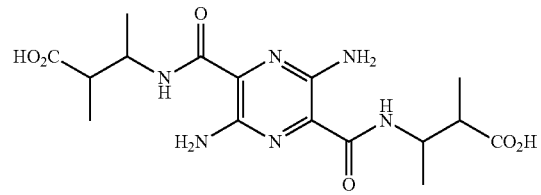 [SMILES: CC(NC(=O)c1nc(N)c(C(=O)NC(C)C(C)C(=O)O)nc1N)C(C)C(=O)O]

Step 1. Synthesis of 3,6-Diamino-N$^2$,N$^5$-bis (ethyl-2,3-dimethyl-beta-alanine)-pyrazine-2,5-dicarboxamide

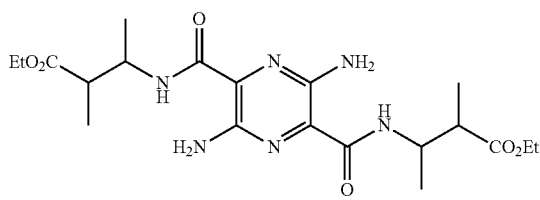 [SMILES: CCOC(=O)C(C)C(C)NC(=O)c1nc(N)c(C(=O)NC(C)C(C)C(=O)OCC)nc1N]

A mixture of sodium 3,6-diaminopyrazine-2,5-dicarboxylate (300 mg, 1.24 mmol), 2,3-dimethyl-beta-alanine ethyl ester HCl salt (2.64 mmol), HOBt-H$_2$O (570 mg, 3.72 mmol) and EDC-HCl (690 mg, 3.60 mmol) in DMF (25 mL) is treated with triethylamine (2 mL). The resulting mixture is stirred at room temperature for 16 h and concentrated. The resulting mixture is concentrated to dryness and the residue partitioned between EtOAc and water. The layers are separated and the EtOAc solution washed with NaHCO$_3$ (saturated) and brine. The resulting organic solution is dried over Na$_2$SO$_4$ (anhydrous), filtered and concentrated. Purification by radial flash chromatography, normal medium pressure flash chromatography or by reverse phase HPLC using a C18 column affords the desired pyrazine intermediate that is carried forward in the next step.

Step 2. Synthesis of 3,6-Diamino-N$^2$,N$^5$-bis (2,3-dimethyl-beta-alanine)-pyrazine-2,5-dicarboxamide

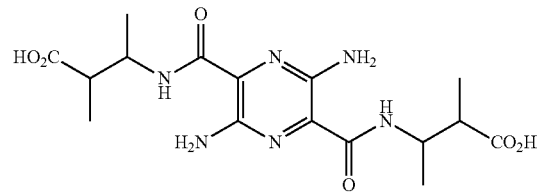 [SMILES: CC(NC(=O)c1nc(N)c(C(=O)NC(C)C(C)C(=O)O)nc1N)C(C)C(=O)O]

The product diethyl ester from Step 1 in THF (about 400 mg in about 10 mL should suffice) is treated with sodium hydroxide in water (1.0 N). After stirring at room temperature for about 30 min (or until the reaction is deemed complete by TLC) the pH is adjusted to approximately 2 by the addition of HCl in water (1.0 M) and the resulting solution extracted with EtOAc (3×). The organic layers are combined, dried (Na$_2$SO$_4$, anhydrous), filtered, and concentrated filtered to afford 3,6-Diamino-$N^2$,$N^5$-bis (2,3-dimethyl-beta-alanine)-pyrazine-2,5-dicarboxamide that may be purified by RPHPLC using a C18 column using an appropriate gradient of acetonitrile in 0.1% TFA and water in 0.1% TFA.

Example 22: 3,6-Diamino-$N^2$,$N^5$-bis (3-(3-pyridyl)-propionic acid)-pyrazine-2,5-dicarboxamide

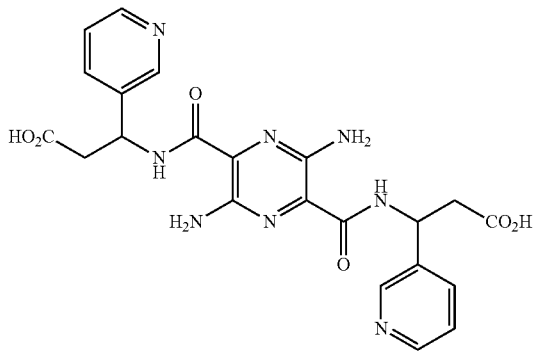 [SMILES: Nc1nc(C(=O)NC(CC(=O)O)c2cccnc2)c(N)nc1C(=O)NC(CC(=O)O)c1cccnc1]

Step 1. Synthesis of 3,6-Diamino-$N^2$,$N^5$-bis (ethyl 3-(3-pyridyl)-propanoate)-pyrazine-2,5-dicarboxamide

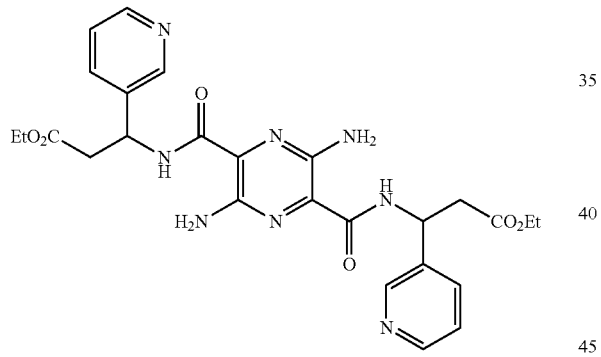

A mixture of sodium 3,6-diaminopyrazine-2,5-dicarboxylate (300 mg, 1.24 mmol), (ethyl 3-(3-pyridyl)-propanoate HCl salt (2.64 mmol) (J. G. Rico, et. al., J. Org. Chem., 1993, 58, 7948-7951), HOBt-$H_2O$ (570 mg, 3.72 mmol) and EDC-HCl (690 mg, 3.60 mmol) in DMF (25 mL) is treated with triethylamine (2 mL). The resulting mixture is stirred for 16 h at room temperature and concentrated. The resulting mixture is dissolved in the minimum amount of water, acidified to about pH 3 by addition of TFA and purified by by reverse phase HPLC using a C18 column affording the desired pyrazine intermediate diethyl ester that is carried forward in the next step.

Step 2. Synthesis of 3,6-Diamino-$N^2$,$N^5$-bis (ethyl 3-(3-pyridyl)-propanoate)-pyrazine-2,5-dicarboxamide The product from Step 1 in THF (about 400 mg in about 10 mLs THF) is treated with sodium hydroxide or lithium hydroxide in water (1.0 N). After stirring at room temperature for about 30 min (or until the reaction is deemed complete by TLC) the pH is adjusted to approximately 2 by the addition of TFA and the resulting solution purified by RPHPLC (C18, acetonitrile 0.1% TFA and water 0.1% TFA gradient) to afford the title compound, 3,6-Diamino-$N^2$,$N^5$-bis (ethyl 3-(3-pyridyl)-propanoate)-pyrazine-2,5-dicarboxamide.

Example 23: (2R,2'R)-2,2'-((3,3'-((3,6-diaminopyrazine-2,5-dicarbonyl)bis(azanediyl))bis(propanoyl))bis(azanediyl))disuccinic acid

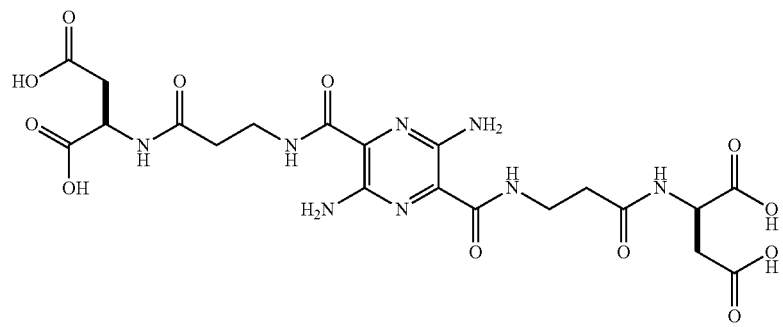 [SMILES: Nc1nc(C(=O)NCCC(=O)N[C@H](CC(=O)O)C(=O)O)c(N)nc1C(=O)NCCC(=O)N[C@H](CC(=O)O)C(=O)O]

Step 1. Synthesis of tetrabenzyl 2,2'-((3,3'-((3,6-diaminopyrazine-2,5-dicarbonyl)bis(azanediyl))bis(propanoyl))bis(azanediyl))(2R,2'R)-disuccinate

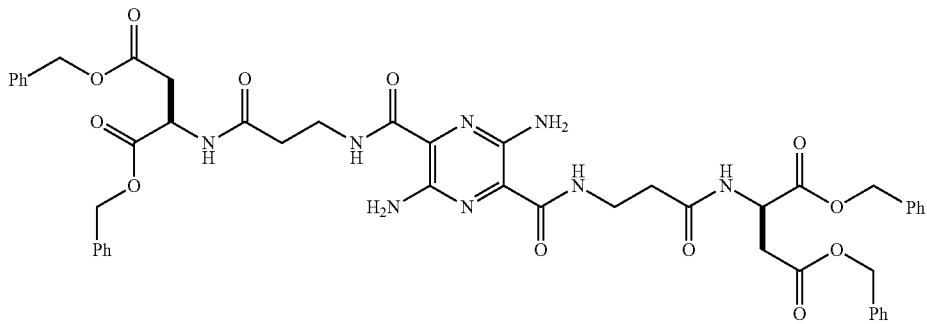 [SMILES: Nc1nc(C(=O)NCCC(=O)N[C@H](CC(=O)OCc2ccccc2)C(=O)OCc2ccccc2)c(N)nc1C(=O)NCCC(=O)N[C@H](CC(=O)OCc1ccccc1)C(=O)OCc1ccccc1]

3,3'-((3,6-diaminopyrazine-2,5 dicarbonyl)bis(azanediyl)) dipropionic acid produced in Example 18 (0.50 g, 1.47 mmol) is treated with DMF (30 mL) in a three-necked round bottom flask (100 mL), equipped with a teflon coated magnetic stir bar and gas inlet and outlet (Argon, dry). To the mixture is added Asp (OBz)$_2$ p-TSA (1.57 g, 3.23 mmol, 2.2 equiv), DIPEA (0.45 g, 3.5 mmol), and PyBop (1.67 g, 3.2 mmol) and the mixture allowed to stir overnight. The reaction mixture is concentrated under vacuum by rotavap and purified by normal phase chromatography over silica gel using a Combi-Flash R$_f$ Unit (Teledyne ISCO) and hexanes-EtOAc gradiant. Fractions containing the desired tetra-benzyl ester are combined and concentrated to a solid, substantially pure tetrabenzyl 2,2'-((3,3'-((3,6-diaminopyrazine-2,5-dicarbonyl)bis(azanediyl))bis(propanoyl))bis(azanediyl))(2R,2'R)-disuccinate is obtained and used in the next step. Step 2. Synthesis of (2R,2'R)-2,2'-((3,3'-((3,6-diaminopyrazine-2,5-dicarbonyl)bis(azanediyl))bis(propanoyl))bis(azanediyl))disuccinic acid

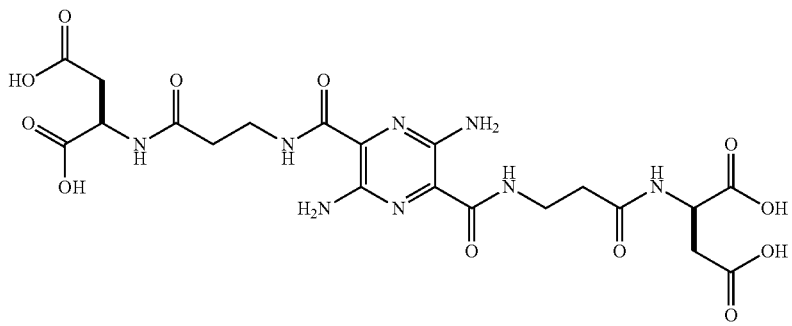 [SMILES: Nc1nc(C(=O)NCCC(=O)N[C@H](CC(=O)O)C(=O)O)c(N)nc1C(=O)NCCC(=O)N[C@H](CC(=O)O)C(=O)O]

Tetrabenzyl 2,2'-((3,3'-((3,6-diaminopyrazine-2,5-dicarbonyl)bis(azanediyl)) bis(propanoyl)) bis(azanediyl))(2R, 2'R)-disuccinate (0.5 g, 0.88 mmol) prepared in Step 1 is placed in a Fischer-Porter pressure bottle (6 oz) equipped with a Teflon covered magnetic stirring bar and dissolved in EtOH (20 mL). Catalyst (0.1 g 5% Pd on carbon) is added and vigorous stirring commenced. After several Ar/vacuum cycles, hydrogen is added and the reaction carried out in a similar fashion to Example 18 and desired product, (2R, 2'R)-2,2'-((3,3'-((3,6-diaminopyrazine-2,5-dicarbonyl)bis(azanediyl)) bis(propanoyl))bis(azanediyl)) disuccinic acid, obtained.

Example 24: Sodium 3,3'-((3,6-diaminopyrazine-2,5-dicarbonyl)bis(azanediyl))bis(4-hydroxybutanoate)

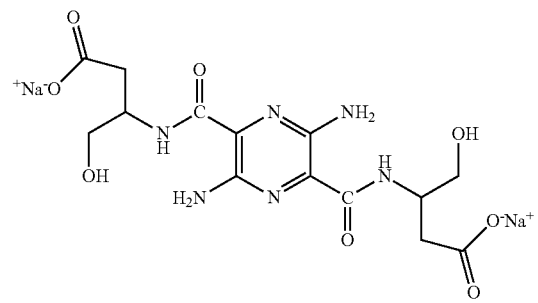

The product di-lactone isolated in Example 20 is dissolved in water (deionized) and two equivalents of base, sodium hydroxide, for example, dissolved in water added with stirring forming the desired di-hydroxy acid sodium salt, sodium 3,3'-((3,6-diaminopyrazine-2,5-dicarbonyl)bis(azanediyl))bis(4-hydroxybutanoate). Solid product may be obtained by removing residual water by distillation or by freeze drying (lyophilizing) the reaction mixture.

Example 25: (2R,2'R)-3,3'-((3,6-diaminopyrazine-2,5-dicarbonyl)bis(azanediyl))bis(2-(hydroxymethyl)propanoic acid)

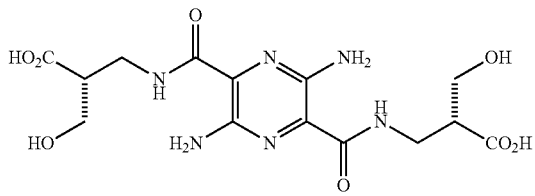 [SMILES: Nc1nc(C(=O)NC[C@H](CO)C(=O)O)c(N)nc1C(=O)NC[C@H](CO)C(=O)O]

Step 1. Synthesis of dimethyl 3,3'-((3,6-diaminopyrazine-2,5-dicarbonyl)bis(azanediyl))(2R,2'R)-bis(2-((benzyloxy)methyl)propanoate)

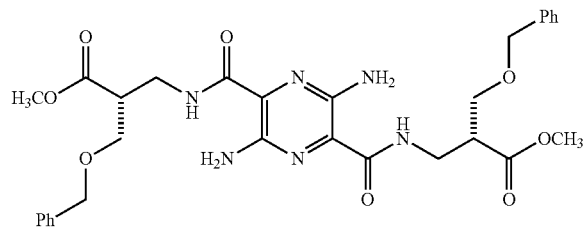 [SMILES: COC(=O)[C@H](CNC(=O)c1nc(N)c(C(=O)NC[C@H](COCc2ccccc2)C(=O)OC)nc1N)COCc1ccccc1]

A mixture of sodium 3,6-diaminopyrazine-2,5-dicarboxylate (300 mg, 1.24 mmol), methyl-2-O-benzyl-3-aminopropionate HCl salt (2.64 mmol), HOBt-H$_2$O (570 mg, 3.72 mmol) and EDC-HCl (690 mg, 3.60 mmol) in DMF (25 mL) is treated with triethylamine (2 mL). The resulting mixture is stirred for 16 h, concentrated, and partitioned between EtOAc and water. The layers are separated and the EtOAc layer washed with NaHCO$_3$ (saturated) and brine. The organic layer is dried over Na$_2$SO$_4$ (anhydrous), filtered and concentrated. Purification by radial flash chromatography (silica) or by reverse phase HPLC using a C18 column affords the desired pyrazine intermediate that is carried forward in the next step.

Step 2. Synthesis of (2R,2'R)-3,3'-((3,6-diaminopyrazine-2,5-dicarbonyl)bis(azanediyl))bis(2-((benzyloxy)methyl)propanoic acid)

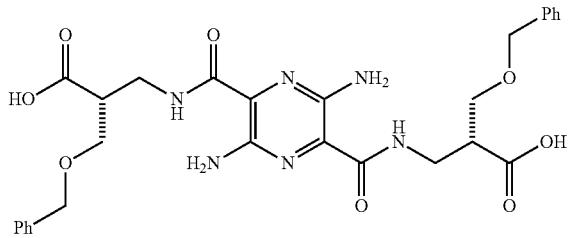 [SMILES: Nc1nc(C(=O)NC[C@H](COCc2ccccc2)C(=O)O)c(N)nc1C(=O)NC[C@H](COCc1ccccc1)C(=O)O]

The product from Step 1 in THF (about 400 mg in about 10 mLs THF) is treated with sodium hydroxide in water (1.0 N). After stirring at room temperature for about 30 min (or until the reaction is deemed complete by TLC) the pH is adjusted to approximately 2 by the addition of HCl in water (1.0 M) and the resulting solution extracted with EtOAc (3×). The organic layers are combined, dried (Na$_2$SO$_4$, anhydrous), filtered and concentrated to afford the diacid.

Step 3. Synthesis of (2R,2'R)-3,3'-((3,6-diaminopyrazine-2,5-dicarbonyl)bis(azanediyl))bis(2-(hydroxymethyl)propanoic acid)

To the product of Step 2 in methanol is added 5% Pd/C and ammonium formate (about a 10 fold molar excess over diacid) and the resulting solution heated to reflux for about 2 hours. The reaction is cooled to room temperature, filtered and concentrated. The residue may be purified either by recrystallizing from an appropriate solvent or by reverse phase HPLC (for example, using a C18 column and a 5-95% gradient acetonitrile in 0.1% TFA and water in 0.1% TFA over about 10 to 30 mins) to obtain the title compound in substantially pure form.

Example 26: Assessing Vasculature in Mice

An exemplary procedure for assessing vasculature is as follows: All experiments will be performed on anesthetized mice. A Maestro in vivo imaging system from CRi or equivalent will be employed. Commercial fluorescein solution for angiography will be obtained and used as is. Pyrazine dyes in a physiological compatible solution (phosphate buffered solution) will be supplied. During the experiment the mouse will be positioned on a thermostated water blanket, with body temperature monitored by a rectal temperature probe. To facilitate imaging of the vessels of interest, the thoracic, abdominal and inguinal areas of the mouse will be shaved, the mouse positioned on its back and the skin over the femoral vasculature resected to expose the vasculature of interest. The jugular vein will be cannulated using a piece of stretched PE10 tubing filled with saline containing 50 U heparin/mL. After the mouse is prepared a bolus injection of dye is administered followed by an i.v. bolus of saline solution. All injections are administered via the cannula established in the jugular vein. The saline solution is used to flush the line and ensure passage of an intact bolus through the femoral vasculature, producing a sharp wavefront.

An exemplary procedure for assessing eye vasculature is as follows: All experiments will be performed on anesthetized mice. Retinal images will be taken using a Phoenix Micron III Retinal Imaging Microscope. Commercial fluorescein solution for eye angiography will be obtained and used as is. The pyrazine dye in a physiological compatible solution (phosphate buffered solution) will be supplied by MediBeacon, LLC. Administration of each agent will be by typical tail vein injection.

Two mice designated 1 and 2 will be evaluated using the fluorescein solution initially. A pre-administration angiogram will be taken followed by administration of the standard fluorescein solution. Angiograms will be taken immediately after administration and then at 5, 10, 30, and 60 minutes post-administration.

Two mice designated 3 and 4 will be evaluated using the pyrazine formulation initially. A pre-administration angiogram will be taken followed by administration of the standard fluorescein solution. Angiograms will be taken immediately after administration and then at 5, 10, 30, and 60 minutes post-administration.

At least 24 hours after the initial experiments on mice 1, 2, 3, and 4, repeat the procedure with mice 1 and 2 receiving the pyrazine formulation and mice 3 and 4 receiving the fluorescein solution. Comparison of all images will be performed.

Example 27: Comparison of Fluorescence Angiography Using Example 2 and Fluorescein In Vivo In a proof of concept study to establish that Example 2 (3,6-diamino-N2,N5-bis(D-serine)-pyrazine-2,5-dicarboxamide) can be used to visualize ocular vasculature, retinal fluorescence was imaged using a Phoenix Micron III Retinal Imaging Microscope following injection of fluorescein and Example 2 in separate, individual mice. Example 2 and fluorescein (both dosed at 1 mg per mouse) was injected in the femoral vein of six week old male C57Bl/6J mice and retinal images were obtained at various times following injection. FIG. 1 shows the images obtained at 2 minutes. Similar structural detail is observed with Example 2 as with fluorescein. Due to the development of cataracts in response to the imaging, longitudinal observation and within animal comparison of fluorescein and Example 2 was not possible.

Example 28: Intraoperative Fluorescence Angiography Assessing Cerebral Perfusion Patients and Subjects Patients undergoing STA-MCA bypass surgery for unilateral major cerebral artery occlusive disease would be enrolled in the study. Indications for STA-MCA bypass surgery for impaired cerebral perfusion would be determined according to the study criteria. In all surgeries, both the frontal and parietal branches of the STA would be anastomosed to the branches of the MCA in an end-to-side fashion. Patients would complete the PET protocol within 1 month before surgery and complete the intraoperative near-infrared ICG videoangiography (ICG-VA) or 3,6-diamino-$N^2$,N-bis(D-serine)-pyrazine-2,5-dicarboxamide protocol during surgery. Following surgery, systolic blood pressure would be strictly controlled between 100 and 140 mmHg, and anticonvulsant medication would be administered intravenously. Using single photon emission computed tomography with technetium-99m hexamethylpropylene amine oxime (99mTc-HM-PAO SPECT), cerebral blood flow (CBF) measurements would be taken at 1 and 7 days after surgery. The postoperative state of the brain and the patency of bypass would also be assessed by magnetic resonance imaging (MRI)/magnetic resonance angiography (MRA) at 1 and 7 days after surgery. If it was suspected that patient presented with symptoms associated with hyperperfusion, evaluation by SPECT and MRI/MRA would be performed.

Patients undergoing craniotomy and clipping surgery for unruptured cerebral aneurysms would serve as control subjects. These subjects presenting with no steno-occlusive disease, as assessed by intracranial MRA and neck MRA/neck ultrasonography, would complete the ICG-VA or 3,6-diamino-$N^2$,$N^5$-bis(D-serine)-pyrazine-2,5-dicarboxamide protocol just after fronto-temporal craniotomy.

The institutional medical review board would approve the study protocol and all patients would provide written informed consent.

ICG-VA and 3,6-diamino-$N^2$,$N^5$-bis(D-serine)-pyrazine-2,5-dicarboxamide Protocol The recommended dose of ICG-VA is 0.1-0.3 mg/kg, and the daily dose would not exceed 5 mg/kg. In this series or arm of the study, patients would complete the ICG-VA study protocol just after fronto-temporal craniotomy, and the patients undergoing bypass surgery would complete the same protocol just after bypass procedure. Subjects would receive a standard dose of 7.5 mg per injection dissolved in 3.0 ml of physiologic saline. The recording would commence and a calculated bolus of ICG would be administered by the anesthesiologist at the surgeon's request. The ICG transit curves intensities would be recorded by an automatic microscope-integrated algorithm using near-infrared light ($\lambda$=800 nm; OPMI Pentero microscope with infrared fluorescence detection hardware and the Flow 800 software analysis tool; Carl Zeiss Meditec, Oberkochen, Germany). This tool features an algorithm for correcting shading and brain pulsation. Fluorescence intensities would be measured in arbitrary intensity units (AIs) that corresponded to the intensity detected by the camera. The additional time needed for ICG angiography was approximately 90 s. Normal cardiac function (ejection fraction >55%) would also be confirmed preoperatively in all patients.

Patients in the 3,6-diamino-$N^2$,$N^5$-bis(D-serine)-pyrazine-2,5-dicarboxamide (Example 2) arm of the study would receive the appropriate dose of pyrazine dye in physiologic saline buffer and would complete the pyrazine dye protocol just after fronto-temporal craniotomy and the patients undergoing bypass surgery would complete the same protocol just after bypass surgery, receiving the standard dose prescribed for the pyrazine dye. Data for this arm would be obtained as outlined in the previous paragraph for ICG.

The course of fluorescent intensities would be measured by freely definable regions of interest (ROIs). The data from ROIs would be exported for further processing after surgery and ICG results would be compared to those obtained by the pyrazine dye.

The following compounds in can generally be made using the methods described above. It is expected that these compounds when made will have activity similar to those that have been prepared.

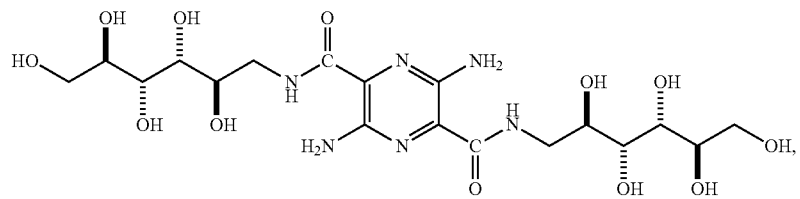

-continued

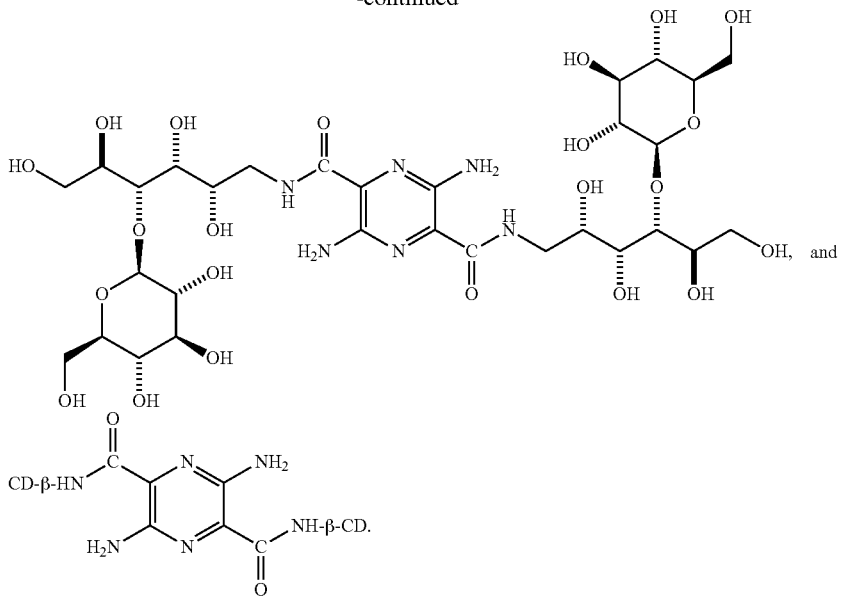

REFERENCES

Zimmern P E, Laub D, Leach G E, Fluorescein angiography of the bladder: technique and relevance to bladder cancer and interstitial cystitis patients. J Urol. 1995; 154(1):62-5.

Gurtner G C, Jones G E, Neligan P C, Newman M I, Phillips B T, Sacks J M, Zenn M R, Intraoperative laser angiography using the SPY system: review of the literature and recommendations for use. Annals of Surgical Innovation and Res 2013, 7:1.

Carus T, Dammer R, Laparoscop fluorescence angiography with indocyanine green to control the perfusion of gastrointestinal anastomoses intraoperatively, Surg. Technol. Int. 2012; 22:27-32.

Lane B C, Cohen-Gadol A A. Fluorescein Fluorescence Use in the Management of Intracranial Neoplastic and Vascular Lesions: A Review and Report of a New Technique, Curr Drug Discov Technol. 2013 June; 10(2):160-9.

Same, P J. Landmarks in the Historical Development of Fluorescein Angiography, J. Ophthal. Photography. 1993; 15(1): 17-23.

Keane, P A. Retinal Imaging in the Twenty-First Century; State of the Art and Future Directions. Ophthalmology. 2014; 121 (12): 2489-2500.

Richard, G, Soubrane, G, Yanuzzi, L. Fluorescein and ICG Angiography: Textbook and Atlas Hardcover. Stuttgart. Thieme. Apr. 23, 1998.

Novotony, H R and Alvis, D L. A method of photographing fluorescence in circulating blood in the human retina. Circulation. 1961; 79: 82-86.

Marmor, M F and Ravin, J G. Fluorescein Angiography, Insight and Serendipidy a Half Century Ago. Arch. Ophthalmol. 2011; 129(7): 943-948.

Chahal, P S, Neal, M J, Kohner, E M. 'Metabolism of Fluorescein after Intravenous Administration'. Investigative Ophthal. and Visual Sci. 1985; 26: 764-768.

Rockey, J H, Li, W, Eccleston, J F, 'Binding of fluorescein and carboxyfluorescein by human serum proteins: significance of kinetic and equilibrium parameters of association in ocular fluorometric studies. Exp. Eye Res. 1983; 37(5): 455-66.

Yannuzzi, L A, et. al., 'Fluorescein Angiography Complication Survey'. Ophthalmology. 1986; 93(5): 611-617.

Gomez-Ulla, F, Gutierriz, C, and Seoane, I, 'Severe anaphylactic reaction to orally administered fluorescein angiography'. Am. J. Ophthalmology, 1991; 112(1):94.

Kwan, A S, Barry, C, McAllister, I L, and Constable, I. 'Fluorescein angiography and adverse drug reactions revisited: the Lion's Eye experience', Clin. Experiment. Ophthalmol. 2006; 34(1): 33-38.

Ascaso, F J, et. al., 'Fatal acute myocardial infarction after intravenous fluorescein angiography', Retina, 1993; 13: 238-239.

Kinsella, F P, Mooney, D J. 'Anaphylaxis Following Oral Fluorescein Angiography'. Am. J. Ophthal. 1988; 106(6): 745-746.

Shirai, K. et al Synthesis and fluorescent properties of 2,5-diamino-3,6-dicyanopyrazine dyes. Dyes and Pigments 1998, 39(1), 49-68.

Kim, J. H. et al. Self-assembling of aminopyrazine fluorescent dyes and their solid state spectra. Dyes and Pigments 1998, 39(4), 341-357.

Barlin, G. B. The Pyrazines. In The Chemistry of Heterocyclic Compounds. A. Weissbeiger and E. C. Taylor, Eds. John Wiley & Sons, New York: 1982.

Donald, D. S. Synthesis of 3,5-diaminopyrazinoic acid from 3,5-diamino-2,6-dicyanopyrazine and intermediates. U.S. patent 1976; U.S. Pat. No. 3,948,895.

Donald, D. S. Diaminosubstituted dicyanopyrzines and process. U.S. patent 1974; U.S. Pat. No. 3,814,757.

Taylor, E C, Jr., Loux, H M, Falco, E A, Hitchings, G H, J. Am. Chem. Soc., 1955, 77: 2243.

Other Embodiments

The detailed description set-forth above is provided to aid those skilled in the art in practicing the present disclosure. However, the disclosure described and claimed herein is not to be limited in scope by the specific embodiments herein disclosed because these embodiments are intended as illustration of several aspects of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are also intended to fall within the scope of the appended claims.

The invention claimed is:

1. A kit for assessing the vasculature in a subject in need thereof, comprising:
   a. a compound of structural Formula I

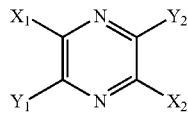

(I)

or a salt thereof; wherein
$X^1$ and $X^2$ are independently chosen from —CO(AA), —CN, —CO$_2$R$^1$, —CONR$^2$R$^3$, —COR$^4$, —NO$_2$, —SOR$^{35}$, —SO$_2$R$^6$, —SO$_2$OR$^7$ and —PO$_3$R$^8$R$^9$; wherein at least one of $X^1$ and $X^2$ is —CO(AA);
$Y^1$ and $Y^2$ are independently chosen from —OR$^{10}$, —SR$^{11}$, —NR$_{12}$R$_{13}$, —N(R$^{14}$)COR$^{15}$, —CONH(PS); —P(R$^{16}$)$_2$, —P(OR$^{17}$)$_2$and

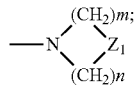

each $Z^1$ is independently chosen from a bond, —CR$^{18}$R$^{19}$—, —O—, —NR$^{20}$—, —NCOR$^{21}$—, —S—, —SO—, and —SO$_2$—;
each R$^1$ to R$^{21}$ are independently chosen from hydrogen, C$_1$-C$_{10}$ alkyl, C$_1$-C$_{10}$ alkyl substituted with hydroxyl and carboxylic acid, C$_3$-C$_6$ polyhydroxylated alkyl, C$_5$-C$_{10}$ aryl, C$_5$-C$_{10}$ heteroaryl, C$_3$-C$_5$ heterocycloalkyl, C$_3$-C$_5$ heterocycloalkyl substituted with C(O), (CH$_2$)$_a$CO$_2$H, —(CH$_2$)$_a$CO$_2$H substituted with C$_5$-C$_{10}$ heteroaryl, —(CH$_2$)$_a$CONR$^{30}$R$^{31}$, —(CH$_2$)$_a$NHSO$_3$$^-$, —(CH$_2$)$_a$NHSO$_3$H, —(CH$_2$)$_a$OH, —(CH$_2$)$_a$OPO$_3$$^-$, —(CH$_2$)$_a$OPO$_3$H$_2$, —(CH$_2$)$_a$OPO$_3$H$^-$, —(CH$_2$)$_a$OR$^{22}$, —(CH$_2$)$_a$OSO$_3$, —(CH$_2$)$_a$OSO$_3$H, —(CH$_2$)$_a$PO$_3$$^-$—(CH$_2$)$_a$PO$_3$H$_2$, —(CH$_2$)$_a$PO$_3$H$^-$, —(CH$_2$)$_a$SO$_3$$^-$, —(CH$_2$)$_a$SO$_3$H, —(CH$_2$)$_a$CO(CH$_2$CH$_2$O)$_c$R$^{23}$, —(CHCO$_2$H)$_a$CO$_2$H, —CH$_2$(CHNH$_2$)$_a$CH$_2$NR$^{25}$R$^{26}$, —CH$_2$(CHOH)$_a$CO$_2$H, —CH$_2$(CHOH)$_a$R$^{27}$, —CH[(CH$_2$)$_b$NH$_2$]$_a$CH$_2$OH, —CH[(CH$_2$)$_b$NH$_2$]$_a$CO$_2$H, and —(CH$_2$)$_a$NR$^{28}$R$^{29}$;
each R$^{22}$ to R$^{31}$ are independently chosen from hydrogen, C$_1$-C$_{10}$ alkyl, and C$_1$-C$_5$-dicarboxylic acid;
R$^{35}$ is chosen from C$_1$-C$_{10}$ alkyl, C$_1$-C$_{10}$ alkyl substituted with hydroxyl and carboxylic acid, C$_3$-C$_6$ polyhydroxylated alkyl, C$_5$-C$_{10}$ aryl, C$_5$-C$_{10}$ heteroaryl, C$_3$-C$_5$ heterocycloalkyl, C$_3$-C$_5$ heterocycloalkyl substituted with C(O), (CH$_2$)$_a$CO$_2$H, (CH$_2$)$_a$CO$_2$H substituted with C$_5$-C$_{10}$ heteroaryl, —(CH$_2$)$_a$CONR$^{30}$R$^{31}$, —(CH$_2$)$_a$NHSO$_3$$^-$, —(CH$_2$)$_a$NHSO$_3$H, —(CH$_2$)$_a$OH, —(CH$_2$)$_a$OPO$_3$$^-$, (CH$_2$)$_a$OPO$_3$H$_2$, —(CH$_2$)$_a$OPO$_3$H$^-$, —(CH$_2$)$_a$OR$^{22}$, (CH$_2$)$_a$OSO$_3$$^-$, —(CH$_2$)$_a$OSO$_3$H, —(CH$_2$)$_a$PO$_3$$^-$, —(CH$_2$)$_a$PO$_3$H$_2$, —(CH$_2$)$_a$PO$_3$H$^-$, —(CH$_2$)$_a$SO$_3$, (CH$_2$)$_a$SO$_3$H, —(CH$_2$)$_a$CO(CH$_2$CH$_2$O)$_c$R$^{23}$, —(CH$_2$)$_d$(CH$_2$CH$_2$O)$_c$R$^{24}$, —(CHCO$_2$H)$_a$CO$_2$H, —CH$_2$(CHNH$_2$)$_a$CH$_2$NR$^{25}$R$^{26}$, —CH$_2$(CHOH)$_a$CO$_2$H, CH$_2$(CHOH)$_a$R$^{27}$, —CH[(CH$_2$)$_b$NH$_2$]$_a$CH$_2$OH, —CHRCH$_2$)$_b$NH$_2$]$_a$CO$_2$H, and —(CH$_2$)$_a$NR$^{28}$R$^{29}$;
(AA) is a polypeptide chain comprising one or more natural or unnatural amino acids linked together by peptide bonds;
(PS) is a sulfated or non-sulfated polysaccharide chain comprising one or more monosaccharide units connected by glycosidic linkages; and
each 'a', and 'd' are independently chosen from 0 to 10, 'c' is chosen from 1 to 100 and each of 'm' and 'n' independently is an integer from 1 to 3; and
   b. written instructions for assessing the eye vasculature in the subject, comprising the steps of:
      i. administering an effective amount of the compound of structural Formula I to be detected in the eye vasculature;
      ii. irradiating the subject's eye vasculature with non-ionizing radiation, wherein the radiation causes the compound to fluoresce;
      iii. detecting the fluorescence of the compound in the subject's eye vasculature; and
      iv. visualizing the eye vasculature within the subject based on the detected fluorescence.

2. The kit of claim 1, wherein said amino acids are chosen from a-amino acids, β-amino acids, and γ-amino acids.

3. The kit of claim 1, wherein the written instructions comprise a step for administering the compound intravenously.

4. The kit of claim 1, wherein the written instructions comprise a step for irradiating the subject's eye vasculature with non-ionizing radiation having a wavelength of at least 350 nm.

5. The kit of claim 1, wherein the written instructions comprise a step for measuring the detected fluorescence of the compound of structural Formula I in the subject's eye vasculature over time.

6. The kit of claim 1, wherein the kit further comprises additional written instructions for assessing the subject's pulmonary and cardiac vasculature.

7. The kit of claim 6, wherein assessing the subject's pulmonary and cardiac vasculature comprises identifying abnormalities chosen from stenosis, occlusions, aneurysms, and combinations thereof.

8. The kit of claim 6, wherein assessing the subject's pulmonary and cardiac vasculature comprises comparing the detected fluorescence in the subject's pulmonary and cardiac vasculature to that of normal pulmonary and cardiac vasculature under similar conditions.

9. The kit of claim 1, wherein assessing the subject's eye vasculature comprises identifying ocular abnormalities.

10. The kit of claim 9, wherein the ocular characteristics are selected from the group consisting of: blood vessel architecture, ischemic spots, choroidal infarcts, Elschnig's spots, exudates, hemorrhages, and combinations thereof.

11. The kit of claim 9, wherein the ocular characteristics are selected from the group consisting of: vessel crossovers, vessel tortuosity, evidence of exudates, and combinations thereof.

12. The kit of claim 1, wherein assessing the subject's eye vasculature comprises comparing the detected fluorescence in the subject's eye to that of a normal eye under similar conditions.

13. The kit of claim 1, wherein $X^1$ and $X^2$ are each —CO(AA) and $Y^1$ and $Y^2$ are each —NR$^{12}$R$^{13}$ wherein one of R$^{12}$ and R$^{13}$ is hydrogen and the other of R$^{12}$ and R$^{13}$ is chosen from hydrogen and C$_1$-C$_{10}$ alkyl.
14. The kit of claim 13 wherein each of R$^{12}$ and R$^{13}$ is hydrogen.
15. The method of claim 1 wherein the compound formula I is
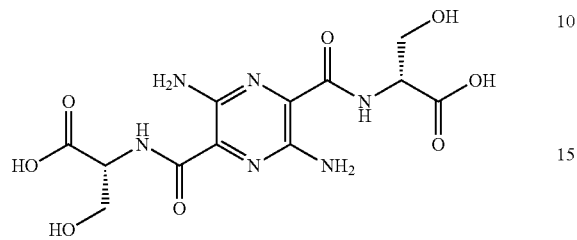
3,6-diamino-N$^2$,N$^5$-bis(D-serine)-pyrazine-2,5-dicarboxamide.
* * * * *